United States Patent
Gallant et al.

(10) Patent No.: US 7,144,896 B2
(45) Date of Patent: Dec. 5, 2006

(54) HETERO-BRIDGE SUBSTITUTED 8-ARYLQUINOLINE PDE4 INHIBITORS

(75) Inventors: Michel Gallant, Montreal (CA); Denis Deschenes, Dorval (CA); Daniel Dube, St-Lazare (CA); Laurence Dube, Pierrefonds (CA); Patrick Lacombe, Montreal (CA); Dwight MacDonald, L'Ile Bizard (CA)

(73) Assignee: Merck Frosst Canada Ltd., Kirkland (CA)

( * ) Notice: Subject to any disclaimer, the term of this patent is extended or adjusted under 35 U.S.C. 154(b) by 22 days.

(21) Appl. No.: 10/508,261

(22) PCT Filed: Mar. 17, 2003

(86) PCT No.: PCT/CA03/00374

§ 371 (c)(1),
(2), (4) Date: Sep. 17, 2004

(87) PCT Pub. No.: WO03/078397

PCT Pub. Date: Sep. 25, 2003

(65) Prior Publication Data

US 2005/0245513 A1    Nov. 3, 2005

Related U.S. Application Data

(60) Provisional application No. 60/365,088, filed on Mar. 18, 2002.

(51) Int. Cl.
*C07D 215/04*    (2006.01)
*A61K 31/47*    (2006.01)

(52) U.S. Cl. .................. 514/314; 514/311; 546/173
(58) Field of Classification Search ............... 514/314, 514/311; 546/173
See application file for complete search history.

(56) References Cited

U.S. PATENT DOCUMENTS 6,919,353 B1 *    7/2005    Dube et al. ................. 514/314

FOREIGN PATENT DOCUMENTS

| WO | WO 94/22852    | 10/1994 |
| WO | WO 01/46151 A1 | 6/2001 |
| WO | WO 02/069970 A1 | 9/2002 |
| WO | WO 03/002118 A1 | 1/2003 |
| WO | WO 03/078397   | 9/2003 |

OTHER PUBLICATIONS

Catherine Burnouf, et al, "Recent Advances in PDE4 Inhibitors as Immunoregulators and Anti-Inflammatory Drugs", Current Pharmaceutical Design, vol. 8, pp. 1255-1296, 2002.
Peter Norman, "PDE4 Inhibitors: sustained Patenting Activity As Leading Drugs Near The Market", Expert Opinion on therapeutic Patents, vol. 10(9), pp. 1415-1427, 2000.

\* cited by examiner

*Primary Examiner*—D. Margaret Seaman
(74) *Attorney, Agent, or Firm*—Curtis C. Panzer; David L. Rose

(57) ABSTRACT

8-arylquinolines wherein the aryl group at the 8-position contains a meta one or two atom bridge to a phenyl, 5 or 6 member heteroaryl or fused bicyclic heteroaryl group, and wherein at least one of the bridge atoms is not carbon, are PDE4 inhibitors.

27 Claims, No Drawings

HETERO-BRIDGE SUBSTITUTED 8-ARYLQUINOLINE PDE4 INHIBITORS

CROSS REFERENCE TO RELATED APPLICATIONS

This application is a U.S. National Phase application under 35 U.S.C. § 371 of PCT Application No. CA03/00374 filed Mar. 17, 2003, which claims priority under 35 U.S.C. 119 to U.S. Provisional Application Nos. 60/365,088 filed Mar. 18, 2002.

BACKGROUND OF THE INVENTION

1. Field of the Invention

The present invention is directed to compounds that are substituted 8-arylquinolines. In particular, this invention is directed to substituted 8-arylquinolines which are phosphodiesterase-4 inhibitors wherein the aryl group at the 8-position contains a meta one or two atom bridge to a phenyl, 5 or 6 member heteroaryl or fused bicyclic heteroaryl group, and wherein at least one of the bridge atoms is not carbon.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

Inhibition of PDE4 activity is believed effective for the treatment of osteoporosis by reducing bone loss. For example, Ken-ici Miyamoto et al., Biochem. Pharmacology, 54:613–617 (1997) describes the effect of a PDE4 on bone loss. Therefore, it would be desirable to provide novel compounds and compositions that inhibit PDE4 activity.

A major concern with the use of PDE4 inhibitors is the side effect of emisis which has been observed for several candidate compounds as described in C. Burnouf et al., ("Burnouf"), Ann. Rep. In Med. Chem., 33:91–109 (1998). B. Hughes et al., Br. J. Pharmacol., 118:1183–1191 (1996); M. J. Perry et al., Cell Biochem. Biophys., 29:113–132 (1998); S. B. Christensen et al., J. Med. Chem., 41:821–835 (1998); and Burnouf describe the wide variation of the severity of the undesirable side effects exhibited by various compounds. As described in M. D. Houslay et al., Adv. In Pharmacol., 44:225–342 (1998) and D. Spina et al., Adv. In Pharmacol., 44:33-89 (1998), there is great interest and research of therapeutic PDE4 inhibitors.

International Patent Publication WO9422852 describes quinolines as PDE4 inhibitors.

A. H. Cook, et al., J. Chem. Soc., 413–417 (1943) describes gamma-pyridylquinolines. Other quinoline compounds are described in Kei Manabe et al., J. Org. Chem., 58(24):6692–6700 (1993); Kei Manabe et al., J. Am. Chem. Soc., 115(12):5324–5325 (1993); and Kei Manabe et al., J. Am. Chem. Soc., 114(17):6940-6941 (1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds. U.S. Pat. No. 5,700,816 described combinations of a cyclooxygenase-2 inhibitor and a leukotriene $A_4$ hydrolase inhibitor.

However, there remains a need for novel compounds and compositions that therapeutically inhibit PDE4 with minimal side effects.

SUMMARY OF THE INVENTION

The present invention is directed to novel substituted 8-arylquinolines that are PDE4 inhibitors, wherein the aryl group at the 8-position contains a meta one or two atom bridge to a phenyl, 5 or 6 member heteroaryl or fused bicyclic heteroaryl group, and wherein at least one of the bridge atoms is not carbon. This invention also provides a pharmaceutical composition which includes an effective amount of the novel substituted 8-arylquinoline and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth, cancerous invasion of normal tissues, osteoporosis, and bone loss by the administration of an effective amount of the novel substituted 8-arylquinoline or a precursor compound which forms in vivo the novel substituted 8-arylquinoline.

DETAILED DESCRIPTION OF THE INVENTION

A compound of this invention is represented by Formula (I):

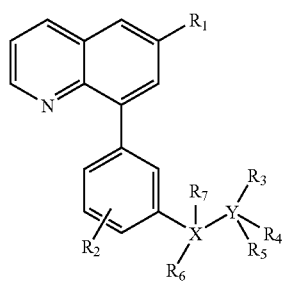

or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH (heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$ alkyl, or —$C_{1-6}$ alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NHC$_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a phenyl group, pyrazolopyrimidinyl group, benzothiazolyol group, quinazolinonyl group, 5-membered heteroaryl containing 1–3 heteroatoms independently O, N, or S group, or 6-membered heteroaryl containing 1–4 heteroatoms independently O, N, or S group, wherein any of the groups is optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl (aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl, substituent group, —O—$C_1$–$C_6$alkyl substituent group, —S—$C_1$–$C_6$alkyl substituent group, —$C_0$–$C_6$alkyl (5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl (6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;

$R_6$ is —H or —$C_1$–$C_6$alkyl;

$R_7$ is —H;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_7$ are absent; and n is 0, 1, or 2.

In one aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)

$C_1$–$C_6$alkyl group, —C(O)NH(aryl) group, —C(O)NH(heteroaryl) group, —$SO_n$NH(aryl) group, —$SO_n$NH (heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —H or halogen;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(-$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;
$R_6$ is —H or —$C_1$–$C_6$alkyl;
$R_7$ is —H;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_7$ are absent; and n is 0, 1, or 2.

In one embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S)-substituent group, —$C_0$–$C_6$alkyl(6-membered heteroaryl containing 1–3 heteroatoms independently O, N, or —S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;
$R_7$ is —H;

X is C;

Y is S;

$R_3$ and $R_5$ are absent; and n is 0, 1, or 2.

In still another embodiment of this aspect, a compound of this invention is represented by Formula (I) or a pharmaceutically acceptable salt thereof, wherein $R_1$ is hydrogen or a halogen, carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —H or halogen;

$R_6$ is —H or —$C_1$–$C_6$alkyl;

$R_7$ is —H;

X is C;

Y is S(O)$_2$;

$R_3$ and $R_5$ are absent; and n is 0, 1, or 2.

In yet another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)

$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;
$R_7$ is —H;
X is C;
Y is N;
$R_5$ is absent; and
n is 0, 1, or 2.

In another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl (5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl (6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;
X is C;
Y is O;
$R_3$ and $R_5$ are absent; and
n is 0, 1, or 2.

In an embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl (5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl (6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;
X is N;
$R_7$ is absent;
Y is C=O;
$R_3$ and $R_5$ are absent; and n is 0, 1, or 2.

In still another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(-$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatom's independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;

X is N;

$R_7$ is absent;

Y is S(O)$_2$;

$R_3$ and $R_5$ are absent; and n is 0, 1, or 2.

In another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

X is N;

Y is N;

$R_3$, $R_5$, $R_6$, and $R_7$ are absent; and n is 0, 1, or 2.

In still another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—

($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a phenyl group optionally substituted with 1–5 substituents; wherein each substituent is independently —OH, —CN, —O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;

X is O;

$R_6$ and $R_7$ are absent;

Y is C; and n is 0, 1, or 2.

In yet another embodiment of this aspect, a compound of this invention is represented by Formula (I) or a pharmaceutically acceptable salt thereof, wherein $R_1$ is hydrogen or a halogen, carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a phenyl group optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)-$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl (5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl (6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

X is O;

$R_6$ and $R_7$ are absent;

Y is S(O)$_2$;

$R_3$ and $R_5$ are absent; and n is 0, 1, or 2.

In another embodiment of this aspect, a compound of this invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH (heteroaryl) group, —SO$_n$NH(C$_1$–C$_6$alkyl) group, —C(O)N(C$_0$–C$_6$alkyl)(C$_0$–C$_6$alkyl) group, —NH—SO$_n$—(C$_1$–C$_6$alkyl) group, —SO$_n$—(C$_1$–C$_6$alkyl) group, -carbamoyl group, —(C$_1$–C$_6$alkyl)-O—C(CN) —N(C$_0$–C$_6$alkyl)(C$_0$–C$_6$alkyl) group, or —(C$_1$–C$_6$alkyl)-SO$_n$—(C$_1$–C$_6$alkyl) group, wherein any of the groups is optionally substituted with 1–5 substituents; wherein each substituent is independently a halogen, —OH, —CN, —C(O)(heterocycloC$_3$–C$_6$alkyl), —C(O)—O—(C$_0$–C$_6$alkyl), —C(O)—O-aryl, C$_1$–C$_6$alkoxy, —C$_3$–C$_6$cycloalkyloxy, acyl, acyloxy, -cycloC$_3$–C$_6$alkyl, heterocycloC$_3$–C$_6$alkyl, aryl, heteroaryl, pyridyl N-oxide, pyridyl N-chloride, -carbonyl-C$_0$–C$_6$alkyl, carbamoyl, or —SO$_n$—(C$_1$–C$_6$alkyl);

R$_2$ is hydrogen, halogen, hydroxyl, —C$_{1-6}$alkyl, or —C$_{1-6}$alkoxy, wherein the alkyl and alkoxy are optionally substituted with 1–3 independently halogen or OH;

R$_3$ is —H, —COOH, —C(O)NH$_2$, or a —C$_1$–C$_6$alkyl group, —C$_1$–C$_4$alkylC$_3$–C$_6$cycloalkyl group, —C(O)C$_3$–C$_6$cycloalkyl group, —C(O)C$_1$–C$_6$alkyl group, —C(O)phenyl group, —C(O)NHphenyl group, —C(O)NHC$_1$–C$_6$alkyl group, —C(O)—O—C$_1$–C$_6$alkyl group, —S(O)$_2$C$_1$–C$_6$alkyl group, —S(O)$_2$phenyl group, —S(O)$_2$C$_1$–C$_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —C$_1$–C$_4$alkyl substituent group, wherein any of the substituent groups is optionally substituted with 1–5 independently —OH or halogen;

R$_4$ is a phenyl group optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(–10–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl(6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen;

R$_5$ is —H;
R$_6$ is —H or —C$_1$–C$_6$alkyl;
R$_7$ is —H;
X is S;
R$_6$ and R$_7$ are absent;
Y is C; and
n is 0, 1, or 2.

In a second aspect, a compound of this invention is represented by Formula (I) or a pharmaceutically acceptable salt thereof, wherein, R$_1$ is hydrogen or a halogen, -carbonyl-C$_0$–C$_6$alkyl, —C$_1$–C$_6$alkyl group, -cycloC$_3$–C$_6$alkyl group, —C$_1$–C$_6$alkenyl group, —C$_1$–C$_6$alkoxy group, aryl group, heteroaryl group, —CN, -heterocycloC$_3$–C$_6$alkyl group, —N(C$_0$–C$_6$alkyl)(C$_0$–C$_6$alkyl) group, —C$_1$–C$_6$alkyl-N(C$_0$–C$_6$alkyl)(C$_0$–C$_6$alkyl) group, —C$_1$–C$_6$alkyl(oxy)C$_1$–C$_6$alkyl group, —C(O)NH(aryl) group, —C(O)NH(heteroaryl) group, —SO$_n$NH(aryl) group, —SO$_n$NH(heteroaryl) group, —SO$_n$NH(C$_1$–C$_6$alkyl) group, —C(O)N(C$_0$–C$_6$alkyl)(C$_0$–C$_6$alkyl) group, —NH—SO$_n$—(C$_1$–C$_6$alkyl) group, —SO$_n$—(C$_1$–C$_6$alkyl) group, -carbamoyl group, —(C$_1$–C$_6$alkyl)-O—C(CN) —N(C$_0$–C$_6$alkyl)(C$_0$–C$_6$alkyl) group, or —(C$_1$–C$_6$alkyl)-SO$_n$—(C$_1$–C$_6$alkyl) group, wherein any of the groups is optionally substituted with 1–5 substituents; wherein each substituent is independently a halogen, —OH, —CN, —C(O)(heterocycloC$_3$–C$_6$alkyl), —C(O)—O—(C$_0$–C$_6$alkyl), —C(O)—O-aryl, C$_1$–C$_6$alkoxy, —C$_3$–C$_6$cycloalkyloxy, acyl, acyloxy, -cycloC$_3$–C$_6$alkyl, heterocycloC$_3$–C$_6$alkyl, aryl, heteroaryl, pyridyl N-oxide, pyridyl N-chloride, -carbonyl-C$_0$–C$_6$alkyl, carbamoyl, or —SO$_n$—(C$_1$–C$_6$alkyl);

R$_2$ is hydrogen, halogen, hydroxyl, —C$_{1-6}$alkyl, or —C$_{1-6}$alkoxy, wherein the alkyl and alkoxy are optionally substituted with 1–3 independently halogen or OH;

R$_3$ is —H, —COOH, —C(O)NH$_2$, or a —C$_1$–C$_6$alkyl group, —C$_1$–C$_4$alkylC$_3$–C$_6$cycloalkyl group, —C(O)C$_3$–C$_6$cycloalkyl group, —C(O)C$_1$–C$_6$alkyl group, —C(O)phenyl group, —C(O)NHphenyl group, —C(O)NHC$_1$–C$_6$alkyl group, —C(O)—O—C$_1$–C$_6$alkyl group, —S(O)$_2$C$_1$–C$_6$alkyl group, —S(O)$_2$phenyl group, —S(O)$_2$C$_1$–C$_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —C$_1$–C$_4$alkyl substituent group, wherein any of the substituent groups is optionally substituted with 1–5 independently —OH or halogen;

R$_4$ is a 5-membered heteroaryl containing 1–3 heteroatoms independently O, N, or S group, optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently OH or halogen;

$R_5$ is —H;

$R_6$ is —H or —$C_1$–$C_6$alkyl;

$R_7$ is —H;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_7$ are absent; and n is 0, 1, or 2.

In an embodiment of this second aspect, a compound of this invention is represented by Formula (I) or a pharmaceutically acceptable salt thereof, wherein, $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a 5-membered heteroaryl containing 1–3 heteroatoms independently O, N, or S group, optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl (aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;

X is N;

$R_7$ is absent;

Y is S(O)$_2$;

$R_3$ and $R_5$ are absent; and n is 0, 1, or 2.

In another embodiment of this second aspect, a compound of this invention is represented by Formula (I) or a pharmaceutically acceptable salt thereof, wherein, $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents, wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a 5-membered heteroaryl containing 1–3 heteroatoms independently O, N, or S group, optionally substituted with 1–5 substituents; wherein each substituent is independently —H, —CN, =O, halogen, —N$_3$, —NO$_2$, —COOH, —$C_1$–$C_{1-C6}$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2C_1$–$C_6$alkyl substituent group, wherein any of the substituent groups is optionally substituted with 1–5 independently —OH or halogen;

X is C=O;

$R_6$ and $R_7$ are absent;

Y is N;

$R_5$ is absent; and n is 0, 1, or 2.

In a third aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2C_1$–$C_6$alkyl group, —S(O)$_2$phenyl group, —S(O)$_2C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a 6-membered heteroaryl containing 1–4 heteroatoms independently O, N, or S group, optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, $C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2C_1$–$C_6$alkyl substituent group, wherein any of the substituent groups is optionally substituted with 1–5 independently —OH or halogen;

$R_5$ is —H;

$R_6$ is —H or —$C_1$–$C_6$alkyl;

$R_7$ is —H;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_1$ are absent; and n is 0, 1, or 2.

In an embodiment of this third aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is a 6-membered heteroaryl containing 1–4 heteroatoms independently O, N, or S group, optionally substituted with 1–5 substituents; wherein each substituent is independently -OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl (5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl (6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;

$R_7$ is —H;

X is C;

Y is S;

$R_3$ and $R_5$ are absent; and n is 0, 1, or 2.

In another embodiment of this third aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN) —N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a 6-membered heteroaryl containing 1–4 heteroatoms independently O, N, or S group, optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_6$ is —H or —$C_1$–$C_6$alkyl;

$R_7$ is —H;

X is C;

Y is N;

$R_5$ is absent; and n is 0, 1, or 2.

In a fourth aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—

($C_1$–$C_6$alkyl) group, —$SO_n$—($C_1$–$C_6$alkyl) group, -carbamoyl group, —($C_1$–$C_6$alkyl)-O—C(CN) —N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a pyrazolopyrimidinyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl (aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl ($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;

$R_6$ is —H or —$C_1$–$C_6$alkyl;

$R_7$ is —H;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_7$ are absent; and n is 0, 1, or 2.

In an embodiment of this fouth aspect, a compound of the present invention is represented by Formula (I) or a pharmaceutically acceptable salt thereof, wherein $R_1$ is hydrogen or a halogen, carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH (heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN) —N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl; —$C_{1-6}$alkyl, or —$C_{1-6}$alkoxy, wherein the alkyl and alkoxy are optionally substituted with 1–3 independently halogen or OH;

$R_3$ is —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a pyrazolopyrimidinyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl (aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl ($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;
$R_6$ is —H or —$C_1$–$C_6$alkyl;
$R_7$ is —H;
X is C;
Y is S; and
n is 0, 1, or 2.

In a fifth aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —CC(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a benzothiazolyol group optionally substituted with 1–5 substituents; wherein each substituent is independently —OH, —CN, =O, halogen, —N$_3$, —NO$_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;
$R_6$ is —H or —$C_1$–$C_6$alkyl;
$R_7$ is —H;
X is O, S, N, C, or C=O, wherein when X is O, S, or C=O then $R_6$ and $R_7$ are absent and when X is N then $R_7$ is absent;
Y is C, S, N, S(O)$_2$, O, or C=O wherein when Y is S, S(O)$_2$, O, or C=O then $R_3$ and $R_5$ are absent, and when Y is N then $R_5$ is absent;
at least one of X and Y must be O, N, S, or S(O)$_2$;
when X and Y are both N, then $R_3$, $R_5$, $R_6$, and $R_7$ are absent; and
n is 0, 1, or 2.

In an embodiment of the fifth aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —SO$_n$NH(aryl) group, —SO$_n$NH(heteroaryl) group, —SO$_n$NH($C_1$–$C_6$alkyl) group, —C(O)N($C_0$–$C_6$alkyl)($C_0$–$C_6$alkyl) group, —NH—SO$_n$—($C_1$–$C_6$alkyl) group, —SO$_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-SO$_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —SO$_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)NH$_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)

phenyl group, —C(O)NHphenyl group, —C(O)NHC$_1$–C$_6$alkyl group, —C(O)—O—C$_1$–C$_6$alkyl group, —S(O)$_2$C$_1$–C$_6$alkyl group, —S(O)$_2$phenyl group, —S(O)$_2$C$_1$–C$_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —C$_1$–C$_4$alkyl substituent group, wherein any of the substituent groups is optionally substituted with 1–5 independently —OH or halogen;

R$_4$ is a benzothiazolyol group optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolylphenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, C$_0$–C$_6$alkyl(6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen;

R$_5$ is —H;

R$_6$ is —H or —C$_1$–C$_6$alkyl;

R$_7$ is —H;

X is C;

Y is S; and n is 0, 1, or 2.

In a sixth aspect, a compound of the present invention is represented by Formula (I) or a pharmaceutically acceptable salt thereof, wherein R$_1$ is hydrogen or a halogen, -carbonyl-C$_0$–C$_6$alkyl, —C$_1$–C$_6$alkyl group, -cycloC$_3$–C$_6$alkyl group, —C$_1$–C$_6$alkenyl group, —C$_1$–C$_6$alkoxy group, aryl group, heteroaryl group, —CN, -heterocycloC$_3$–C$_6$alkyl group, —N(C$_0$–C$_6$alkyl)(C$_0$–C$_6$alkyl) group, —C$_1$–C$_6$alkyl-N(C$_0$–C$_6$alkyl)(C$_0$–C$_6$alkyl) group, —C$_1$–C$_6$alkyl(oxy)C$_1$–C$_6$alkyl group, —C(O)NH(aryl) group, —C(O)NH(heteroaryl) group, —SO$_n$NH(aryl) group, —SO$_n$NH(heteroaryl) group, —SO$_n$NH(C$_1$–C$_6$alkyl) group, —C(O)N(C$_0$–C$_6$alkyl)(C$_0$–C$_6$alkyl) group, —NH—SO$_n$—(C$_1$–C$_6$alkyl) group, —SO$_n$—(C$_1$–C$_6$alkyl) group, -carbamoyl group, —(C$_1$–C$_6$alkyl)-O—C(CN)—N(C$_0$–C$_6$alkyl)(C$_0$–C$_6$alkyl) group, or —(C$_1$–C$_6$alkyl)-SO$_n$—(C$_1$–C$_6$alkyl) group, wherein any of the groups is optionally substituted with 1–5 substituents; wherein each substituent is independently a halogen, —OH, —CN, —C(O)(heterocycloC$_3$–C$_6$alkyl), —C(O)—O—(C$_0$–C$_6$alkyl), —C(O)—O-aryl, C$_1$–C$_6$alkoxy, —C$_3$–C$_6$cycloalkyloxy, acyl, acyloxy, -cycloC$_3$–C$_6$alkyl, heterocycloC$_3$–C$_6$alkyl, aryl, heteroaryl, pyridyl N-oxide, pyridyl N-chloride, -carbonyl-C$_0$–C$_6$alkyl, carbamoyl, or —SO$_n$—(C$_1$–C$_6$alkyl);

R$_2$ is hydrogen, halogen, hydroxyl, —C$_{1-6}$alkyl, or —C$_{1-6}$alkoxy, wherein the alkyl and alkoxy are optionally substituted with 1–3 independently halogen or OH;

R$_3$ is —H, —COOH, —C(O)NH$_2$, or a —C$_1$–C$_6$alkyl group, —C$_1$–C$_4$alkylC$_3$–C$_6$cycloalkyl group, —C(O)C$_3$–C$_6$cycloalkyl group, —C(O)C$_1$–C$_6$alkyl group, —C(O)phenyl group, —C(O)NHphenyl group, —C(O)NHC$_1$–C$_6$alkyl group, —C(O)—O—C$_1$–C$_6$alkyl group, —S(O)$_2$C$_1$–C$_6$alkyl group, —S(O)$_2$phenyl group, —S(O)$_2$C$_1$–C$_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —C$_1$–C$_4$alkyl substituent group, wherein any of the substituent groups is optionally substituted with 1–5 independently —OH or halogen;

R$_4$ is a quinazolinonyl group optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl(6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen;

R$_5$ is —H;

R$_6$ is —H or —C$_1$–C$_6$alkyl;

R$_7$ is —H;

X is O, S, N, C, or C=O, wherein when X is O, S, or C=O then R$_6$ and R$_7$ are absent and when X is N then R$_7$ is absent;

Y is C, S, N, S(O)$_2$, O, or C=O wherein when Y is S, S(O)$_2$, O, or C=O then R$_3$ and R$_5$ are absent, and when Y is N then R$_5$ is absent;

at least one of X and Y must be O, N, S, or S(O)$_2$;

when X and Y are both N, then R$_3$, R$_5$, R$_6$, and R$_7$ are absent; and n is 0, 1, or 2.

In an embodiment of the sixth aspect, a compound of the present invention is represented by Formula (I) or a pharmaceutically acceptable salt thereof, wherein $R_1$ is hydrogen or a halogen, -carbonyl-$C_0$–$C_6$alkyl, —$C_1$–$C_6$alkyl group, -cyclo$C_3$–$C_6$alkyl group, —$C_1$–$C_6$alkenyl group, —$C_1$–$C_6$alkoxy group, aryl group, heteroaryl group, —CN, -heterocyclo$C_3$–$C_6$alkyl group, —N($C_0$–$C_6$alkyl)($C_0$–$C_6$alkyl) group, —$C_1$–$C_6$alkyl-N($C_0$–$C_6$alkyl)($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N($C_0$–$C_6$alkyl)($C_0$–$C_6$alkyl) group, —NH—$SO_n$—($C_1$–$C_6$alkyl) group, —$SO_n$—($C_1$–$C_6$alkyl) group, -carbamoyl group, —($C_1$–$C_6$alkyl)-O—C(CN)—N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O)(heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_{1-6}$alkyl, or —$C_{1-6}$alkoxy, wherein the alkyl and alkoxy are optionally substituted with 1–3 independently halogen or OH;

$R_3$ is —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O)$C_1$–$C_6$alkyl group, —C(O)phenyl group, —C(O)NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O)(5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a quinazolinonyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl(6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H;

$R_6$ is —H or —$C_1$–$C_6$alkyl;

$R_7$ is —H;

X is C;

Y is S; and n is 0, 1, or 2.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic subsituent which is a single ring or multiple rings fused together. When formed of multiple rings, at least one of the constituent rings is aromatic. Examples of aryl are phenyl and napthyl groups.

The term "cycloalkyloxy" unless specifically stated otherwise includes a cycloalkyl group connected by a short $C_1$–$C_2$alkyl length to the oxy connecting atom.

Ther term "$C_0$–$C_6$alkyl" includes alkyls containing 6, 5, 4, 3, 2, 1, or no carbon atoms. An alkyl with no carbon atoms is a hydrogen atom substituent when the alkyl is a terminal moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five member ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

Examples of heterocyclo$C_{3-6}$alkyl include, for example, azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "amine" unless specifically stated otherwise includes primary, secondary and tertiary amines with $C_0$–$C_6$alkyl terminal groups.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, and iii) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues which are responsive to PDE4 inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 mg to about 3.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a ion-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended-recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, infant respiratory distress syndrome, and chronic obstructive pulmonary disease in animals, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, vii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumour growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, or iii) M2/M3 antagonists.

Thus, pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Gastrointestinal disorders such as ulcerative colitis, Crohn's disease, and hypersecretion of gastric acid can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Infectious diseases such as bacterial, fungal or viral induced sepsis or septic shock, endotoxic shock (and associated conditions such as laminitis and colic in horses), and septic shock can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurological disorders such as spinal cord trauma, head injury, neurogenic inflammation, pain, and reperfusion injury of the brain can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Inflammatory disorders such as psoriatic arthritis, rheumatoid arthritis, ankylosing spondylitis, osteoarthritis, inflammation and cytokine-mediated chronic tissue degeneration can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Allergic disorders such as allergic rhinitis, allergic conjunctivitis, and eosinophilic granuloma can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Psychiatric disorders such as depression, memory impairment, and monopolar depression can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurodegenerative disorders such as Parkinson disease, Alzheimer's disease, acute and chronic multiple sclerosis can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Dermatological disorders such as psoriasis and other benign or malignant proliferative skin diseases, atopic dermatitis, and urticaria can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Oncological diseases such as cancer, tumour growth and cancerous invasion of normal tissues can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Metabolic disorders such as diabetes insipidus can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Bone disorders such as osteoporosis, cardiovascular disorders such as arterial restenosis, atherosclerosis, reperfusion injury of the myocardium, and other disorders such as chronic glomerulonephritis, vernal conjunctivitis, transplant rejection and graft versus host disease, and cachexia can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et$_3$N = | triethylamine |
| GST | glutathione transferase |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| Ms0 = | methanesulfonate = mesylate |
| NSAID = | non-steroidal anti-inflammatory drug |
| o-Tol = | ortho-tolyl |
| OXONE ® = | 2KHSO$_5$.KHSO$_4$.K$_2$SO$_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| C$_3$H$_5$ = | allyl |

ALKYL GROUP ABBREVIATIONS

| | |
|---|---|
| Me = | Methyl |
| Et = | ethyl |

-continued

ALKYL GROUP ABBREVIATIONS

| | |
|---|---|
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

ASSAYS DEMONSTRATING BIOLOGICAL ACTIVITY

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α, by increasing intracellular cAMP via PDE4 inhibition and/or enhanced adenylyl cyclase activity occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from *E. coli*, serotype 0111:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10 μL of fMLP (1 μM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for LTB$_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. It is advantageous that the $IC_{50}$ value be less than about 80 µM, more advantageous that it be less than about 10 µM, even more advantageous that it be less than about 1.0 µM, and still more advantageous that it be less than about 0.10 µM. The $IC_{50}$ values of Examples 1 to 116 ranged from 80 µM to 0.029 µM.

Anti-Allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes.

SpA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. the test compound was added (dissolved in 2 µL DMSO), 188 µL of substrate buffer containing [2,8-$^3$H] adenosine 3',5'-cyclic phosphate (cAMP, 100 nM to 50 µM), 10 mM $MgCl_2$, 1 mM EDTA, 50 mM Tris, pH 7.5. The reaction was initiated by the addition of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

The $IC_{50}$ values of Examples 1 to 141 were determined with 100 nM cAMP using the purified GST fusion protein of the human recombinant phosphodiesterase IVa (met-248) produced from a baculovirus/Sf-9 expression system. $IC_{50}$ values should be less than about 1000 nM, advantageously less than about 250 nM, and even more advantageously less than about 100 nM. The $IC_{50}$ values of Examples 1 to 141 ranged from 150 nM to 0.056 nM.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TIC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. Yields are given for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following general methods. The substituents are the same as in Formula I except where defined otherwise.

All 8-aryl-quinoline (III) were prepared (Scheme I) using a Suzuki coupling between the corresponding 8-bromo quinoline (I) and either a boronic acids (II) or a pinacol boronates (V). The latest can be prepared through a palladium catalyzed coupling between an appropriate aryl bromide (IV) and diboron pinacol ester.

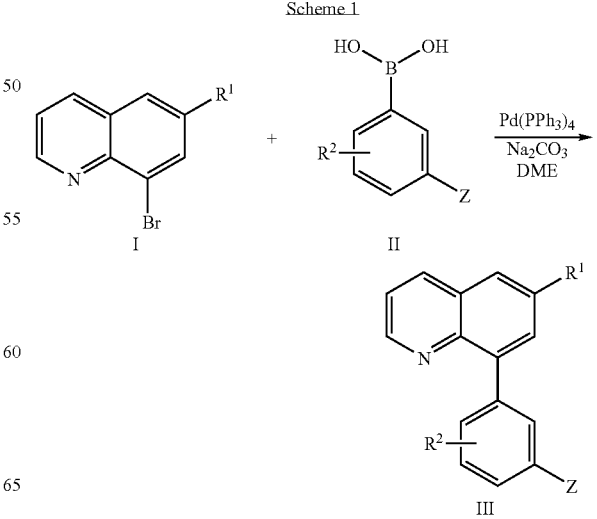

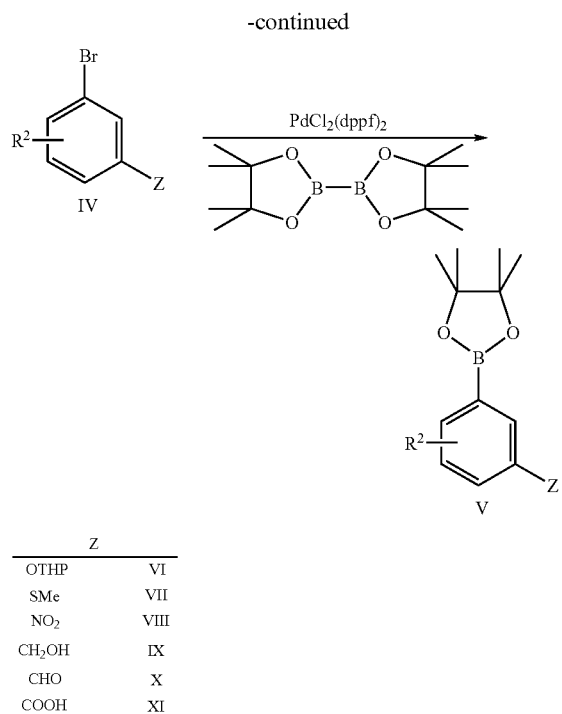
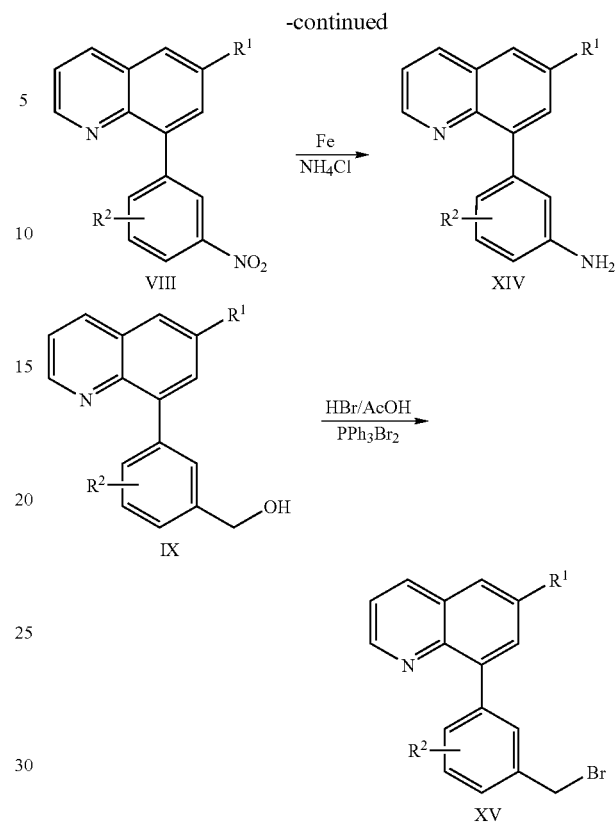

| Z | |
|---|---|
| OTHP | VI |
| SMe | VII |
| NO₂ | VIII |
| CH₂OH | IX |
| CHO | X |
| COOH | XI |

Key intermediates such as the phenols XII, the thiophenols XIII and the anilines XIV (Scheme 2) were obtained by removal of suitable protective or functional groups compatible with the previously described Suzuki coupling (Scheme 2). The THP-ethers VI were deprotected in acidic media while the thioethers VII were deprotected through a Pummerer rearrangement. The anilines XIV were obtained by reduction of the nitro analogs VIII. The hydroxymethyls IX can be converted to their corresponding benzylbromides XV by bromination using HBr/AcOH or PPh₃Br₂.

The cyclopropyl quinoline XIX (Scheme 3) can be prepared in 4 steps from quinoline ester XVI. Reduction and subsequent oxidation of the ester XVI led to the aldehyde XVII which was converted to the vinyl analog XVIII by a Wittig reaction. Finally palladium catalyzed cyclopropanation using diazomethane afforded the cyclopropyl XIX. The methanesulfonyl and the propionitrile quinolines XXIII were prepared in similar fashion in 3 steps starting from the 6-methyl quinoline XX intermediate. Radical bromination followed by nucleophilic displacement with sodium methanesulfonate or potassium cyanide led to the analogs XXII. One pot dialkylation using Kt-OBu and methyl iodide afforded the desired quinolines XXIII.

Scheme 2

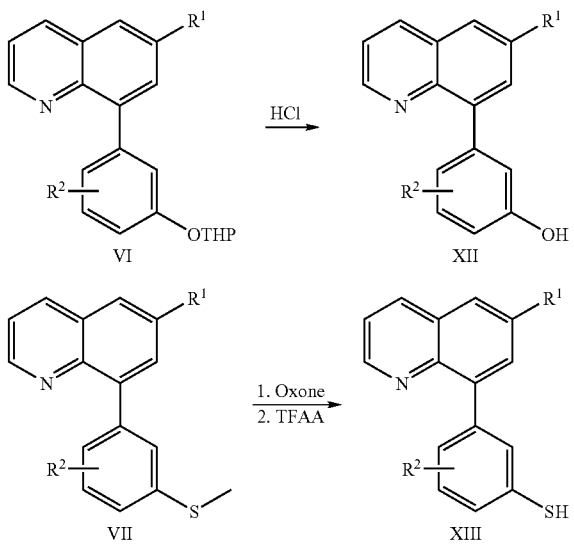

Scheme 3

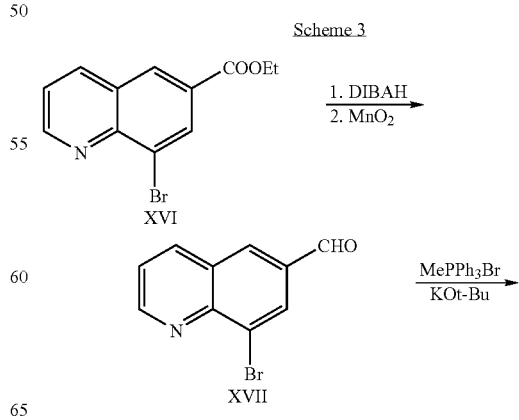

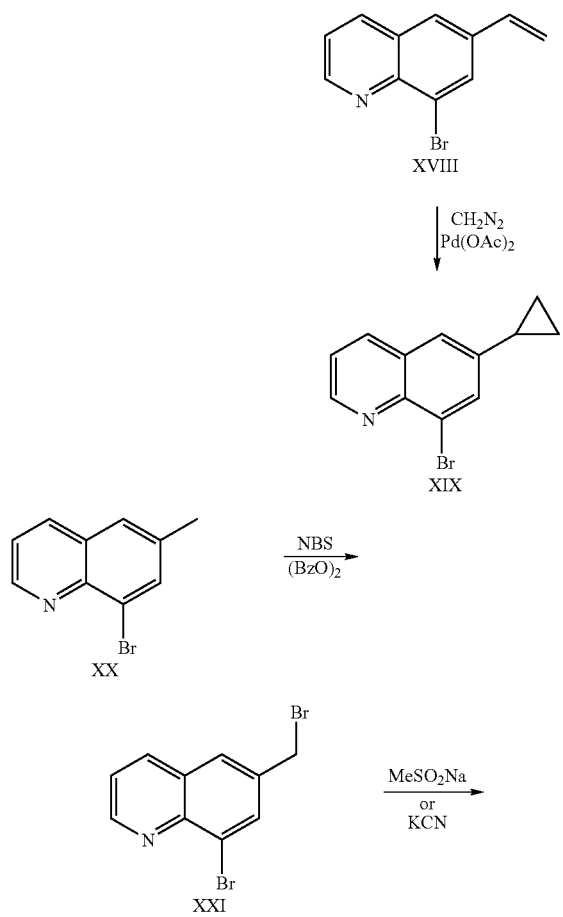
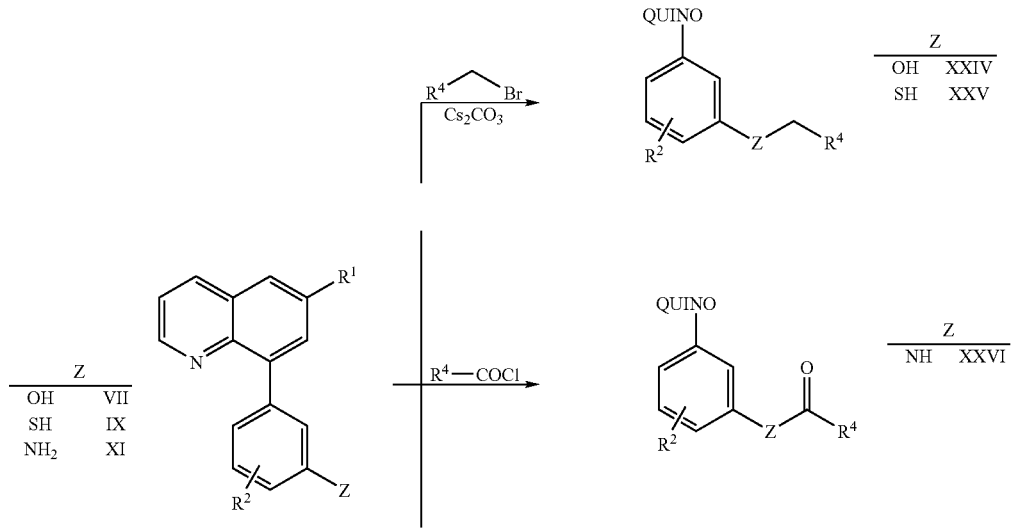
Alkylation of phenols VII and thiophenols IX using Cs$_2$CO$_3$ as base and an appropriate alkyl bromides (R$^4$CH$_2$Br) led to the ethers XXIV and thioethers XXV (Scheme 4). The amides XXVI were prepared by acylation of the corresponding anilines XI. Sulfonylation of phenols VII and anilines XI afforded the corresponding sulfinates XXVII and sulfoamides XXVIII.

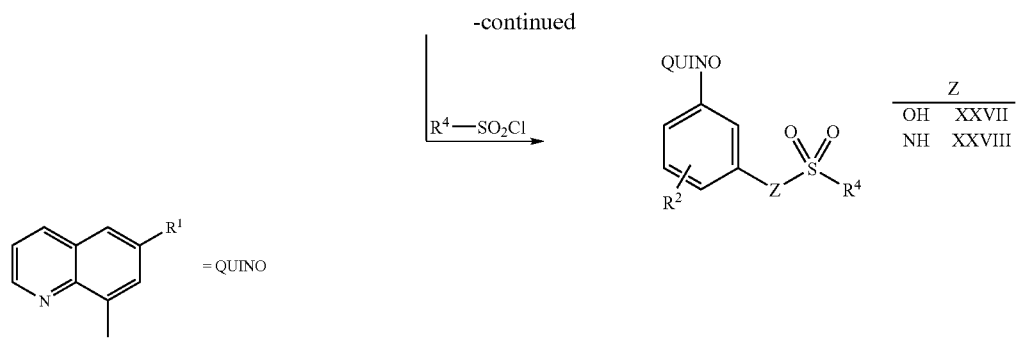

Tertiary alcohols such as XXX can be prepared (Scheme 5) in two steps from the corresponding phenols VII. Alkylation using Cs$_2$CO$_3$ as base and the appropriate 2-bromo acetate led to the esters XXIX which were converted to the tertiary alcohols XXX by addition of methylmagnesium bromide.

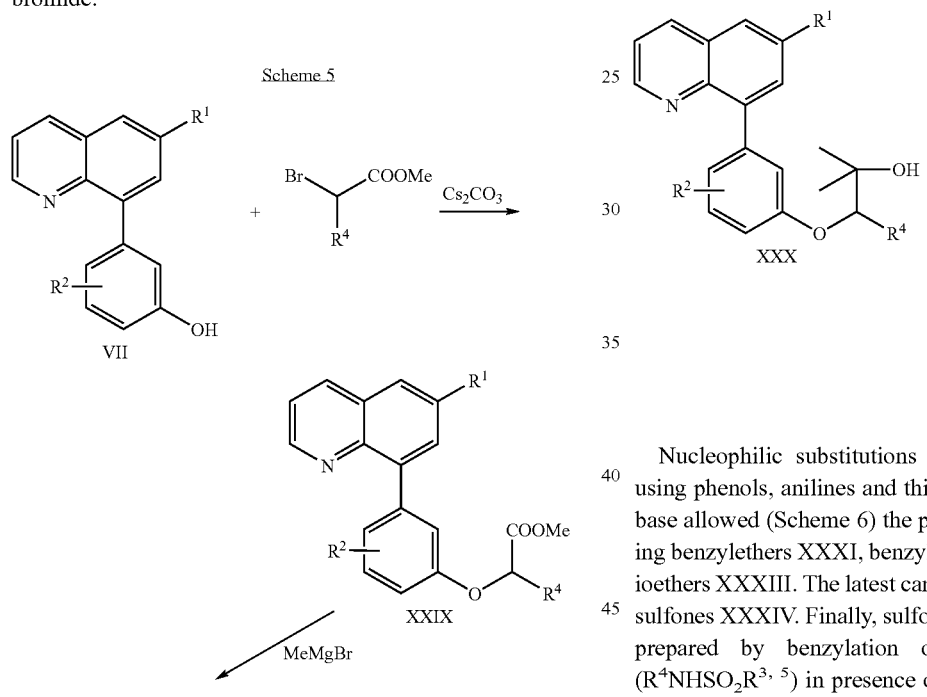

Nucleophilic substitutions on the benzylbromides XV using phenols, anilines and thiophenols with an appropriate base allowed (Scheme 6) the preparation of the corresponding benzylethers XXXI, benzylamines XXXII and benzylthioethers XXXIII. The latest can be oxidized to the analogous sulfones XXXIV. Finally, sulfonamides such as XXXV were prepared by benzylation of secondary sulfonamides (R$^4$NHSO$_2$R$^{3,\ 5}$) in presence of base using XV.

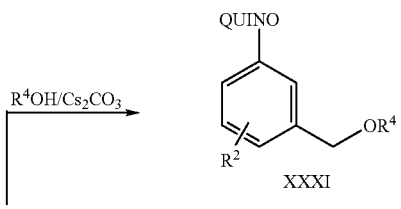

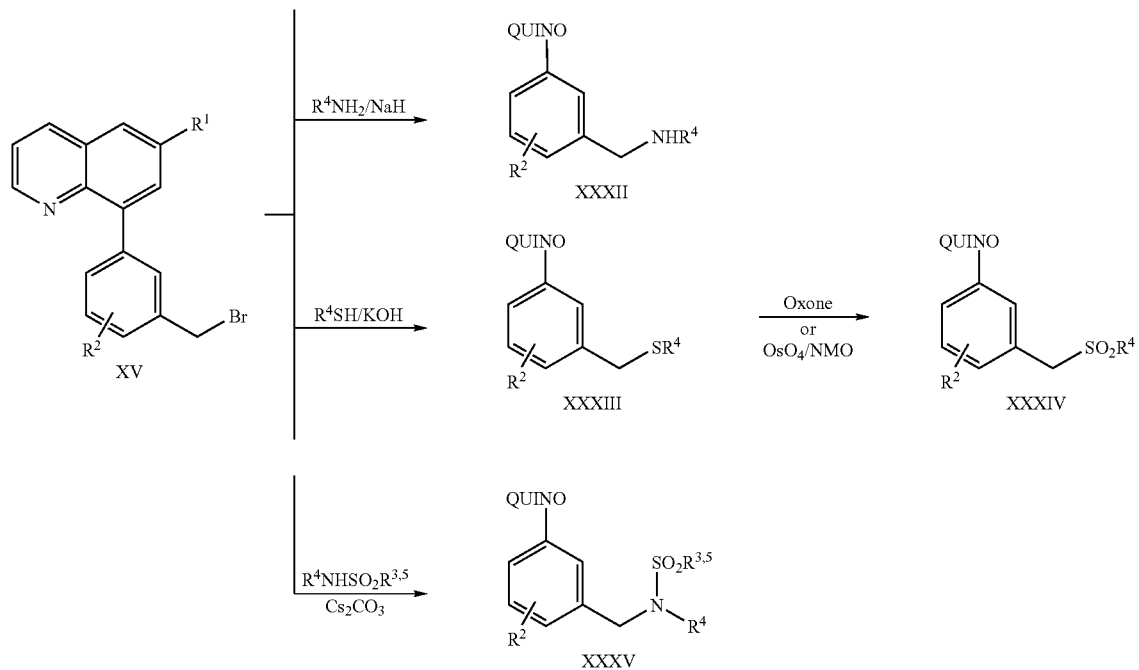

The aniline intermediates XXXVI can be prepared by reductive amination of the corresponding aldehydes X. The methyl substituted analogs XXXVII can be synthesized in two steps by addition of methyl lithium to the previously prepared imine intermediates, which results from the condensation of aldehydes X and anilines $R^4NH_2$. Alkylation of these benzylated anilines led to substituted analogs like XXXVIII while acylation can provide the corresponding amides XXXIX. The urea's XL can be prepared by condensing the anilines XXXVI and XXXVII with an appropriate isocyanate ($R^{3,5}NCO$). Similarly, carbamates XLI were prepared using chloro formate ($R^{3,5}OC(O)Cl$)

Scheme 7

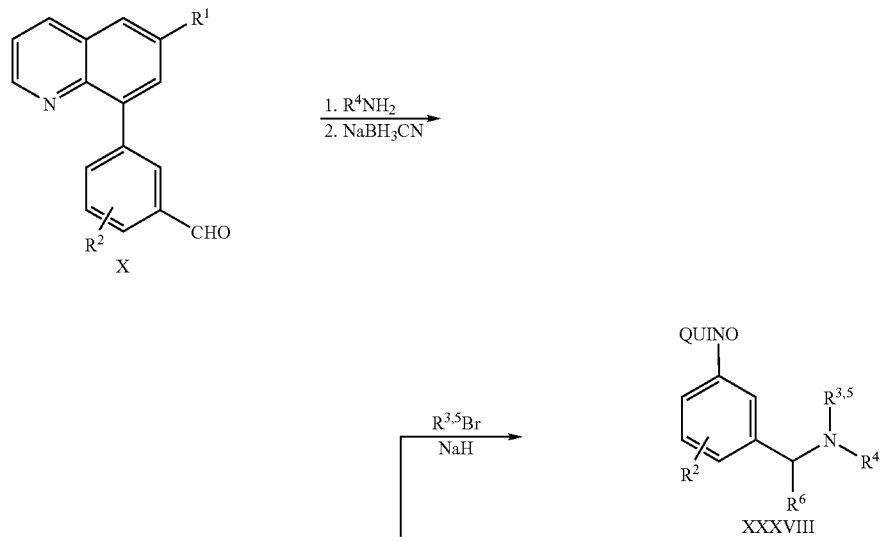

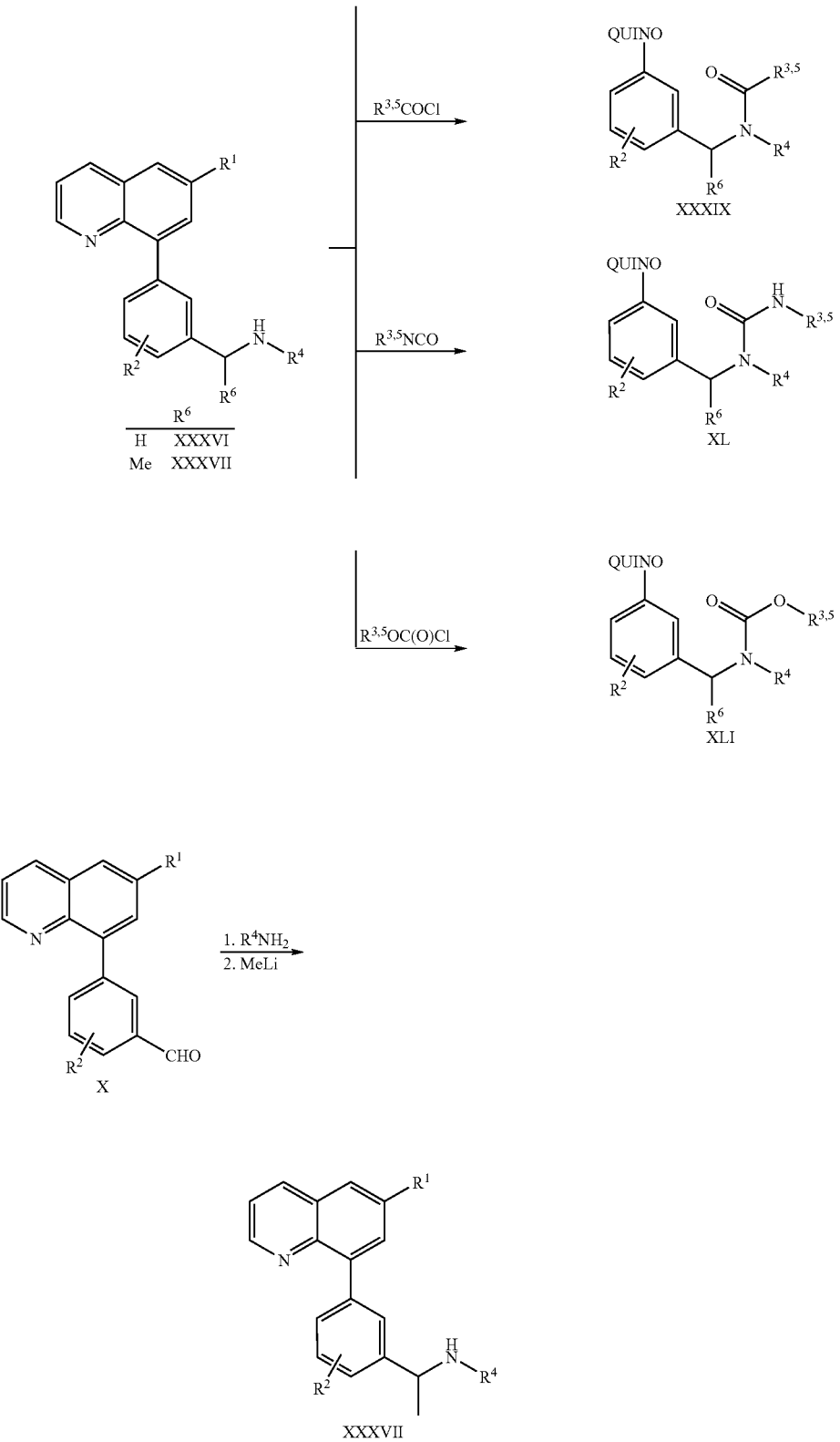

The quinoline intermediates in Table 1 were prepared using the following procedures.

TABLE 1

| Compound | Structure |
| --- | --- |
| Quinoline 1 | 8-bromo-6-isopropylquinoline |
| Quinoline 2 | 3-(6-isopropylquinolin-8-yl)phenol |
| Quinoline 3 | 3-(6-isopropylquinolin-8-yl)benzenethiol |
| Quinoline 4 | (3-(6-isopropylquinolin-8-yl)phenyl)methanol |
| Quinoline 5 | 3-(6-isopropylquinolin-8-yl)benzaldehyde |
| Quinoline 6 | 8-bromo-6-(pyridin-4-ylmethyl)quinoline |

TABLE 1-continued

| Compound | Structure |
| --- | --- |
| Quinoline 7 | (3-(6-(pyridin-4-ylmethyl)quinolin-8-yl)phenyl)methanol |
| Quinoline 8 | 8-(3-(bromomethyl)phenyl)-6-(pyridin-4-ylmethyl)quinoline |
| Quinoline 9 | 3-(6-(pyridin-4-ylmethyl)quinolin-8-yl)aniline |
| Quinoline 10 | 8-bromo-6-(2-(methylsulfonyl)propan-2-yl)quinoline |
| Quinoline 11 | (3-(6-(2-(methylsulfonyl)propan-2-yl)quinolin-8-yl)phenyl)methanol |
| Quinoline 12 | 8-(3-(bromomethyl)phenyl)-6-(2-(methylsulfonyl)propan-2-yl)quinoline |

TABLE 1-continued

| Compound | Structure |
|---|---|
| Quinoline 13 | 6-(2-methanesulfonyl-propan-2-yl)-8-(3-formylphenyl)-quinoline |
| Quinoline 14 | 6-cyclopropyl-8-bromo-quinoline |
| Quinoline 15 | 6-cyclopropyl-8-(3-hydroxymethylphenyl)-quinoline |
| Quinoline 16 | 6-cyclopropyl-8-(3-bromomethylphenyl)-quinoline |
| Quinoline 17 | 6-(2-cyano-propan-2-yl)-8-bromo-quinoline |
| Quinoline 18 | 6-(2-cyano-propan-2-yl)-8-(3-hydroxymethylphenyl)-quinoline |

TABLE 1-continued

| Compound | Structure |
|---|---|
| Quinoline 19 | 6-(2-cyano-propan-2-yl)-8-(3-formylphenyl)-quinoline |
| Quinoline 20 | 6-(1-methylethyl)-8-(3-bromomethylphenyl)-quinoline |
| Quinoline 21 | 6-(2-methanesulfonyl-propan-2-yl)-8-(3-carboxyphenyl)-quinoline |

Quinoline 1

8-Bromo-6-isopropyl-quinoline

The preparation of Quinoline 1 is described in International Patent Publication WO 94/22852.

Quinoline 2

3-(6-Isopropyl-quinolin-8-yl)-phenol

Step 1: 2-[3-(4,4,5,5-Tetramethyl-[1,3,2]dioxaborolan-2-yl)-phenoxy]-tetrahydro-pyran A mixture of 2-(3-Bromophenoxy)-tetrahydro-pyran (1.0 eq), diboron pinacole ester (1.3 eq), KOAc (3.5 eq) and PdCl$_2$(dppf)$_2$ (0.05 eq) in DMF (0.2M) was stirred at 85° C. for 12 h. The resulting mixture was poured in H$_2$O and extracted with Et$_2$O (2×). The combined organic extracts were washed with brine, dried over MgSO$_4$, filtered and concentrated to afford the desired compound as a yellow oil.

Step 2: Quinoline 2

A mixture of the boron ester from present Step 1 (1.0 eq), Quinoline 1 (0.8 eq), aqueous Na$_2$CO$_3$ (3.5 eq; 2.0M) and PdCl$_2$(dppf)$_2$ (0.05) in 100 mL of DME was stirred at 85° C. for 12 h. The resulting mixture was poured in HCl 6N, then

Quinoline 3

3-(6-Isopropyl-quinolin-8-yl)-benzenethiol

Step 1:
6-Isopropyl-8-(3-methylsulfanyl-phenyl)-quinoline

A mixture of Quinoline 1 (1.0 eq), 3-methanesulfanyl-phenyl boronic acid (1.2 eq), aqueous $Na_2CO_3$ (3.5 eq; 2M) and $Pd(PPh_3)_4$ (0.05 eq) in DME (0.32M) was refluxed for 12 h. The resulting mixture was poured in saturated aqueous $NH_4Cl$ and extracted with EtOAc (2×). The combined organic extracts were washed with brine, dried over $MgSO_4$, filtered and concentrated. Flash chromatography (Hex: EtOAc; 9:1) afforded the desired compound as a yellow solid.

Step 2: Quinoline 3

To a solution of the 6-isopropyl-8-(3-methylsulfanyl-phenyl)-quinoline from the previous Step 1 (0.84 g) in MeOH (0.35M) at 0° C. was added a solution of Oxone (0.5 eq) in water (0.18M). The resulting mixture was stirred for 30 min, then poured in saturated aqueous $NaHCO_3$ and extracted with EtOAc (2×). The combined organic extracts were washed with brine, dried over $MgSO_4$, filtered and concentrated. The residual oil was dissolved in TFAA (0.2M), stirred at 40° C. for 30 min and finally concentrated. The residual oil was dissolved in excess $NEt_3$:MeOH (1:1) and concentrated. The operation was repeated twice to afford the title compound as a yellow oil which was used as such.

Quinoline 4

[3-(6-Isopropyl-quinolin-8-yl)-phenyl]-methanol

A mixture of Quinoline 1 (1.0 eq), 3-(hydroxymethyl) phenylboronic acid (1.3 eq), aqueous $Na_2CO_3$ (2.0M; 3.2 eq) and $Pd(PPh_3)_4$ (0.048 eq) in DME (0.15M) was stirred at 80° C. for 12 h. The resulting mixture was cooled to room temperature, diluted with EtOAc, washed with brine, dried over $Na_2SO_4$, filtered and concentrated. Flash chromatography (Hex:EtOAc; 1:1) and stirring in $Et_2O$ yielded the title compound as a white solid after filtration.

Quinoline 5

3-(6-Isopropyl-quinolin-8-yl)-benzaldehyde

Quinoline 5 was prepared according to the procedure described in Quinoline 4, but using 3-(formyl)phenyl boronic acid as the starting material. Flash chromatography (Hex:EtOAc; 4:1) afforded the title compound as a white solid.

Quinoline 6

8-Bromo-6-pyridin-4-ylmethyl-quinoline

The preparation of Quinoline 6 is described in International Patent Publication WO 94/22852.

neutralised to pH 7 and extracted with EtOAc (2×). The combined organic extracts were washed with brine, dried over $MgSO_4$, filtered and concentrated to afford the title compound as a yellow solid.

Quinoline 7

[3-(6-Pyridin-4-ylmethyl-quinolin-8-yl)-phenyl]-methanol

Quinoline 7 was prepared according to the procedure described in Quinoline 4, but using Quinoline 6 as the starting material. Flash chromatography (EtOAc) afforded the title compound as a white solid.

Quinoline 8

8-(3-Bromomethyl-phenyl)-6-pyridin-4-ylmethyl-quinoline

To a solution of Quinoline 7 (1.0 eq) in $CH_2Cl_2$ (0.2M) at 0° C. was added dibromotriphenylphosphine (1.5 eq). The resulting mixture was stirred for 30 min. The reaction was completed (TLC) and the resulting solution was used immediately as such.

Quinoline 9

3-(6-Pyridin-4-ylmethyl-quinolin-8-yl)-phenylamine

Step 1:
8-(3-Nitro-phenyl)-6-pyridin-4-ylmethyl-quinoline

Prepared according to the procedure described in Quinoline 4, but using Quinoline 6 as the starting material and 3-nitro-phenylboronic acid. Flash chromatography (EtOAc) afforded the desired compound as a yellow solid.

Step 2: Quinoline 9

To a solution of the 8-(3-nitro-phenyl)-6-pyridin-4-ylmethyl-quinoline (1.0 eq) described in Step 1 in EtOH (0.2M) at 60° C. was added of water (final concentration 0.15M) and saturated aqueous $NH_4Cl$ (1.3 eq) followed by iron (12 eq). The final mixture was stirred at 60° C. for 2 h, cooled to room temperature, filtered on celite and concentrated to afford the title compound as a yellow solid.

Quinoline 10

8-Bromo-6-(1-methanesulfonyl-1-methyl-ethyl)-quinoline

Step 1:
8-Bromo-6-methanesulfonylmethyl-quinoline

To a solution of 6-bromomethyl-8-bromoquinoline (1.0 eq) (described in International Patent Publication WO 94/22852) in of DMF (0.5M) was added sodium methanesulfinate (1.3 eq). After stirring overnight at room temperature, the resulting mixture was quenched with $H_2O$ (4× volume of DMF), stirred for one hour. The resulting precipitate was isolated by filtration and washed with $Et_2O$ to afford the 8-bromo-6-methanesulfonylmethyl-quinoline compound.

Step 2: Quinoline 10

To a solution of the 8-bromo-6-methanesulfonylmethyl-quinoline (1.0 eq) from Step 1 in THF (0.1M) at 0° C., was added potassium t-butoxide (1.3 eq; 1M in THF) over 30 min. After 0.5 h at 0° C., MeI (1.6 eq) was added and the resulting reaction mixture was stirred at 0° C. for 2 h. A second portion of potassium t-butoxide (1.0 eq; 1M in THF) was added over 30 min, followed by MeI (1.6 eq). The mixture was stirred at room temperature for 2 h. The mixture was poured in saturated aqueous NH$_4$Cl and extracted with EtOAc (2×). The combined organic extracts were washed with brine, dried over MgSO$_4$, filtered and concentrated. The residue was vigorously stirred in Et$_2$O and the title compound was isolated by filtration as a pale yellow solid.

Quinoline 11

{3-[6-(1-Methanesulfonyl-1-methyl-ethyl)-quinolin-8-yl]-phenyl}-methanol

Quinoline 11 prepared according to the procedure described in Quinoline 4 but using Quinoline 10 as the starting material. The reaction mixture was filtered on silica gel and eluted with EtOAc. The organic extracts were combined and concentrated. The resulting residue was diluted with Et$_2$O/EtOAc and stirred vigorously for 3 h. The desired material was isolated as a white solid by filtration, Quinoline 12

8-(3-Bromomethyl-phenyl)-6-(1-methanesulfonyl-1-methyl-ethyl)-quinoline

A suspension of Quinoline 11 (1.0 eq) in a mixture of AcOH and aqueous HBr (48%) (0.45M) was stirred for 18 h at 80° C. The resulting mixture was cooled to 0° C. poured into ice cold NaOH (0.3N). The pH of was adjusted to 5 and filtered. The resulting solid was dissolved in EtOAc, washed with saturated aqueous NaHCO$_3$, brine, dried over MgSO$_4$, filtered and concentrated. Stirring vigorously in Et$_2$O/EtOAc, followed by filtration afforded the title compound as a pale brown solid.

Quinoline 13

3-[6-(1-Methanesulfonyl-1-methyl-ethyl)-quinolin-8-yl]-benzaldehyde

Prepared according to the procedure described in Quinoline 4, but using Quinoline 10 and 3-formyl phenylboronic acid as the starting materials. The title compound was isolated as a light yellow solid.

Quinoline 14

8-Bromo-6-cyclopropyl-quinoline

Step 1: 8-Bromo-quinoline-6-carbaldehyde

To a solution of 8-bromo-quinoline-6-carboxylic acid ethyl ester (1.0 eq) in CH$_2$Cl$_2$ (0.26M) at −78° C. was added dropwise DIBAL (neat; 2.0 eq). The resulting mixture was stirred 1 h at −78° C. then poured in Na/K tartrate (2N) and stirred for 2 h. The mixture was extracted with EtOAc (2×). The combined organic extracts were washed with brine, dried over MgSO$_4$, filtered and concentrated to afford the desired compound along with the corresponding hydroxymethyl analog. To the mixture dissolved in EtOAc (0.45M) was added MnO$_2$ (2.5 eq). The resulting mixture was refluxed for 1 h, cooled to room temperature, filtered on a pad of silica gel and concentrated. The residual solid was vigorously stirred in Hex/Et$_2$O (2/1) for 2 h to afford following filtration the desired compound as a light yellow solid.

Step 2: 8-Bromo-6-vinyl-quinoline

To a solution of methyl-triphenyl phosphonium bromide (1.15 eq) in THF (0.3M) at 0° C. was added K-tOBu (1.15 eq). The resulting mixture was stirred for 30 min after which a solution of the 8-bromo-quinoline-6-carbaldehyde from Step 1 (1.0 eq) was added. The final mixture was stirred at room temperature for 12 h, poured in saturated aqueous NH$_4$Cl and extracted with EtOAc (2×). The combined organic extracts were washed with brine, dried over MgSO$_4$, filtered and concentrated. Flash chromatography (Hex: EtOAc; 9:1) afforded the desired compound as a yellow solid.

Step 3: Quinoline 14

To a solution of vinyl quinoline from Step 2 (1.0 eq) in THF (0.45M) was added Pd(OAc)$_2$ (0.05 eq). Diazomethane solution in Et$_2$O was added portion wise until the reaction was completed (NMR of aliquot). The mixture was concentrated and flash chromatography (Hex:EtOAc; 4:1) afforded the Quinoline 14 as an oil.

Quinoline 15

[3-(6-Cyclopropyl-quinolin-8-yl)-phenyl]-methanol

Quinoline 15 was prepared according to the procedure described in Quinoline 4, but using Quinoline 14 as the starting material. Flash chromatography (Hex:EtOAc; 1:1) afforded the title compound as a white solid.

Quinoline 16

8-(3-Bromomethyl-phenyl)-6-cyclopropyl-quinoline

Quinoline 16 was prepared according to the procedure described in Quinoline 12, but using Quinoline 15 as the starting material. Vigorous stirring in Hex/CH$_2$Cl$_2$ 10%, followed by filtration afforded the title compound as a light yellow solid.

Quinoline 17

2-(8-Bromo-quinolin-6-yl)-2-methyl-propionitrile

Step 1: (8-Bromo-quinolin-6-yl)-acetonitrile

To a solution 6-bromomethyl-8-bromoquinoline (described in International Patent Publication WO 94/22852) (1.0 eq) in DMF:H$_2$O (2:1, 0.66M) was added potassium cyanide (2.5 eq). After heating at 100° C. for 1 h, the resulting mixture was quenched with H$_2$O and extracted with EtOAc (2 x). The combined organic extracts were washed with water (3×), brine, dried over MgSO4, filtered and concentrated. Flash chromatography (Hex:EtOAc, 3:1) yielded the desired compound as a white solid.

Step 2: Quinoline 17

To a solution of (8-bromo-quinolin-6-yl)-acetonitrile from Step 1 (1.0 eq) in THF (0.12M) at −78° C., was added MeI (2.3 eq) followed by potassium t-butoxide (2.3 eq).

After 2 h at −78° C., the resulting mixture was warmed to 0° C. and was poured in saturated aqueous NH$_4$Cl, then extracted with EtOAc (2×). The combined organic extracts were washed with brine, dried over MgSO$_4$, filtered and concentrated. Flash chromatography (Hex:EtOAc, 3:1) afforded the title compound as a white solid.

Quinoline 18

2-[8-(3-Hydroxymethyl-phenyl)-quinolin-6-yl]-2-methyl-propionitrile

Quinoline 18 was prepared according to the procedure described in Quinoline 4, but using Quinoline 17 as the starting material. Flash chromatography (Hex:EtOAc; 1:1) and stirring in Et$_2$O yielded after filtration the title compound as a white solid

Quinoline 19

2-[8-(3-Formyl-phenyl)-quinolin-6-yl]-2-methyl-propionitrile

Quinoline 19 was prepared according to the procedure described in Quinoline 4, but using Quinoline 17 and 3-(formyl)phenyl boronic acid as the starting materials. Flash chromatography (Hex:EtOAc; 2:1) and vigourous stirring in Et$_2$O yielded the title compound after filtration as a white solid.

Quinoline 20

8-(3-Bromomethyl-phenyl)-6-isopropyl-quinoline

Quinoline 20 was prepared according to the procedure described in Quinoline 12, but using Quinoline 4 as the starting material. The title compound was obtained as a yellow solid.

Quinoline 21

3-[6-(1-Methanesulfonyl-1-methyl-ethyl)-quinolin-8-yl]-benzoic acid

Step 1: 3-[6-(1-Methanesulfonyl-1-methyl-ethyl)-quinolin-8-yl]-benzoic acid methyl ester To a solution of Quinoline 13 (1.0 eq) in CH$_2$Cl$_2$:MeOH (1:2; 0.05M) NaCN (1.8 eq), AcOH (1.05 eq) and MnO$_2$ (8.0 eq). The resulting mixture was stirred for 12 h then filtered on celite. The mother liquor was dried over MgSO$_4$, filtered and concentrated. Flash chromatography (Hex:EtOAc, 1:1) afforded the desired compound as a white solid.

Step 2: Quinoline 21

To a solution of 3-[6-(1-methanesulfonyl-1-methylethyl)-quinolin-8-yl]-benzoic acid methyl ester from Step 1 (1.0 eq) in THF (20 mL) was added LiOH (2.5 eq; 2.0N in water). The mixture was stirred at 65° C. for 6 h then poured in NaOH (1N) then extracted with CH$_2$Cl$_2$ (2×). The organic extracts were discarded while the aqueous phase was acidified to pH=5 using AcOH. The latter was extracted with CH$_2$Cl$_2$ (5×). The combined organic extracts were dried over MgSO$_4$, filtered and concentrated. The resulting solid was stirred in a mixture of EtOAc:Hex:Et$_2$O (0.1:1:1) then filtered to afforded the title compound as a white solid.

Compounds of the present invention can be prepared according to the following methods. In the present text, a suspension-filtration sequence means that a residue (oil or solid) was dissolved in a polar solvent and precipitated by adding the less polar solvent while stirring. The precipitate was then isolated by filtration.

EXAMPLE 1

6-Isopropyl-8-[3-(4-methanesulfonyl-benzyloxy)-phenyl]-quinoline

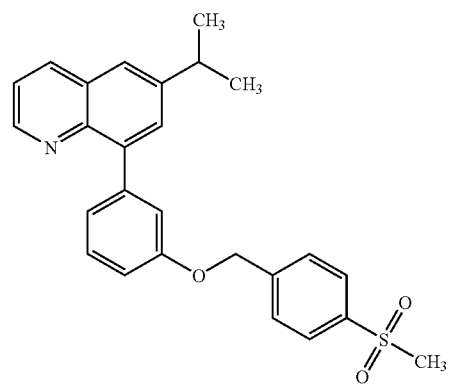

To a solution of Quinoline 2 (1.0 eq) in acetone (0.2M) was added Cs$_2$CO$_3$ (1.5 eq) and 1-chloromethyl-4-methanesulfonyl-benzene (1.5 eq). The resulting mixture was stirred 2 days at room temperature, poured in water and extracted with Et$_2$O (2×). The combined organic extracts were washed with brine, dried over MgSO$_4$, filtered and concentrated. Flash chromatography (Hex:EtOAc; 9:1 to 1:9 in 15 min) afforded the title compound as a white solid.
$^1$H NMR (400 MHz, acetone-d$_6$): δ 8.79 (dd, 1H), 8.30 (dd, 1H), 7.98 (d, 2H), 7.78 (d, 2H), 7.70 (d, 1H), 7.47 (dd, 1H), 7.40 (m, 2H), 7.3 (d, 1H), 7.07 (dd, 1H), 5.3 (s, 2H), 3.16 (m, 1H), 3.12 (s, 3H), 1.37 (d, 6H).

EXAMPLE 2

2-[3-(6-Isopropyl-quinolin-8-yl)-phenoxymethyl]-benzonitrile

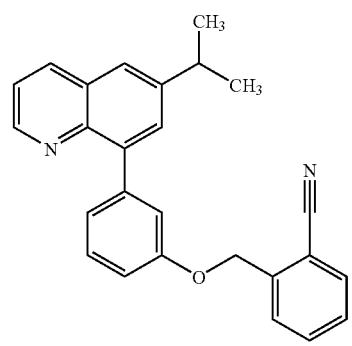

Prepared according to the procedure described in EXAMPLE 1, but using 2-bromomethyl-benzonitrile as the starting material. The title compound was obtained as an oil.

¹H NMR (400 MHz, acetone-d₆): δ 8.80 (dd, 1H), 8.29 (dd, 1H), 7.84–7.71 (m, 5H), 7.56 (dt, 1H), 7.48–7.32 (m, 4H), 7.11 (dd, 1H), 5.37 (s, 2H), 3.16 (m, 1H), 1.37 (d, 6H).

EXAMPLE 3

3-[3-(6-Isopropyl-quinolin-8-yl)-phenoxymethyl]-benzonitrile

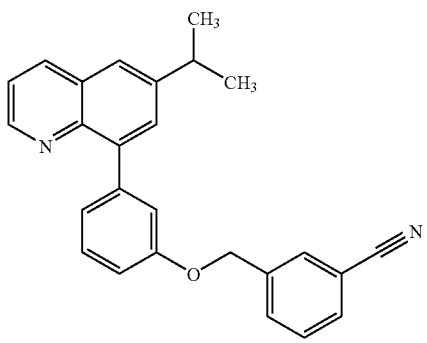

Prepared according to the procedure described in EXAMPLE 1 but using 3-bromomethyl-benzonitrile as the starting material. The title compound was obtained as a white solid.

¹NMR (400 MHz, acetone-d₆): δ 8.79 (dd, 1H), 8.30 (dd, 1H), 7.92 (s, 1H), 7.85 (d, 1H), 7.77–7.73 (m, 2H), 7.69 (d, 1H), 7.62 (t, 1H), 7.46 (dd, 1H), 7.40 (m, 2H), 7.30 (dd, 1H), 7.07 (ddd, 1H), 5.27 (s, 2H), 3.16 (m, 1H), 1.37 (d, 6H).

EXAMPLE 4

4-[3-(6-Isopropyl-quinolin-8-yl)-phenoxymethyl]-benzonitrile

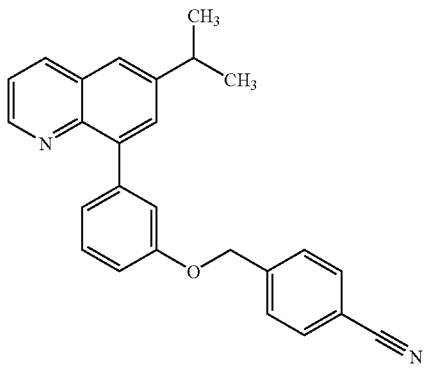

Prepared according to the procedure described in EXAMPLE 1 but using 4-bromomethyl-benzonitrile as the starting material. The title compound was obtained as a white solid.

¹H NMR (400 MHz, acetone-d₆): δ 8.79 (dd, 1H), 8.29 (dd, 1H), 7.81–7.68 (m, 6H), 7.46 (dd, 1H), 7.40 (m, 2H), 7.30 (dd, 1H), 7.06 (ddd, 1H), 5.3 (s, 2H), 3.16 (m, 1H), 1.36 (d, 6H).

EXAMPLE 5

8-[3-(2-Benzenesulfonylmethyl-benzyloxy)-phenyl]-6-isopropyl-quinoline

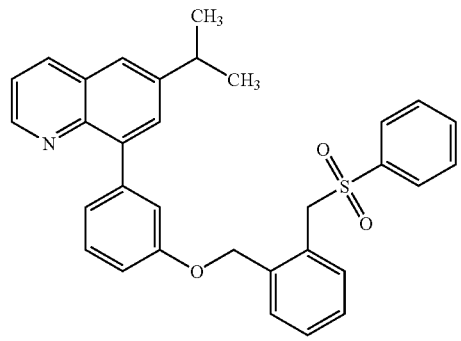

Prepared according to the procedure described in EXAMPLE 1 but using 2-benzenesulfonylmethyl-benzylbromide as the starting material. The title compound was obtained as an oil.

¹H NMR (400 MHz, acetone-d₆): δ 8.81 (dd, 1H), 8.30 (dd, 1H), 7.77–7.71 (m, 4H), 7.66 (t, 1H), 7.58–7.52 (m, 3H), 7.47 (dd, 1H), 7.38 (m, 3H), 7.31 (d, 1H), 7.25 (t, 1H), 7.18 (d, 1H), 7.02 (ddd, 1H), 5.22 (s, 2H), 4.73 (s, 2H), 3.16 (m, 1H), 1.37 (d, 6H).

EXAMPLE 6

6-Isopropyl-8-[3-(4-trifluoromethoxy-benzyloxy)-phenyl]-quinoline

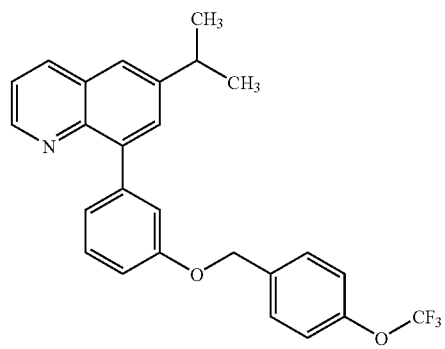

Prepared according to the procedure described in EXAMPLE 1 but using 4-trifluoromethoxy-benzylbromide as the starting material. The title compound was obtained as an oil.

¹H NMR (400 MHz, acetone-d₆): δ 8.80 (dd, 1H), 8.30 (dd, 1H), 7.77 (d, 1H), 7.69 (d, 1H), 7.65 (d, 2H), 7.47 (dd, 1H), 7.40–7.35 (m, 4H), 7.30 (dd, 1H), 7.05 (ddd, 1H), 5.22 (s, 2H), 3.16 (m, 1H), 1.37 (d, 6H).

EXAMPLE 7

6-Isopropyl-8-[3-(3-trifluoromethylsulfanyl-benzyloxy)-phenyl]-quinoline

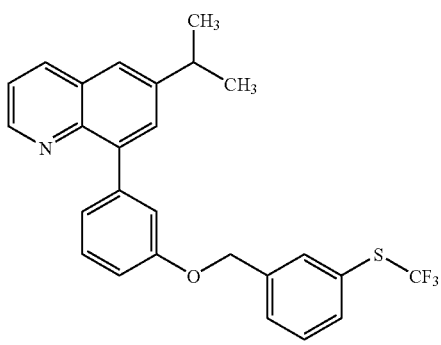

Prepared according to the procedure described in EXAMPLE 1 but using (3-trifluoromethylsulfanyl-benzyl-bromide as the starting material. The title compound was obtained as an oil.

$^1$H NMR (400 MHz, acetone-d$_6$): δ 8.79 (dd, 1H), 8.29 (dd, 1H), 7.88 (s, 1H), 7.76 (m, 2H), 7.70 (m, 2H), 7.57 (t, 1H), 7.46 (dd, 1H), 7.41 (dd, 1H), 7.37 (d, 1H), 7.31 (dd, 1H), 7.07 (ddd, 1H), 5.26 (s, 2H), 3.16 (m, 1H), 1.37 (d, 6H).

EXAMPLE 8

6-Isopropyl-8-[3-(4-[1,2,3]thiadiazol-4-yl-benzyloxy)-phenyl]-quinoline

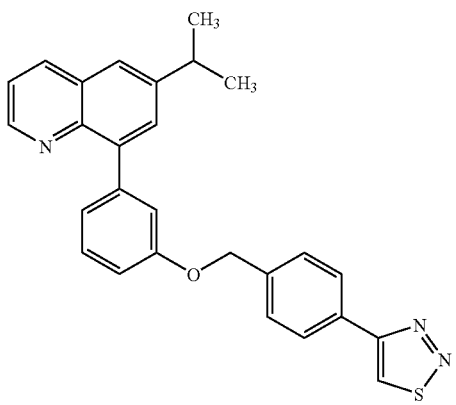

Prepared according to the procedure described in EXAMPLE 1 but using 4-(4-bromomethyl-phenyl)-[1,2,3]thiadiazole as the starting material; The title compound was obtained as a white solid.

$^1$H NMR (400 MHz, acetone-d$_6$): δ 9.33 (s, 1H), 8.80 (dd, 1H), 8.28 (dd, 1H), 8.18 (d, 2H), 7.75 (d, 1H), 7.68 (m, 3H), 7.45 (dd, 1H), 7.43 (dd, 1H), 7.38 (t, 1H), 7.30 (d, 1H), 7.07 (dd, 1H), 5.26 (s, 2H), 3.14 (m, 1H), 1.35 (d, 6H).

EXAMPLE 9

4-[3-(6-Isopropyl-quinolin-8-yl)-phenoxymethyl]-benzoic acid methyl ester

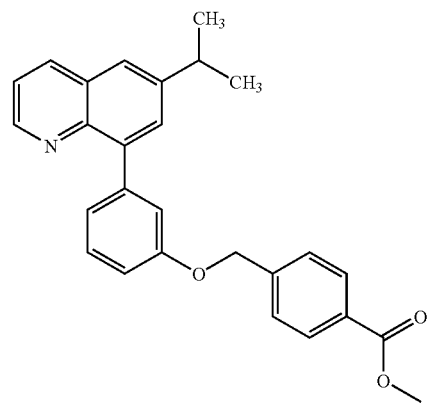

Prepared according to the procedure described in EXAMPLE 1 but using 4-bromomethyl-benzoic acid methyl ester as the starting material. The title compound was obtained as a white solid.

$^1$H NMR (300 MHz, acetone-d$_6$): δ 8.79 (dd, 1H), 8.30 (dd, 1H), 8.03 (d, 2H), 7.77 (s, 1H), 7.68 (m, 3H), 7.47 (dd, 1H), 7.39 (m, 2H), 7.33 (d, 1H), 7.06 (dd, 1H), 5.30 (s, 2H), 3.88 (s, 3H), 3.17 (m, 1H), 1.37 (d, 6H).

EXAMPLE 10

4-[3-(6-Isopropyl-quinolin-8-yl)-phenoxymethyl]-benzoic acid

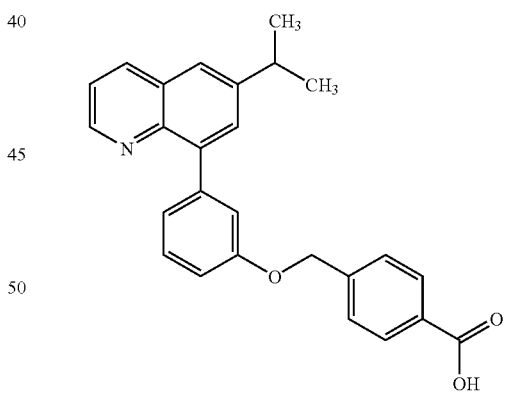

To a solution of the ester of EXAMPLE 9 (1.0 eq) in THF/MeOH (2/1; 0.1M) was added of aqueous solution of LiOH (1N; 5.0 eq). The resulting mixture was stirred 1 hour at 70° C., acidified to pH 5 using HCl (1N) and extracted with Et$_2$O (2×). The combined organic extracts were washed with brine, dried over MgSO$_4$, filtered and concentrated. Flash chromatography (Hex:EtOAc; 9:1 to 1:9 in 15 min) afforded the title compound as a white solid.

$^1$H NMR (400 MHz, acetone-d$_6$): δ 11.3 (s, OH), 8.80 (dd, 1H), 8.30 (dd, 1H), 8.06 (dd, 1H), 7.77 (d, 1H), 7.66 (m, 3H), 7.47 (dd, 1H), 7.38 (m, 2H), 7.30 (dd, 1H), 7.07 (ddd, 1H), 5.30 (s, 2H), 3.16 (m, 1H), 1.37 (d, 6H).

EXAMPLE 11

2-{4-[3-(6-Isopropyl-quinolin-8-yl)-phenoxymethyl]-phenyl}-propan-2-ol

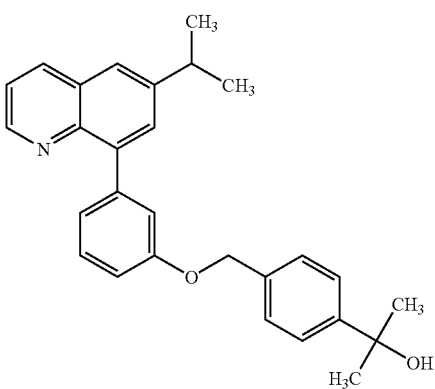

To a solution of the ester of EXAMPLE 9 (1.0 eq) in THF (0.05M) was added MeMgBr (3M in Et$_2$O; 5 eq). The resulting mixture was stirred 12 hours at room temperature, poured in saturated aqueous NH$_4$Cl and extracted with Et$_2$O (2×). The combined organic extracts were washed with brine, dried over MgSO$_4$, filtered and concentrated. Flash chromatography (Hex:EtOAc; 9:1 to 1:9 in 15 min) afforded the title compound an oil.

$^1$H NMR (400 MHz, acetone-d$_6$): δ 8.81 (dd, 1H), 8.30 (dd, 1H), 7.77 (d, 1H), 7.69 (d, 1H), 7.55 (d, 2H), 7.46 (m, 3H), 7.35 (m, 2H), 7.27 (d, 1H), 7.04 (dd, 1H), 5.16 (s, 2H), 3.17 (m, 1H), 1.51 (s, 6H), 1.37 (d, 6H).

EXAMPLE 12

8-[3-Fluoro-5-(4-methylsulfanyl-benzyloxy)-phenyl]-6-isopropyl-quinoline

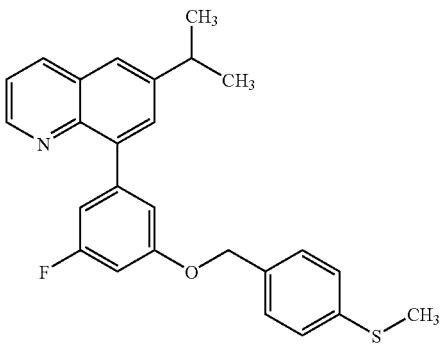

Step 1: 3-Bromo-5-fluoro-5-(4-methylsulfanyl-benzyloxy)-phenyl

To a solution of (4-Methylsulfanyl-phenyl)-methanol (1.0 eq) in DMF (1.0M) was added K-tBuO (1M in THF; 1 eq) followed by Bromo-3,5-difluoro-benzene (1.0 eq). The resulting mixture was stirred 12 hours at room temperature, poured in water and extracted with Et$_2$O (2×). The combined organic extracts were washed with brine, dried over MgSO$_4$, filtered and concentrated. Flash chromatography (Hex:EtOAc; 9:1 to 1:9) afforded the desired compound as a yellow solid.

Step 2: Example 12

The title compound was prepared in a two steps one-pot procedure. A mixture of the arylbromide from Step 1 (1.0 eq), diboron pinacole ester (1.8 eq), KOAc (3 eq) and PdCl$_2$(dppf)$_2$ (0.05 eq) in DME (0.2M) was stirred at 85° C. for 12 h. To the resulting mixture was added Quinoline 1 (1.0 eq) and Na$_2$CO$_3$ (2M in H$_2$O; 3 eq). The mixture was refluxed for 12 h, poured in H$_2$O and extracted with Et$_2$O (2×). The combined organic extracts were washed with brine, dried over MgSO$_4$, filtered and concentrated. Flash chromatography (Tol:EtOAc; 9:1) afforded the title compound as an oil.

$^1$H NMR (400 MHz, acetone-d$_6$); δ 8.82 (dd, 1H), 8.29 (dd, 1H), 7.78 (d, 1H), 7.72 (d, 1H), 7.47 (dd, 1H), 7.44 (d, 2H), 7.29 (d, 2H), 7.20 (dd, 1H), 7.12 (ddd, 1H), 6.8 (dt, 1H), 5.15 (s, 2H), 3.16 (m, 1H), 2.48 (s, 3H), 1.37 (d, 6H).

EXAMPLE 13

8-[3-Fluoro-5-(4-methanesulfonyl-benzyloxy)-phenyl]-6-isopropyl-quinoline

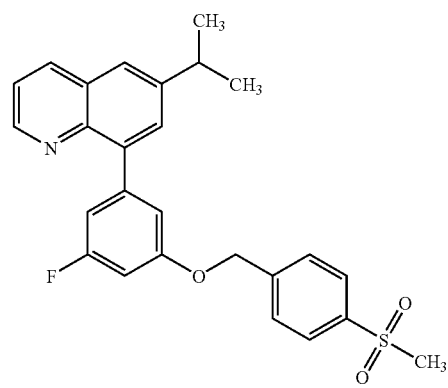

To a solution of the thioether from EXAMPLE 12 (1.0 eq) in THF/H$_2$O 5% (0.05M) was added NMO (4.0 eq) and a catalytic amount of OsO$_4$. The mixture was stirred 12 hours at room temperature, poured in saturated aqueous Na$_2$S$_2$O$_3$ and extracted with Et$_2$O (2×). The combined organic extracts were washed with brine, dried over MgSO$_4$, filtered and concentrated to afford the title compound as a foam.

$^1$H NMR (300 MHz, acetone-d$_6$): δ 8.82 (dd, 1H), 8.32 (d, 1H), 7.99 (d, 2H), 7.78–7.74 (m, 4H), 7.50 (dd, 1H), 7.24 (s, 1H), 7.13 (dt, 1H), 6.88 (dt, 1H), 5.38 (s, 2H), 3.18 (m, 1H), 3.13 (s, 3H), 1.38 (d, 6H).

EXAMPLE 14

8-(3-Benzyloxy-phenyl)-6-isopropyl-quinoline

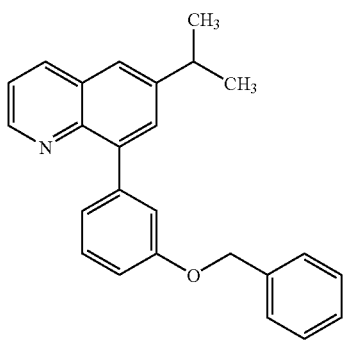

Prepared according to the procedure described in EXAMPLE 1 but using benzyl bromide as the starting material. The title compound was obtained as an oil.

$^1$H NMR (300 MHz, acetone-$d_6$): δ 8.78 (dd, 1H), 8.28 (dd, 1H), 7.76 (d, 1H), 7.65 (d, 1H), 7.51 (m, 3H), 7.36 (m, 6H), 7.04 (dd, 1H), 5.18 (s, 2H), 3.16 (m, 1H), 1.34 (d, 6H).

EXAMPLE 15

[3-(6-Isopropyl-quinolin-8-yl)-phenoxy]-phenyl-acetic acid methyl ester

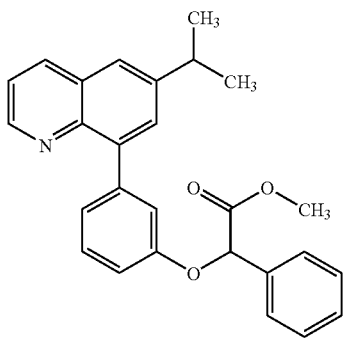

Prepared according to the procedure described in EXAMPLE 1 but using bromo-phenyl-acetic acid methyl ester as the starting material. Flash chromatography (Hex:EtOAc; 7:3) afforded the title compound as a foam.

$^1$H NMR (300 MHz, acetone-$d_6$): δ 8.80 (dd, 1H), 8.31 (dd, 1H), 7.77 (d, 1H), 7.66 (m, 3H), 7.50–7.31 (m, 7H), 7.01 (ddd, 1H), 5.92 (s, 1H), 3.71 (s, 3H), 3.17 (m, 1H), 1.37 (d, 6H).

EXAMPLE 16

1-[3-(6-Isopropyl-quinolin-8-yl)-phenoxy]-2-methyl-1-phenyl-propan-2-ol

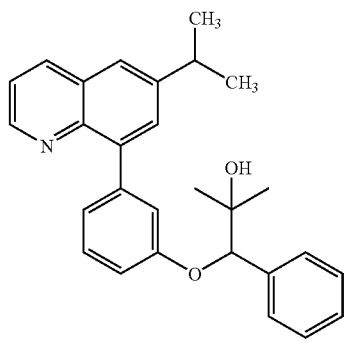

Prepared according to the procedure described in EXAMPLE 11 but using the ester of EXAMPLE 15 as the starting material. The title compound was obtained as a foam.

$^1$H NMR (300 MHz, acetone-$d_6$): δ 8.77 (dd, 1H), 8.28 (dd, 1H), 7.72 (d, 1H), 7.51 (m, 3H), 7.45 (dd, 1H), 7.35–7.19 (m, 6H), 6.93 (dt, 1H), 5.12 (s, 1H), 3.72 (s, OH), 3.12 (m, 1H), 1.33 (dd, 6H), 1.28 (d, 6H).

EXAMPLE 17

1-{3-[6-(1-Methanesulfonyl-1-methyl-ethyl)-quinolin-8-yl]-phenoxy}-1-(4-methanesulfonyl-phenyl)-2-methyl-propan-2-ol

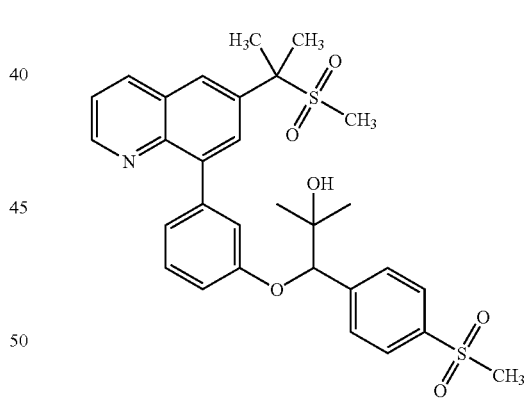

Step 1: 3-[6-(1-Methanesulfonyl-1-methyl-ethyl)-quinolin-8-yl]-phenol

A mixture of Quinoline 10 (1.0 eq), 3-(4,4,5,5-Tetramethyl-[1,3,2]dioxaborolan-2-yl)-phenol (0.84 eq), aqueous Na$_2$CO$_3$ (3.5 eq; 2M) and Pd(OAc)$_2$ (0.05 eq) and PPh$_3$ (0.12 eq) in n-propanol (0.26M) was refluxed for 6 h. The resulting mixture was poured in saturated aqueous NH$_4$Cl and extracted with EtOAc (2×). The combined organic extracts were washed with brine, dried over MgSO$_4$, filtered and concentrated. Flash chromatography (Tol:Ace; 8.5:1.5) and subsequent recrystallization in Tol/Ace/Et$_2$O afforded the desired compound as a yellow solid.

Step 2: Hydroxy-(4-methylsulfanyl-phenyl)-acetic acid ethyl ester

To a solution of (4-methylsulfanyl-phenyl)-oxo-acetic acid ethyl ester (Described in *J. Med. Chem.* 1981, 407) (1.0 eq) in EtOH (0.22M) at −78° C. was added NaBH$_4$ (0.5 eq). The resulting mixture was stirred for 30 min then quenched at −78° C. by adding saturated aqueous NH$_4$Cl. The residual mixture was concentrated, filtered on silica gel using EtOAc. The combined organic extracts were concentrated and the residual solid was recrystallised in Et$_2$O/Hex to afford the desired compound as a yellow solid.

Step 3: Chloro-(4-methylsulfanyl-phenyl)-acetic acid ethyl ester

To a solution of the hydroxy-(4-methylsulfanyl-phenyl)-acetic acid ethyl ester of Step 2 (1.0 eq) in CH$_2$Cl$_2$ (0.2M) was added SOCl$_2$ (5 eq). The resulting mixture was stirred at room temperature for 12 h, poured in saturated aqueous NH$_4$Cl and extracted with Et$_2$O (2×). The combined organic extracts were washed with brine, dried over MgSO$_4$, filtered and concentrated. Flash chromatography (Hex:EtOAc; 9.5:0.5) afforded the desired compound as a yellow solid.

Step 4: {3-[6-(1-Methanesulfonyl-1-methylethyl)-quinolin-8-yl]-phenoxy}-(4-methylsulfanyl-phenyl)-acetic acid ethyl ester Prepared according to the procedure described in EXAMPLE 1, but using the 3-[6-(1-methanesulfonyl-1-methylethyl)-quinolin-8-yl]-phenol from present Step 1 and the α-chloro ethyl ester from present Step 3 as the starting material. The {3-[6-(1-methanesulfonyl-1-methyl-ethyl)-quinolin-8-yl]-phenoxy}-(4-methylsulfanyl-phenyl)-acetic acid ethyl ester compound was obtained as a white solid.

Step 5: {3-[6-(1-Methanesulfonyl-1-methyl-ethyl)-quinolin-8-yl]-phenoxy}-(4-methanesulfonyl-phenyl)-acetic acid ethyl ester To a solution of the thioether of present Step 4 (1.0 eq) in THF/MeOH/H$_2$O (2/1/1; 0.2M) was added Oxone (2.1 eq). The resulting mixture was stirred at room temperature for 12 h, poured in saturated aqueous NaHCO$_3$ and extracted with Et$_2$O (2×). The combined organic extracts were washed with brine, dried over MgSO$_4$, filtered and concentrated. Flash chromatography (Hex:EtOAc; 7:3 to 3:2 in 15 min) afforded the desired compound as a white solid.

Step 6: Example 17

To solution of the {3-[6-(1-methanesulfonyl-1-methyl-ethyl)-quinolin-8-yl]-phenoxy}-(4-methanesulfonyl-phenyl)-acetic acid ethyl ester from present Step 5 (1.0 eq) in THF (0.1M) at −78° C. was added dropwise MeMgBr (3M in Et$_2$O; 3 eq). The resulting mixture was stirred at −78° C. for 1 h then extra MeMgBr (3M in Et$_2$O; 2 eq) was added. The final mixture was stirred at −78° C. for 2 h, poured in saturated aqueous NH$_4$Cl and extracted with Et$_2$O (2×). The combined organic extracts were washed with brine, dried over MgSO$_4$, filtered and concentrated. Flash chromatography (Hex:EtOAc; 4:1) afforded the title compound as a foam.

$^1$H NMR (400 MHz, acetone-d$_6$): δ 8.83 (dd, 1H), 8.41 (dd, 1H), 8.22 (d, 1H), 7.96 (d, 1H), 7.90 (d, 2H), 7.79 (d, 2H), 7.53 (dd, 1H), 7.27 (m, 3H), 6.98 (ddd, 1H), 5.27 (s, 1H), 3.95 (s, OH), 3.10 (s, 3H), 2.69 (s, 3H), 1.950 (s, 3H), 1.948 (s, 3H), 1.31 (s, 3H), 1.28 (s, 3H).

EXAMPLE 18

8-(3-Benzylsulfanyl-phenyl)-6-isopropyl-quinoline

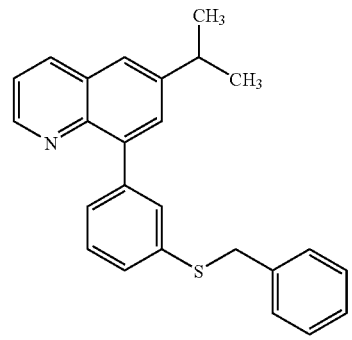

To solution of Quinoline 3 (1.0 eq) in THF (0.22M) at 0° C. was added NaH (60% suspension in oil; 1.5 eq). The resulting mixture was warmed to room temperature and stirred for 30 min. Benzyl bromide was then added (1.5 eq). The final mixture was stirred 4 h, poured in saturated aqueous NH$_4$Cl and extracted with EtOAc (2×). The combined organic extracts were washed with brine, dried over MgSO$_4$, filtered and concentrated. Flash chromatography (Hex:EtOAc; 8:1) afforded the title compound as a foam.

$^1$H NMR (300 MHz, acetone-d$_6$): δ 8.82 (dd, 1H), 8.29 (dd, 1H), 7.76 (d, 1H), 7.68 (d, 1H), 7.64 (d, 1H), 7.56 (m, 1H), 7.48 (q, 1H), 7.42 (d, 2H), 7.38 (d, 2H), 7.31 (t, 1H), 7.22 (d, 2H), 4.26 (s, 2H), 3.14 (m, 1H), 1.36 (d, 6H). LRMS (CI) 370 (M+H)$^+$

EXAMPLE 19

4-Azido-3-iodo-N-[3-(6-pyridin-4-ylmethyl-quinolin-8-yl)-phenyl]-benzamide

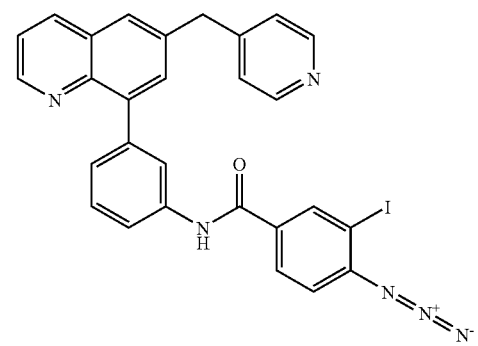

Step 1: 4-Amino-3-iodo-benzoic acid methyl ester

To solution of 4-Aminobenzoic acid (1.1 eq) in aqueous 1N HCl (0.7M) was added ICl (0.98 eq). The resulting mixture was stirred for 48 h, poured in saturated Na$_2$S$_2$O$_4$ and extracted with Et$_2$O (2×). The combined organic extracts were washed with water, brine, dried over Na$_2$SO$_4$, filtered. To the resulting Et$_2$O solution at 0° C. was added CH$_2$N$_2$ (solution in Et$_2$O) until the esterification was completed by TLC. After concentration, flash chromatography (Hex:EtOAc; 3:1) afforded the desired compound as a brown solid.

Step 2: 4-Azido-3-iodo-benzoic acid methyl ester

To a suspension of the 4-amino-3-iodo-benzoic acid methyl ester from Step 1 (1.0 eq) in water (0.36M) was added NaNO₂ (1.2 eq). The resulting mixture was cooled to 0° C. and aqueous HCl (6M; 2.5 eq) was added dropwise over 45 min. The mixture was stirred at 0° C. for 4 h, then NaN₃ (1.1) dissolved in water (1.0M) was added over 30 min. The final mixture was stirred at room temperature for 1 h and extracted with Et₂O (3×). The combined organic extracts were washed with brine, dried over MgSO₄, filtered and concentrated. Flash chromatography (Hex:EtOAc; 4:1) afforded the desired compound as a light brown solid.

Step 3: 4-Azido-3-iodo-benzoic acid

To a solution of the azido-ester from Step 2 (1.0 eq) in 6 mL of THF (0.2M) was added LiOH (2 N in H₂O; 1.5 eq). The resulting mixture was stirred at 50° C. for 4 h, then acidified to pH 4 using HCl (1N) and extracted with Et₂O (3×). The combined organic extracts were washed with water, brine, dried over MgSO₄, filtered and concentrated to afford the 4-azido-3-iodo-benzoic acid compound as a light yellow solid.

Step 4: Example 19

To a solution of Quinoline 9 (1.0 eq) in CH₂Cl₂ (0.05M) was added 1-Cyclohexyl-3-(2-morpholinoethyl)carbodiimide metho-p-toluenesulfonate (2.0 eq) then the 4-azido-3-iodo-benzoic acid of Step 3 (1.45 eq) and DMAP (0.1 eq). The resulting mixture was stirred for 24 h, poured in saturated aqueous NaHCO₃ and extracted with EtOAc (2×). The combined organic extracts were washed with brine, dried over MgSO4, filtered and concentrated. Flash chromatography (CH₂Cl₂:EtOAc; 1:4) afforded the title compound as a light brown solid.

¹H NMR (300 MHz, CDCl₃): δ 8.85 (dd, 1H), 8.52 (dd, 2H), 8.23 (s, 1H), 8.12 (d, 1H), 8.05 (s, 1H), 7.88 (s, 1H), 7.82 (dd, 1H), 7.74 (d, 1H), 7.55 (dd, 2H), 7.38 (m, 3H), 7.15 (d, 2H), 7.08 (d, 1H), 4.15 (s, 2H).

EXAMPLE 20

N-[3-(6-Pyridin-4-ylmethyl-quinolin-8-yl)-phenyl]-benzamide

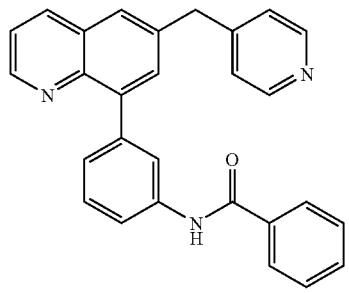

To a solution of Quinoline 9 (1.0 eq) in 4 mL of CH₂Cl₂ (0.06M) was added benzoyl chloride (1.0 eq). The mixture was stirred for 24 h, poured in saturated aqueous NaHCO₃ and extracted with CH₂Cl₂ (2×). The combined organic extracts were dried over Na₂SO₄, filtered and concentrated. Flash chromatography (EtOAc) and suspension-filtration sequence in Et₂O afforded the title compound as a light brown solid.

¹H NMR (300 MHz, CDCl₃): δ 8.88 (dd, 1H), 8.62 (dd, 2H), 8.14 (dd, 1H), 7.87 (t, 4H), 7.76 (d, 1H), 7.58 (s, 2H), 7.44 (m, 6H), 7.14 (d, 2H), 4.18 (s, 2H).

EXAMPLE 21

N-{3-[6-(1-Oxy-pyridin-4-ylmethyl)-quinolin-8-yl]-phenyl}-benzamide

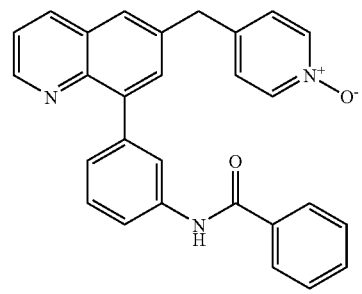

To solution of the quinoline from EXAMPLE 20 (1.0 eq) in CH₂Cl₂ (0.1M) was added 3-chloroperoxybenzoic acid (1.5 eq). The mixture was stirred at for 12 h, then poured in HCl (2N) and extracted with CH₂Cl₂ (2×). The combined organic extracts were dried over MgSO₄, filtered and concentrated. Flash chromatography (EtOAc:EtOH; 2:1) afforded the title compound as a white solid.

¹H NMR (400 MHz, CDCl₃): δ 8.92 (d, 1H), 8.15 (m, 3H), 7.96 (s, 1H), 7.84 (t, 3H), 7.68 (d, 1H), 7.52 (m, 6H), 7.43 (t, 2H), 7.12 (s, 2H), 4.16 (s, 2H).

EXAMPLE 22

N-[3-(6-Pyridin-4-ylmethyl-quinolin-8-yl)-phenyl]-benzenesulfonamide

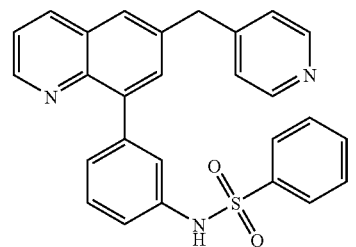

To solution of Quinoline 9 (1.0 eq) in CH₂Cl₂ (0.15M) was added benzene sulfonyl chloride (1.0 eq). The resulting mixture was stirred for 12 h, poured in Na₂CO₃, and extracted with EtOAc (2×). The combined organic extracts were dried over MgSO₄, filtered and concentrated. A suspension-filtration sequence in Et₂O afforded the title compound as a white solid.

¹H NMR (300 MHz, CDCl₃): δ 8.84 (dd, 1H), 8.53 (dd, 2H), 8.12 (dd, 1H), 7.82 (d, 2H), 7.57 (s, 1H), 7.48 (d, 1H), 7.42 (m, 6H), 7.36 (t, 1H), 7.14 (d, 2H), 7.04 (d, 1H), 6.64 (s, 1H), 4.14 (s, 2H).

EXAMPLE 23

Thiophene-2-sulfonic acid [3-(6-pyridin-4-ylmethyl-quinolin-8-yl)-phenyl]-amide

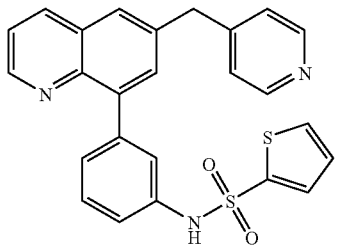

Prepared according to the procedure described in EXAMPLE 22, but using thiophene-2-sulfonyl chloride as the starting, material. Flash chromatography (EtOAc) afforded the title compound as a white solid.

$^1$H NMR (300 MHz, CDCl$_3$): δ 8.86 (dd, 1H), 8.52 (d, 2H), 8.12 (d, 1H), 7.58 (s, 1H), 7.44 (m, 8H), 7.16 (d, 2H), 7.13 (d, 1H), 6.96 (t, 1H), 4.18 (s, 2H).

EXAMPLE 24

N-{3-[6-(1-Oxy-pyridin-4-ylmethyl)-quinolin-8-yl]-phenyl}-benzenesulfonamide

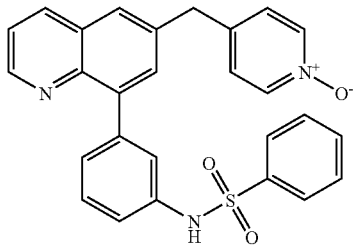

Prepared according to the procedure described in EXAMPLE 21, but using the quinoline of EXAMPLE 22 as the starting material. The title compound (white solid) precipitated out of the reaction mixture and was isolated by filtration.

$^1$H NMR (300 MHz, DMSO-d$_6$): δ 10.3 (s, 1H) 8.82 (d, 1H), 8.36 (d, 1H), 8.14 (d, 2H), 7.81 (d, 3H), 7.58 (m, 4H), 7.48 (s, 1H), 7.34 (m, 5H), 7.12 (d, 1H), 4.16 (s, 2H).

EXAMPLE 25

Benzenesulfonic acid 3-(6-isopropyl-quinolin-8-yl)-phenyl ester

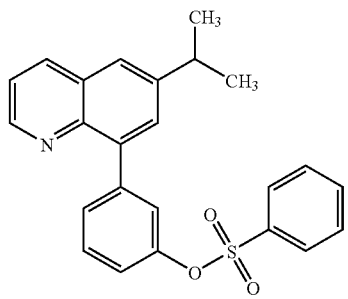

To solution of Quinoline 2 (1.5 eq) in THF (0.2M) was added NaH (1.5 eq) the after 20 min, benzenesulfonyl chloride (1.5 eq) was added. The mixture was stirred for 12 h, poured in saturated aqueous NH$_4$Cl and extracted with EtOAc (2×). The combined organic extracts were washed with brine, dried over MgSO$_4$, filtered and concentrated. Flash chromatography (Hex:EtOAc; 4:1) afforded the title compound as a white solid.

$^1$H NMR (300 MHz, CDCl$_3$): δ 8.78 (dd, 1H), 8.28 (dd, 1H), 7.94 (dd, 2H), 7.82 (d, 2H), 7.68 (t, 3H), 7.56 (d, 1H), 7.46 (m, 2H), 7.35 (d, 1H), 7.12 (dd, 1H), 3.13 (m, 1H), 1.37 (d, 6H). LRMS (CI) 404 (M+H)$^+$

EXAMPLE 26

Benzenesulfonic acid 3-[6-(1-hydroxy-1-methyl-ethyl)-quinolin-8-yl]-phenyl ester

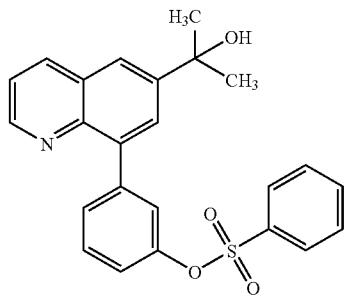

To solution of KBrO$_3$ (1.1 eq) in 5 mL of dioxane/water (3/2; 0.14M) was added the quinoline of EXAMPLE 25 (1.0 eq) and CAN (0.1 eq). The mixture was stirred at 75° C. for 16 h, poured in saturated aqueous NH$_4$Cl and extracted with CH$_2$Cl$_2$ (2×). The combined organic extracts were dried over MgSO$_4$, filtered and concentrated. Flash chromatography (Hex:EtOAc; 1:1) afforded the title compound as a white solid.

$^1$H NMR (300 MHz, CDCl$_3$): δ 8.81 (dd, 1H), 8.36 (dd, 1H), 8.08 (d, 1H), 7.93 (dd, 2H), 7.85 (d, 1H), 7.81 (t, 1H), 7.68 (t, 3H), 7.52 (q, 1H), 7.46 (dd, 1H), 7.38 (d, 1H), 7.11 (dd, 1H), 4.28 (s, 1H), 1.63 (s, 6H). LRMS (CI) 420 (M+H)$^+$

EXAMPLE 27

Propane-2-sulfonic acid [3-(6-isopropyl-quinolin-8-yl)-benzyl]-(4-methylsulfanyl-phenyl)-amide

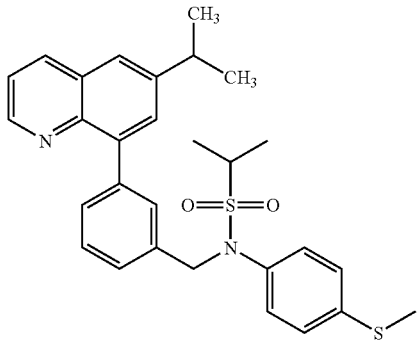

Step 1: Propane-2-sulfonic acid (4-methylsulfanyl-phenyl)-amide

To solution of 4-methylsulfanyl-phenylamine (1.1 eq) in pyridine (1.3M) at 0° C. was added iso-propylsulfonyl chloride (1.5 eq). The mixture was stirred at room temperature for 12 h, poured in HCl (1N) and extracted with EtOAc. The combined organic extracts were washed with HCl (1N; 2×), water (2×), brine, dried over $Na_2SO_4$, filtered and concentrated. Flash chromatography (Hex:EtOAc 0 to 50% in 15 min) and a suspension-filtration sequence in Hex/$CH_2Cl_2$ afforded the desired compound as a white solid.

Step 2: Example 27

A mixture of the sulfonamide from Step 1 (1.05 eq), Quinoline 20 (1.0 eq) and $Cs_2CO_3$ (3.0 eq) were combined in DMF (0.2M), stirred for 2 h, quenched using excess of AcOH and extracted with $Et_2O$ (2×). The combined organic extracts were washed with water (3×), brine, dried over $MgSO_4$, filtered and concentrated. Flash chromatography (Hex:EtOAc; 0 to 50% in 15 min) afforded the title compound as a foam.

$^1$H NMR (400 MHz, acetone-$d_6$): δ 8.82 (dd, 1H), 8.30 (dd, 1H), 7.76 (s, 1H), 7.67 (s, 1H), 7.59–7.57 (m, 2H), 7.49–7.44 (m, 3H), 7.36 (t, 1H), 7.31 (d, 1H), 7.21 (dd, 2H), 5.06 (s, 2H), 3.37 (sept, 1H), 3.16 (sept, 1H), 2.44 (s, 3H), 1.38 (d, 6H), 1.37 (d, 6H).

LRMS (CI) 505 (M+H)$^+$

EXAMPLE 28

4-Fluoro-N-[3-(6-isopropyl-quinolin-8-yl)-benzyl]-N-(4-methylsulfanyl-phenyl)-benzenesulfonamide

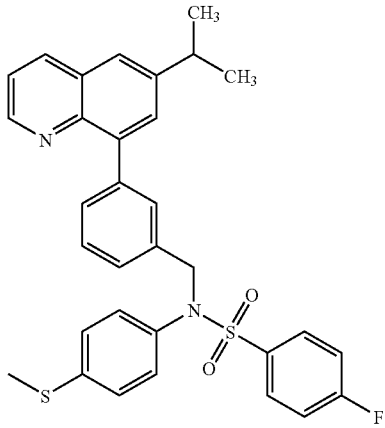

Step 1: 4-Fluoro-N-(4-methylsulfanyl-phenyl)-benzenesulfonamide

Prepared according to the procedure described in EXAMPLE 27 (Step 1) but using 4-fluoro-benzenesulfonyl chloride as the starting material. A suspension-filtration sequence in Hex/$CH_2Cl_2$ afforded the desired compound as a white solid.

Step 2: Example 28

Prepared according to the procedure described in EXAMPLE 27 but using the sulfonamide of Step 1 as the starting material. The title compound was obtained as a white solid by a suspension-filtration sequence in Hex/$CH_2Cl_2$.

$^1$H NMR (400 M, acetone-$d_6$): δ 8.80 (dd, 1H), 8.31 (dd, 1H), 7.79–7.75 (m, 3H), 7.64 (s, 1H), 7.58–7.56 (m, 2H), 7.48 (dd, 1H), 7.38–7.30 (m, 4H), 7.16 (dd, 2H), 7.12 (dd, 2H), 4.92 (s, 2H), 3.16 (sept, 1H), 2.43 (s, 3H), 1.36 (s, 6H).

LRMS (CI) 557 (M+H)$^+$

EXAMPLE 29

4-Fluoro-N-[3-(6-isopropyl-quinolin-8-yl)-benzyl]-N-(4-methanesulfonyl-phenyl)-benzenesulfonamide

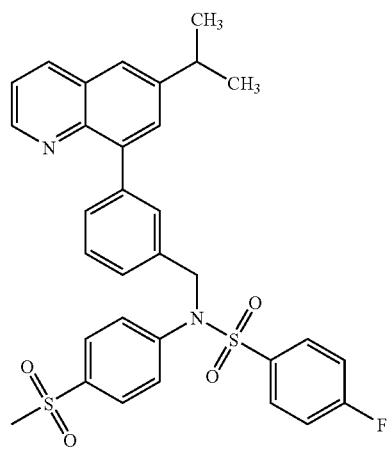

Prepared according to the procedure described in EXAMPLE 13, but using EXAMPLE 28 as the starting material. Flash chromatography (Hex:EtOAc; 0 to 70%) afforded the title compound as a white solid.

$^1$H NMR (400 MHz, acetone-$d_6$): δ 8.81 (dd, 1H), 8.28 (dd, 1H), 7.88 (dd, 2H), 7.81–7.73 (m, 4H), 7.60–7.55 (dd, 4H), 7.46 (dd, 1H), 7.37–7.33 (m, 4H), 5.05 (s, 2H), 3.14 (sept, 1H), 3.06 (s, 3H), 1.35 (dd, 6H).

EXAMPLE 30

Cyclopropylmethyl-[3-(6-isopropyl-quinolin-8-yl)-benzyl]-(4-methanesulfonyl-phenyl)-amine

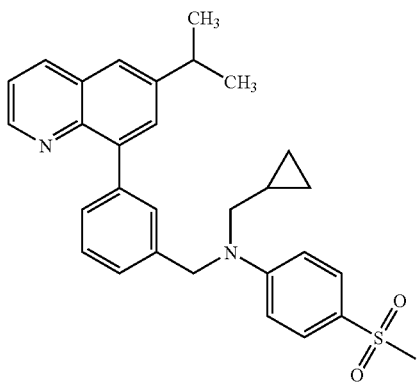

Step 1: [3-(6-Isopropyl-quinolin-8-yl)-benzyl]-(4-methylsulfanyl-phenyl)-amine A mixture of Quinoline 5 (1.1 eq) and 4-methylsulfanyl-phenylamine (1.15 eq) in EtOH (0.18M) was refluxed for 12 h. The mixture was cooled down to room temperature, An equi volume of Hex was added and the resulting precipitate (imine) was solated by filtration. The imine was suspended in MeOH (0.4M), $NaBH_3CN$ (1.8 eq) was added followed by TFA (2.0 eq). The resulting mixture was stirred for 1 h, poured in saturated aqueous $NaHCO_3$ and extracted with EtOAc (2×). The combined organic extracts were washed with brine, dried over $Na_2\ _{SO4}$, filtered and concentrated. Flash chromatography (Hex:EtOAc; 4:1) afforded the desired compound as a light brown foam.

Step 2: [3-(6-Isopropyl-quinolin-8-yl)-benzyl]-(4-methanesulfonyl-phenyl)-amine Prepared according to the procedure described in EXAMPLE 17 (Step 5) but using the previous amine from Step 1 as the starting material. Flash chromatography (Tol:Ace; 4:1) afforded the desired compound as a foam.

Step 3: Example 30

To solution of the previous amine from step 2 (1.1 eq) in DMF (0.12M) was added NaH (60% dispersion in oil; 3.0 eq). The mixture was stirred for 15 min, then cyclopropyl-methyl bromide was added (1.2 eq). The final mixture was stirred for 12 h, quenched with AcOH, poured in water and extracted with $Et_2O$. The combined organic extracts were washed with water (2×), brine, dried over $Na_2\ _{SO4}$, filtered and concentrated. Flash chromatography (Tol:Ace; 9:1) afforded the title compound as a foam.

$^1$H NMR (500 MHz, acetone-$d_6$): δ 8.77 (dd, 1H), 8.28 (d, 1H), 7.75 (s, 1H), 7.66–7.60 (m, 5H), 7.45 (dd, 1H), 7.41 (t, 1H), 7.27 (d, 1H), 6.93 (d, 2H), 4.89 (s, 2H), 3.53 (d, 2H), 3.13 (sept, 1H), 2.94 (s, 3H), 1.34 (d, 6H), 1.25–1.23 (s, 1H), 0.54 (d, 2H), 0.36 (d, 2H).

LRMS (CI) 485 (M+H)$^+$

EXAMPLE 31

Propane-2-sulfonic acid [3-(6-isopropyl-quinolin-8-yl)-benzyl-(4-methanesulfonyl-phenyl)-amide

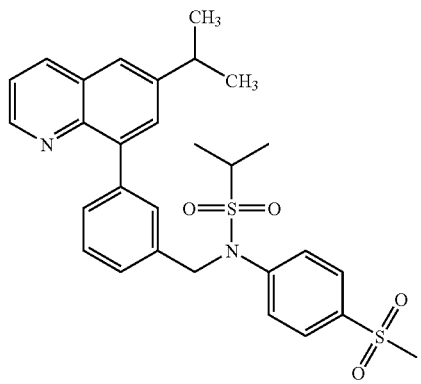

Prepared according to the procedure described in EXAMPLE 13 but using EXAMPLE 27 as the starting material. Flash chromatography (Hex:EtOAc; 10 to 100%) afforded the title compound as a white solid.

$^1$H NMR (500 MHz, acetone-$d_6$): δ 8.82 (dd, 1H), 8.29 (d, 1H), 7.90 (d, 2H), 7.84 (d, 2H), 7.76 (d, 2H), 7.62 (s, 1H), 7.57 (d, 1H), 7.46 (dd, 1H), 7.37 (t, 1H), 7.34 (d, 1H), 5.23 (s, 2H), 3.50 (sept, 1H), 3.15 (sept, 1H), 3.07 (s, 3H), 1.38 (d, 6H), 1.36 (d, 6H).

LRMS (CI) 537 (M+H)$^+$

EXAMPLE 32

N-[3-(6-Cyclopropyl-quinolin-8-yl)-benzyl]-N-(4-methanesulfonyl-phenyl)-C-phenyl-methanesulfonamide

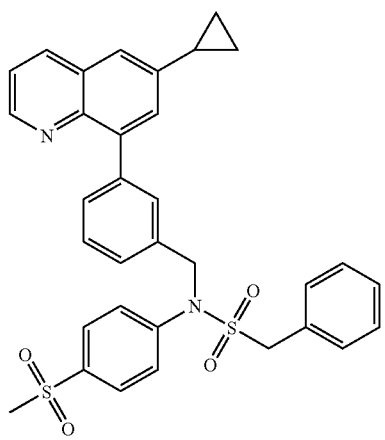

Prepared according to the procedure described in EXAMPLE 27 for the first two steps using benzylsulfonyl chloride and Quinoline 16 as the starting materials and the procedure described in EXAMPLE 13 for the oxidation step. Flash chromatography (Hex:EtOAc; 1:1) afforded the title compound as a white solid.

$^1$H NMR (500 MHz, acetone-$d_6$): δ 8.75 (dd, 1H), 8.23 (dd, 1H), 7.85 (dd, 2H), 7.69 (s, 1H), 7.65–7.61 (m, 3H), 7.55 (d, 1H), 7.47 (dd, 1H), 7.44 (dd, 1H), 7.39 (d, 1H), 7.37–7.34 (m, 4H), 7.29 (d, 1H), 5.03 (s, 2H), 4.68 (s, 2H), 3.07 (s, 3H), 2.17–2.13 (m, 1H), 1.08–1.04 (m, 2H), 0.88–0.84 (m, 2H). LRMS (CD) 583 (M+H)+

EXAMPLE 33

2-Phenyl-ethenesulfonic acid [3-(6-cyclopropyl-quinolin-8-yl)-benzyl]-(4-methanesulfonyl-phenyl)-amide

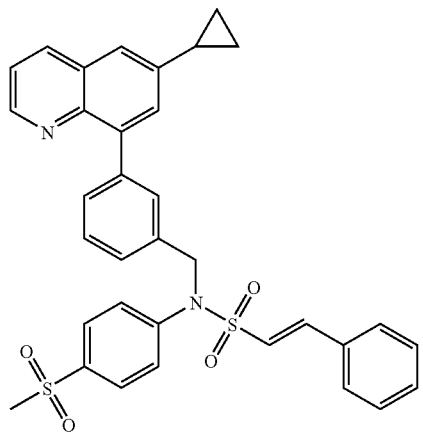

Prepared according to the procedure described in EXAMPLE 27 for the first two steps using 2-phenyl-ethenesulfonyl chloride and Quinoline 16 as the starting materials and the procedure described in EXAMPLE 13 for the oxidation step. A suspension-filtration sequence in Tol/Hex afforded the title compound as a white solid.

1H NMR (500 MHz, acetone-$d_6$): δ 8.77 (dd, 1H), 8.25 (dd, 1H), 7.90 (d, 2H), 7.78 (d, 2H), 7.77 (d, 1H), 7.69 (d, 1H), 7.56 (dd, 1H), 7.49–7.32 (m, 9H), 5.12 (s, 2H), 3.08 (s, 3H), 2.19–2.14 (m, 1H), 1.10–1.06 (m, 2H), 0.89–0.85 (m, 2H).

LRMS (CI) 596 (M+H)+

EXAMPLE 34

Thiophene-2-sulfonic acid [3-(6-cyclopropyl-quinolin-8-yl)-benzyl]-(4-methanesulfonyl-phenyl)-amide

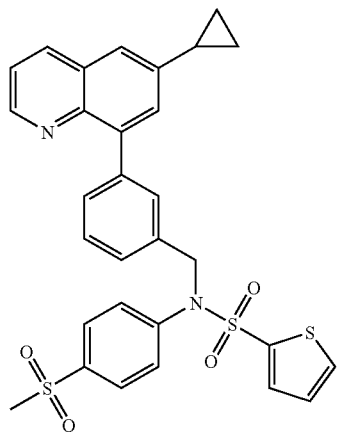

Prepared according to the procedure described in EXAMPLE 27 for the first two steps using thiophene-2-sulfonyl chloride and Quinoline 16 as the starting materials and the procedure described in EXAMPLE 13 for the oxidation step. Flash chromatography (Hex:EtOAc; 1:1 then 1:2) afforded the title compound as a white solid.

1H NMR (500 MHz, acetone-$d_6$): δ 8.78 (dd, 1H), 8.23 (dd, 1H), 7.96 (dd, 1H), 7.90 (dd, 2H), 7.71 (s, 1H), 7.62–7.54 (m, 5H), 7.45 (dd, 1H), 7.40 (d, 1H), 7.35–7.34 (m, 2H), 7.24 (dd, 1H), 5.06 (s, 2H), 3.08 (s, 3H), 2.19–2.13 (m, 1H), 1.09–1.05 (m, 2H), 0.88–0.85 (m, 2H). LRMS (CI) 575 (M+H)+

EXAMPLE 35

Butane-1-sulfonic acid [3-(6-cyclopropyl-quinolin-8-yl)-benzyl]-(4 methanesulfonyl-phenyl)-amide

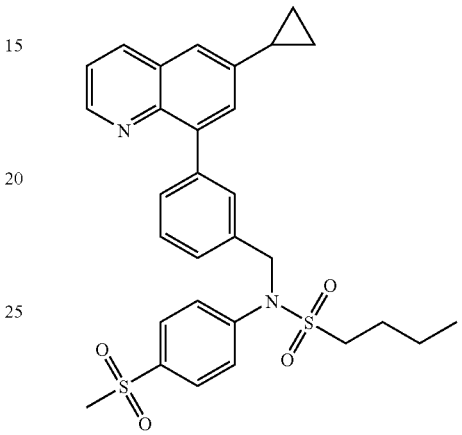

Prepared according to the procedure described in EXAMPLE 27 for the first two steps using butane-1-sulfonyl chloride and Quinoline 16 as the starting materials and the procedure described in EXAMPLE 13 for the oxidation step. Flash chromatography (Hex:EtOAc; 1:1) afforded the title compound as a white solid. 1H NMR (500 MHz, acetone-$d_6$): δ 8.78 (dd, 1H), 8.22 (dd, 1H), 7.91 (dd, 2H), 7.80 (dd, 2H), 7.74 (s, 1H), 7.61 (d, 1H), 7.56 (dt, 1H), 7.44 (dd, 1H), 7.41 (d, 1H), 7.38–7.33 (m, 2H), 5.18 (s, 2H), 3.29 (t, 2H), 3.07 (s, 3H), 2.17–2.13 (m, 1H), 1.85–1.79 (m, 2H), 1.46–1.42 (m, 2H), 1.09–1.04 (m, 2H), 0.89 (t, 3H), 0.87–0.84 (m, 2H). LRMS (CI) 550 (M+H)+

EXAMPLE 36

5-Methyl-isoxazole-3-carboxylic acid {3-[6-(cyano-dimethyl-methyl)-quinolin-8-yl]-benzyl}-(4-methanesulfonyl-phenyl)-amide

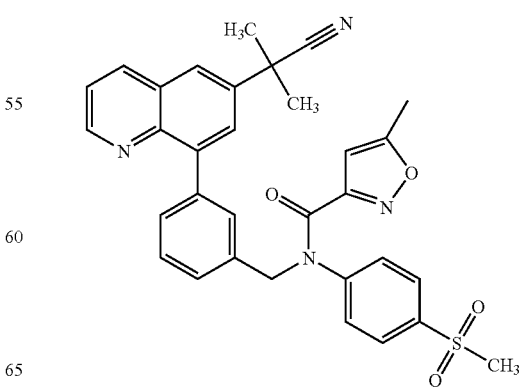

Step 1: 2-(8-{3-[(4-Methanesulfonyl-phenylamino)-methyl]-phenyl}-quinolin-6-yl)-2-methyl-propionitrile.

A mixture of Quinoline 19 (1.0 eq), 4-Methylsulfanyl-phenylamine (1.1 eq) in EtOH (0.12M) was refluxed for 12 h. The mixture was cooled down to room temperature and concentrated. The residue was suspended in MeOH (0.03M) and NaBH$_3$CN (4.0 eq) was added followed by of AcOH (0.5 eq). The resulting mixture was stirred for 12 h, poured in saturated aqueous NaHCO$_3$ and extracted with EtOAc (2×). The combined organic extracts were washed with brine, dried over Na$_2$SO$_4$, filtered and concentrated. Flash chromatography (Hex:EtOAc:NEt$_3$; 4:1:0.1) afforded the desired compound as a light brown foam.

Step 2: 5-Methyl-isoxazole-3-carboxylic acid {3-[6-(cyano-dimethyl-methyl)-quinolin-8-yl]-benzyl}-(4-methylsulfanyl-phenyl)-amide A mixture of the amine from Step 1 (1.0 eq) and 5-methyl-isoxazole-3-carbonyl chloride (1.8 eq) in pyridine (0.35M) was stirred for 12 h, poured in saturated aqueous NaHCO$_3$ and extracted with EtOAc (2×). The combined organic extracts were washed with brine, dried over MgSO$_4$, filtered and concentrated. Flash chromatography (Hex:EtOAc; 3:2) afforded the desired compound as a foam.

Step 3: Example 36

Prepared according to the procedure described in EXAMPLE 13 but using the thioether from step 2 as the starting material. Flash chromatography (Hex:EtOAc; 1:2) and suspension-filtration sequence in Hex/EtOAc afforded the title compound as a white solid.

$^1$H NMR (500 MHz, acetone-d$_6$): δ 8.93 (dd, 1H), 8.46 (dd, 1H), 8.11 (d, 1H), 7.90–7.88 (m, 3H), 7.80 (s, 1H), 7.63–7.61 (m, 3H), 7.58 (dd, 1H), 7.48 (t, 1H), 7.37 (d, 1H), 6.27 (s, 1H), 5.32 (s, 2H), 3.08 (s, 3H), 2.34 (s, 3H), 1.88 (s, 6H).

LRMS (CI) 565 (M+H)$^+$

EXAMPLE 37

2-[8-{3-([(4-Fluoro-benzyl)-(4-methanesulfonyl-phenyl)-amino]-methyl}-phenyl)-quinolin-6-yl]-2-methyl-propionitrile

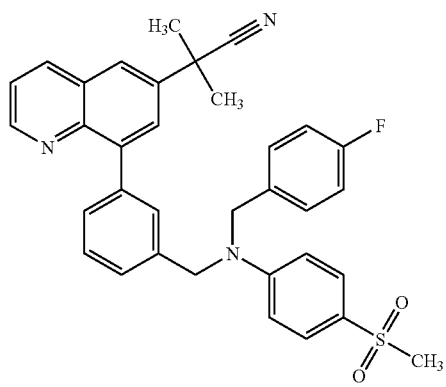

Step 1: 2-[8-(3-{[(4-Fluoro-benzyl)-(4-methylsulfanyl-phenyl)-amino]-methyl}-phenyl)-quinolin-6-yl]-2-methyl-propionitrile To solution of 2-(8-{3-[(4-Methanesulfonyl-phenylamino)-methyl]-phenyl}-quinolin-6-yl)-2-methyl-propionitrile from EXAMPLE 36 (Step 1) (1.0 eq) in DMF (0.2M) was added NaH (60% dispersion in oil; 4.0 eq). The resulting mixture was stirred for 10 min then 4-fluorobenzyl bromide (3.0 eq) was added. The mixture was stirred for 12 h, poured in saturated aqueous NH$_4$Cl and extracted with EtOAc (2×). The combined organic extracts were washed with brine, dried over MgSO$_4$, filtered and concentrated. Flash chromatography (Hex:EtOAc; 4:1) afforded the desired compound as a foam.

Step 2: Example 37

Prepared according to the procedure described in EXAMPLE 13 but using the 2-[8-(3-{[(4-fluoro-benzyl)-(4-methylsulfanyl-phenyl)-amino]-methyl}-phenyl)-quinolin-6-yl]-2-methyl-propionitrile thioether from Step 1 as the starting material. Flash chromatography (Hex:EtOAc; 1:1) followed by a suspension-filtration sequence in Hex/EtOAc afforded the title compound as a white solid.

$^1$H NMR (400 MHz, acetone-d$_6$): δ 8.67 (dd, 1H), 8.41 (dd, 1H), 8.09 (d, 1H), 7.90 (d, 1H), 7.69–7.63 (m, 4H), 7.53 (dd, 1H), 7.46 (t, 1H), 7.35–7.31 (m, 3H), 7.09 (t, 2H), 6.92 (d, 2H), 4.92 (s, 2H), 4.86 (s, 2H), 2.95 (s, 3H), 1.85 (s, 6H).

LRMS (CI) 564 (M+H)$^+$

EXAMPLE 38

{3-[6-(Cyano-dimethyl-methyl)-quinolin-8-yl]-benzyl}-(4-methanesulfonyl-phenyl)-carbamic acid isopropyl ester

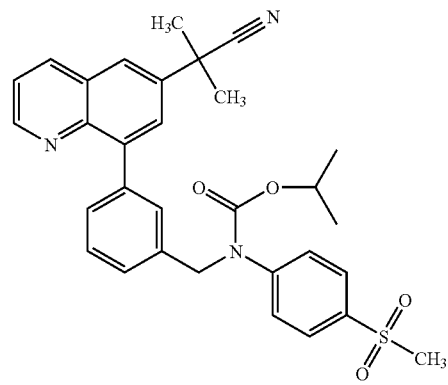

Step 1: {3-[6-(Cyano-dimethyl-methyl)-quinolin-8-yl]-benzyl 1-(4-methylsulfanyl-phenyl)-carbamic acid isopropyl ester To solution of 2-(8-{3-[(4-methanesulfonyl-phenylamino)-methyl]-phenyl}-quinolin-6-yl)-2-methyl-propionitrile from EXAMPLE 36, Step 1 (1.0 eq) in pyridine (0.3M) was added iso-propyl chloroformate (11 eq). The resulting mixture was stirred at 60° C. for 10 h, poured in saturated aqueous NaHCO$_3$ and extracted with EtOAc (2×). The combined organic extracts were washed with brine, dried over MgSO₄, filtered and concentrated. Flash chromatography (Hex:EtOAc; 2:1) afforded the desired compound as a foam.

Step 2: Example 38

Prepared according to the procedure described in EXAMPLE 13 but using the {3-[6-(cyano-dimethyl-methyl)-quinolin-8-yl]-benzyl}-(4-methylsulfanyl-phenyl)-carbamic acid isopropyl ester from Step 1 as the starting material. Flash chromatography (Hex:EtOAc; 1:2) afforded the title compound as a foam.

$^1$H NMR (400 MHz, acetone-$d_6$): δ 8.91 (dd, 1H), 8.44 (dd, 1H), 8.10 (d, 1H), 7.91–7.87 (m, 3H), 7.73–7.67 (m, 3H), 7.62 (d, 1H), 7.56 (dd, 1H), 7.42 (t, 1H), 7.33 (d, 1H), 5.14 (s, 2H), 4.98 (sept, 1H), 2.98 (s, 3H), 1.89 (s, 6H), 1.20 (d, 6H).

EXAMPLE 39

[{3-[6-(Cyano-dimethyl-methyl)-quinolin-8-yl]-benzyl}-(4-methanesulfonyl-phenyl)-amino]-acetic acid

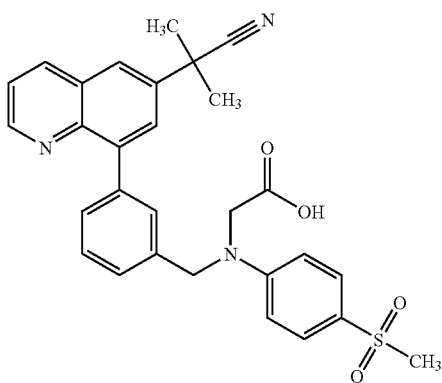

Step 1: [{3-[6-(Cyano-dimethyl-methyl)-quinolin-8-yl]-benzyl 1-(4-methylsulfanyl-phenyl)-amino]-acetic acid ethyl ester Prepared according to the procedure described in EXAMPLE 37 (Step 1) but using bromoacetic acid ethyl ester as the starting material. Flash chromatography (Hex:EtOAc; 2:1) afforded the desired compound as a foam.

Step 2: Example 39

Prepared according to the procedure described in EXAMPLE 13 but using the previous [{3-[6-(cyano-dimethyl-methyl)-quinolin-8-yl]-benzyl}-(4-methylsulfanyl-phenyl)-amino]-acetic acid ethyl ester from Step 1 as the starting material. Flash chromatography (Hex:EtOAc; 1:2) afforded the corresponding ethyl ester. The ester was hydrolyzed in THF/MeOH/LiOH 1N (2/1/1) for 12 h, poured in saturated aqueous NH₄Cl and extracted with EtOAc (2×). The combined organic extracts were washed with brine, dried over MgSO₄, filtered and concentrated. A suspension-filtration sequence in H/EtOAc afforded the title compound as a white solid.

$^1$H NMR (400 MHz, acetone-$d_6$): δ 8.89 (dd, 1H), 8.44 (dd, 1H), 8.10 (d, 1H), 7.91 (d, 1H), 7.74 (s, 1H), 7.70–7.66 (m, 3H), 7.55 (dd, 1H), 7.47 (t, 1H), 7.40 (d, 1H), 6.90 (d, 2H), 4.89 (s, 2H), 4.43 (s, 2H), 2.97 (s, 3H), 1.86 (s, 6H).

EXAMPLE 40

N-{3-[6-(Cyano-dimethyl-methyl)-quinolin-8-yl]-benzyl}-N-(4-methanesulfonyl-phenyl)-benzamide

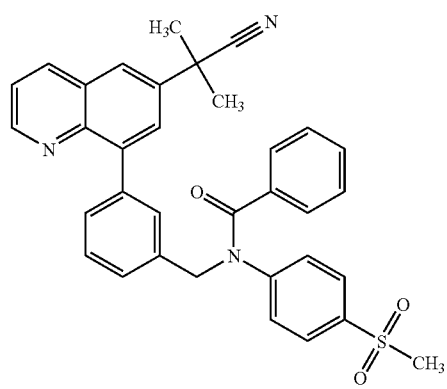

Prepared according to the procedure described in EXAMPLE 36 (Step 2 and 3) but using 2-(8-{3-[(4-methanesulfonyl-phenylamino)-methyl]-phenyl}-quinolin-6-yl)-2-methyl-propionitrile and benzoyl chloride as the starting materials.

$^1$H NMR (400 MHz, acetone-$d_6$): δ 8.90 (dd, 1H), 8.46 (dd, 1H), 8.11 (d, 1H), 7.90 (d, 1H), 7.85 (s, 1H), 7.78 (d, 2H), 7.60 (m, 2H), 7.51 (d, 2H), 7.41 (m, 4H), 7.31 (m, 1H), 7.24 (m, 2H), 5.35 (s, 2H), 3.02 (s, 3H), 1.88 (s, 6H).

EXAMPLE 41

1-{3-[6-(Cyano-dimethyl-methyl)-quinolin-8-yl]-benzyl}-3-ethyl-1-(4-methanesulfonyl-phenyl)-urea

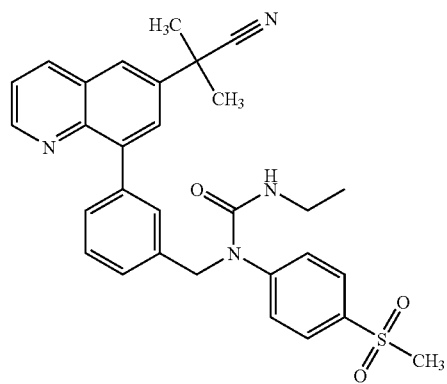

Step 1: 1-{3-[6-(Cyano-dimethyl-methyl)-quinolin-8-yl]-benzyl}-3-ethyl-1-(4-methylsulfanyl-phenyl)-urea To solution of 2-(8-{3-[(4-methanesulfonyl-phenylamino)-methyl]-phenyl}-quinolin-6-yl)-2-methyl-propionitrile from EXAMPLE 36 (Step 1) (1.0 eq) in 2 mL of THF (0.17M) was added DBU (1.1 eq) and ethyl-isocyanate (8.3 eq). The resulting mixture was stirred at 60° C. for 12 h, poured in saturated aqueous NaHCO₃ and extracted with EtOAc (2×). The combined organic extracts were washed with brine, dried over MgSO₄, filtered and concentrated. Flash chromatography (CH₂Cl₂:EtOAc; 4:1) afforded a contaminated sample of the desired compound as a oil. It was used as such in the next step.

Step 2: Example 41

Prepared according to the procedure described in EXAMPLE 17 (Step 5) but using the 1-{3-[6-(cyano-dimethyl-methyl)-quinolin-8-yl]-benzyl)-3-ethyl-1-(4-methylsulfanyl-phenyl)-urea of present Step 1 as the starting material. Flash chromatography (CH₂Cl₂:EtOAc; 3:2) afforded the title compound as a foam.

¹H NMR (400 MHz, acetone-d₆): δ 8.92 (dd, 1H), 8.45 (dd, 1H), 8.10 (d, 1H), 7.87 (m, 3H), 7.72 (s, 1H), 7.60 (m, 4H), 7.41 (t, 1H), 7.35 (d, 1H), 5.94 (brt, 1H), 5.11 (s, 2H), 3.20 (q, 2H), 3.06 (s, 3H), 1.88 (s, 6H), 1.01 (t, 3H).

EXAMPLE 42

1-{3-[6-(Cyano-dimethyl-methyl)-quinolin-8-yl]-benzyl}-3-isopropyl-1-(4 methanesulfonyl-phenyl)-urea

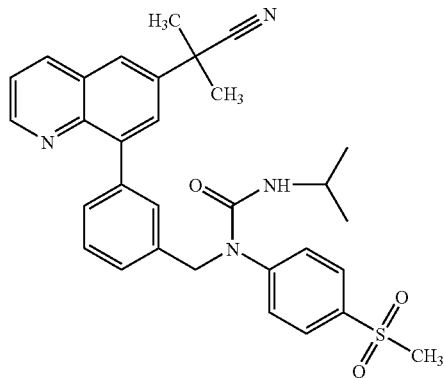

Prepared according to the procedure described in EXAMPLE 41 but using iso-propyl-isocyanate as the starting material. A suspension-filtration sequence on the residue from the oxidation step in Hex/EtOAc 10% afforded the title compound as a white solid.

¹H NMR (400 MHz, acetone-d₆): δ 8.92 (dd, 1H), 8.45 (dd, 1H), 8.12 (d, 1H), 7.88 (m, 3H), 7.72 (s, 1H), 7.60 (m, 4H), 7.42 (t, 1H), 7.35 (d, 1H), 5.72 (brd, 1H), 5.12 (s, 2H), 3.97 (m, 1H), 3.07 (s, 3H), 1.88 (s, 6H), 1.05 (d, 6H).

EXAMPLE 43

1.13-[6-(Cyano-methyl-methyl)-quinolin-8-yl]-benzyl]-1-(4-methanesulfonyl-phenyl)-3-phenyl-urea

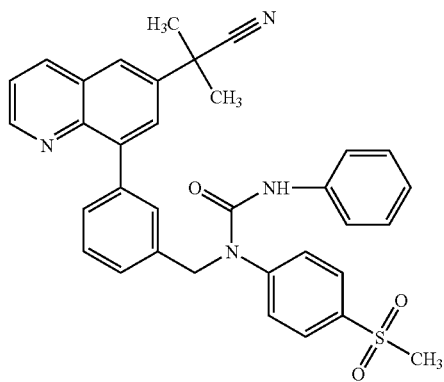

Prepared according to the procedure described in EXAMPLE 41 but using phenyl-isocyanate as the starting material. A suspension-filtration sequence on the residue from the oxidation step in Hex/EtOAc 10% afforded the title compound as a white solid.

¹H NMR (400 Mhz, acetone-d₆): δ 8.89 (dd, 1H), 8.44 (dd, 1H), 8.09 (d, 1H), 8.02 (s, 1H), 7.91 (m, 3H), 7.82 (s, 1H), 7.71 (m, 2H), 7.56 (m, 2H), 7.44 (m, 4H), 7.19 (m, 2H), 6.94 (m, 1H), 5.20 (s, 2H), 3.08 (s, 3H), 1.87 (s, 6H).

EXAMPLE 44

N-(1-{3-[6-(1-Methanesulfonyl-1-methyl-ethyl)-quinolin-8-yl]-phenyl}-ethyl)-N-(4-methanesulfonyl-phenyl)-benzamide

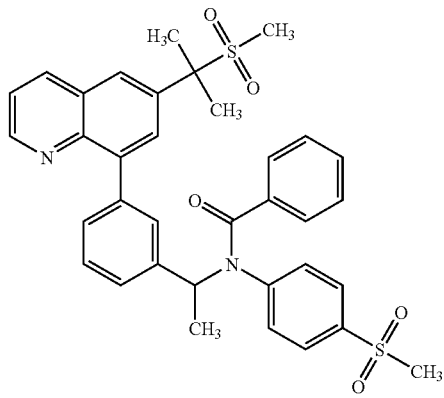

Step 1: (1-{3-[6-(1-Methanesulfonyl-t-methyl-ethyl)-quinolin-8-yl]-phenyl}-ethyl)-4-methylsulfanyl-phenyl)-amine To suspension of Quinoline 13 (1.0 eq) in EtOH (0.14M) was added 4-methylsulfanyl-phenylamine (1.1 eq). The resulting mixture was refluxed for 12 h, cooled to room temperature and concentrated to half of the initial volume. After addition of hexane (2× volume of EtOH), the resulting precipitate was filtered to afford the corresponding imine, which was used next as such. To solution of the imine in THF (0.14M) at −78° C. was added dropwise MeLi (1.26M;

3.0 eq). The resulting mixture was stirred at −78° C. for 2 h, quenched at −78° C. using saturated aqueous NH₄Cl and extracted with EtOAc. The combined organic extracts were washed with brine, dried over MgSO₄, filtered and concentrated. Flash chromatography (CH₂Cl₂:EtOAc; 9:1) afforded the desired compound as a foam.

Step 2: N-(1-f 3-[6-(1-Methanesulfonyl-1-methyl-ethyl)-quinolin-8-yl]-phenyl}-ethyl)-N-(4-methylsulfanyl-phenyl)-benzamide To solution of the N-benzylaniline from Step 1 (1.0 eq) in CH₂Cl₂ (0.2M) was added NEt₃ (10 eq), DMAP (0.05 eq) and benzoyl chloride (2.5 eq). The resulting mixture was stirred for 12 h, quenched with excess tetraethylenepentamine, poured in saturated aqueous NH₄Cl and extracted with EtOAc (2×). The combined organic extracts were washed with brine, dried over Na₂ $_{SO4}$, filtered and concentrated. Flash chromatography (CH₂Cl₂:EtOAc; 95:5) afforded the desired compound as a foam.

Step 3: Example 44

Prepared according to the procedure described in EXAMPLE 17, Step 5, but using the N-(1-{3-[6-(1-methanesulfonyl-1-methyl-ethyl)-quinolin-8-yl]-phenyl)-ethyl)-N-(4-methylsulfanyl-phenyl)-benzamide thioether from Step 2 as the starting material. Flash chromatography (CH₂Cl₂:EtOAc; 4:1) afforded the compound as a light yellow solid.

¹H NMR (400 MHz, acetone-d₆): δ 8.94 (dd, 1H), 8.46 (dd, 1H), 8.28 (d, 1H), 8.15 (d, 1H), 7.94 (s, 1H), 7.72 (dd, 2H), 7.63 (d, 1H), 7.60 (dd, 1H), 7.47 (t, 1H), 7.39–7.34 (m, 5H), 7.25–7.17 (m, 3H), 6.40 (q, 1H), 3.00 (s, 3H), 2.71 (s, 3H), 1.99 (s, 3H), 1.98 (s, 3H), 1.63 (d, 3H). LRMS (CI) 627 (M+H)⁺

EXAMPLE 45

Cyclopropanecarboxylic acid (1-{3-[6-(1-methanesulfonyl-1-methyl-ethyl)-quinolin-8-yl]-phenyl}-ethyl)-(4-methanesulfonyl-phenyl)-amide

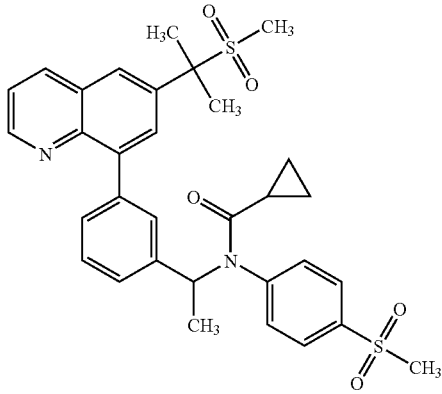

Prepared according to the procedure described in EXAMPLE 44 but using in the second step cyclopropanecarbonyl chloride as the starting material. Flash chromatography (CH₂Cl₂:EtOAc; 7:3) afforded the title compound as a foam.

¹H NMR (400 MHz, acetone-d₆): δ 8.84 (dd, 1H), 8.44 (dd, 1H), 8.27 (d, 1H), 8.12 (d, 1H), 7.93 (d, 2H), 7.74 (s, 1H), 7.55 (m, 4H), 7.39 (t, 1H), 7.27 (d, 1H), 6.35 (q, 1H), 3.10 (s, 3H), 2.72 (s, 3H), 1.98 (s, 6H), 1.52 (d, 3H), 1.17 (m, 1H), 0.84 (m, 2H), 0.57 (m, 2H).

EXAMPLE 46

2,2,2-Trifluoro-N-(1-{3-[6-(1-methanesulfonyl-1-methyl-ethyl)-quinolin-8-yl]-phenyl}-ethyl-N-(4-methanesulfonyl-phenyl)-aectamide

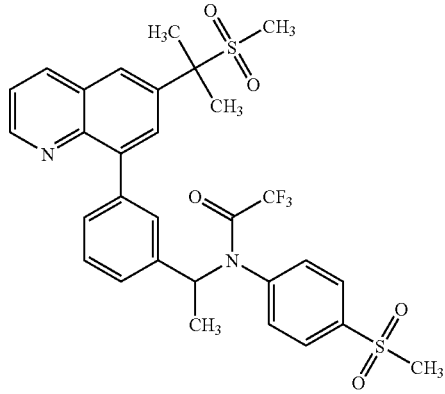

Prepared according to the procedure described in EXAMPLE 44 but using in the second step trifluoroacetyl chloride as the starting material. Flash chromatography (CH₂Cl₂:EtOAc; 7:3) afforded the title compound as a foam.

¹H NMR (400 MHz, acetone-d₆): δ 8.92 (dd, 1H), 8.46 (dd, 1H), 8.38 (d, 1H), 8.12 (s, 1H), 8.08 (m, 1H), 7.82 (m, 2H), 7.77 (s, 1H), 7.61 (d, 1H), 7.58 (dd, 1H), 7.42 (t, 1H), 7.40 (m, 1H), 7.23 (d, 1H), 6.22 (q, 1H), 3.11 (s, 3H), 2.72 (s, 3H), 1.98 (s, 6H), 1.61 (d, 3H).

EXAMPLE 47

5-Methyl-isoxazole-3-carboxylic acid (1-{3-[6-(1-methanesulfonyl-1-methyl-ethyl)-quinolin-8-yl]-phenyl}-ethyl)-(4-methanesulfonyl-phenyl)-amide

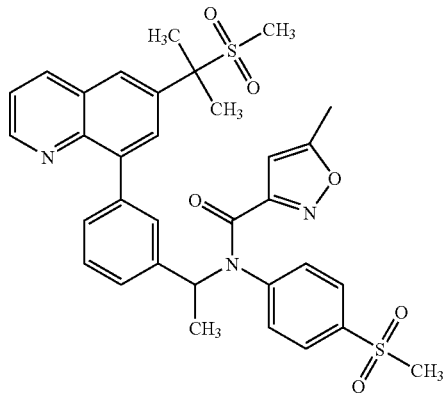

Prepared according to the procedure described in EXAMPLE 44 but using in the second step 5-methyl-isoxazole-3-carbonyl chloride as the starting material. Flash chromatography (CH₂Cl₂:EtOAc; 7:3) afforded the title compound as a foam.

¹H NMR (400 MHz, acetone-d₆): δ 8.91 (dd, 1H), 8.42 (dd, 1H), 8.28 (d, 1H), 8.11 (d, 1H), 7.82 (m, 3H), 7.64 (d, 1H), 7.56 (dd, 1H), 7.41 (m, 3H), 7.32 (d, 1H), 6.37 (br q, 1H), 6.20 (s, 1H), 3.03 (s, 3H), 2.70 (s, 3H), 2.30 (s, 3H), 1.97 (s, 6H), 1.62 (d, 3H).

EXAMPLE 48, 49, 50

4-Fluoro-N-(1-{3-[6-(1-methanesulfonyl-1-methyl-ethyl)-quinolin-8-yl]-phenyl}-ethyl)-N-(4-methane-sulfonyl-phenyl)-benzamide

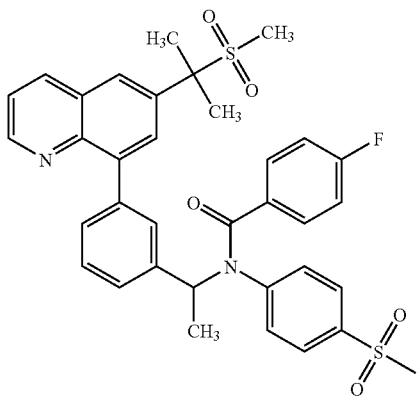

Prepared according to the procedure described in EXAMPLE 44 but using in the second step 4-fluorobenzoyl chloride as the starting material. Flash chromatography (CH$_2$Cl$_2$:EtOAc; 7:3) afforded the title compound (EXAMPLE 48) as a foam. Separation of the two enantiomer by HPLC on a Chiral-AD column (Hex/EtOH 3/2 to EtOH) afforded EXAMPLE 49 (less polar isomer; 9.5 min) and EXAMPLE 50 (more polar isomer; 12.9 min) as foams.

$^1$H NMR (400 MHz, acetone-d$_6$): δ 8.88 (dd, 1H), 8.42 (dd, 1H), 8.26 (d, 1H), 8.14 (d, 1H), 7.94 (s, 1H), 7.76 (d, 2H), 7.63 (d, 1H), 7.54 (dd, 1H), 7.40 (m, 6H), 6.97 (m, 2H), 6.38 (br q, 1H), 3.08 (s, 3H), 2.71 (s, 3H), 1.98 (s, 6H), 1.62 (d, 3H).

EXAMPLE 51

N-(1-{3-[6-(1-Methanesulfonyl-1-methyl-ethyl)-quinolin-8-yl]-phenyl}-ethyl)-N-(4-methanesulfonyl-phenyl)-acetamide

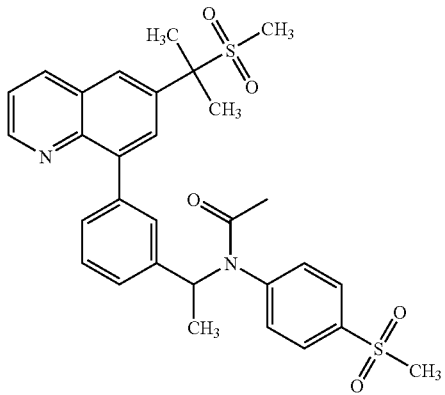

Prepared according to the procedure described in EXAMPLE 44 but using in the second step acetyl chloride as the starting material. Flash chromatography (CH$_2$Cl$_2$: EtOAc; 7:3) and recrystallization in EtOH/Hex afforded the title compound as a white solid.

$^1$H NMR (400 MHz, acetone-d$_6$): δ 8.92 (dd, 1H), 8.47 (dd, 1H), 8.27 (d, 1H), 8.11 (d, 1H), 7.93 (d, 2H), 7.72 (s, 1H), 7.60 (m, 2H), 7.48 (d, 2H), 7.40 (t, 1H), 7.28 (d, 1H), 6.30 (br q, 1H), 3.11 (s, 3H), 2.72 (s, 3H), 1.98 (s, 6H), 1.78 (s, 3H), 1.50 (d, 3H).

EXAMPLE 52

2,4-Difluoro-N-(1-{3-[6-(1-methanesulfonyl-1-methyl-ethyl)-quinolin-8-yl]-phenyl}-ethyl)-N-(4-methanesulfonyl-phenyl)-benzamide

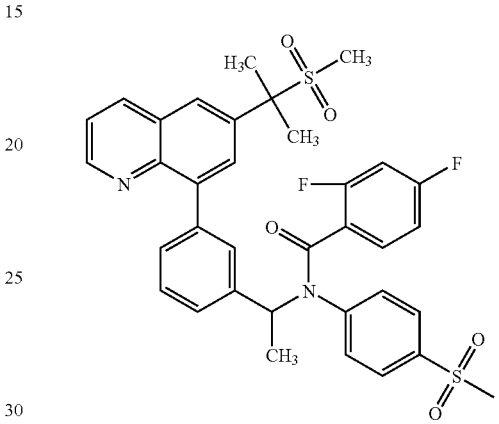

Prepared according to the procedure described in EXAMPLE 44 but using in the second step 2,4-difluorobenzoyl chloride as the starting material. Flash chromatography (CH$_2$Cl$_2$:EtOAc; 7:3) afforded the title compound as a foam.

$^1$H NMR (400 MHz, acetone-d$_6$): δ 8.95 (dd, 1H), 8.45 (dd, 1H), 8.27 (d, 1H), 8.13 (d, 1H), 7.86 (s, 1H), 7.77 (d, 2H), 7.60 (m, 2H), 7.41 (m, 5H), 6.87 (m, 2H), 6.37 (br q, 1H), 3.00 (s, 3H), 2.71 (s, 3H), 1.99 (s, 6H), 1.64 (d, 3H).

EXAMPLE 53

4-(1-Hydroxy-1-methyl-ethyl)-N-(1-{3-[6-(1-methanesulfonyl-1-methyl-ethyl)-quinolin-8-yl]-phenyl}-ethyl)-N-(4-methanesulfonyl-phenyl)-benzamide

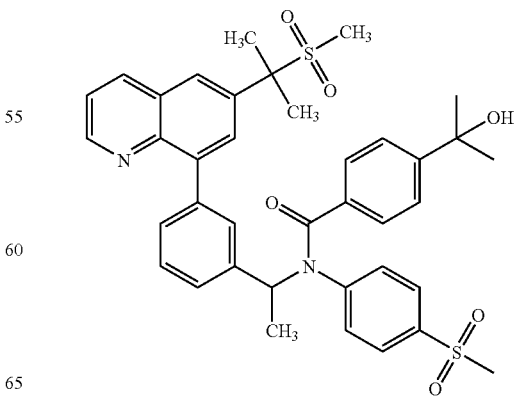

Step 1: N-(1-f 3-[6-(1-Methanesulfonyl-1-methyl-ethyl)-quinolin-8-yl]-phenyl}-ethyl)-N-(4-methylsulfanyl-phenyl)-terephthalamic acid methyl ester Prepared according to the procedure described in EXAMPLE 44 (Steps 1 and 2), but using in the second step 4-chlorocarbonyl-benzoic acid methyl ester as the starting material. Flash chromatography (CH$_2$Cl$_2$:EtOAc; 8:2) afforded the desired compound as a foam.

Step 2: 4-(1-Hydroxy-1-methyl-ethyl)-N-(1-f 3-[6-(1-methanesulfonyl-1-methyl-ethyl)-quinolin-8-yl]-phenyl}-ethyl)-N-(4-methylsulfanyl-phenyl)-benzamide Prepared according to the procedure described in EXAMPLE 11 but using the N-(1-{3-[6-(1-methanesulfonyl-1-methyl-ethyl)quinolin-8-yl]-phenyl}-ethyl)-N-(4-methylsulfanyl-phenyl)-terephthalamic acid methyl ester from Step 1 as the starting material. Flash chromatography (CH$_2$Cl$_2$:EtOAc; 3:2) afforded the desired compound as a foam.

Step 3: Example 53

Prepared according to the procedure described in EXAMPLE 17, Step 5 but using the 4-(1-hydroxy-1-methylethyl)-N-(1-{3-[6-(1-methanesulfonyl-1-methyl-ethyl)-quinolin-8-yl]-phenyl}-ethyl)-N-(4-methylsulfanyl-phenyl)-benzamide from present Step 2 as the starting material. Flash chromatography (CH$_2$Cl$_2$:EtOAc; 2:3) afforded the title compound as a foam.

$^1$H NMR (400 MHz, acetone-d$_6$): δ 8.92 (dd, 1H), 8.43 (dd, 1H), 8.27 (d, 1H), 8.12 (d, 1H), 7.92 (s, 1H), 7.72 (d, 2H), 7.62 (d, 1H), 7.60 (dd, 1H), 7.46 (t, 1H), 7.35 (m, 7H), 6.40 (q, 1H), 4.03 (s, 1H), 3.00 (s, 3H), 2.71 (s, 3H), 1.98 (s, 6H), 1.62 (d, 3H), 1.40 (s, 6H).

EXAMPLE 54

N-(1-{3-[6-(1-Methanesulfonyl-1-methylethyl)-quinolin-8-yl]-phenyl}-ethyl)-N-(4-methanesulfonyl-phenyl)-nicotinamide

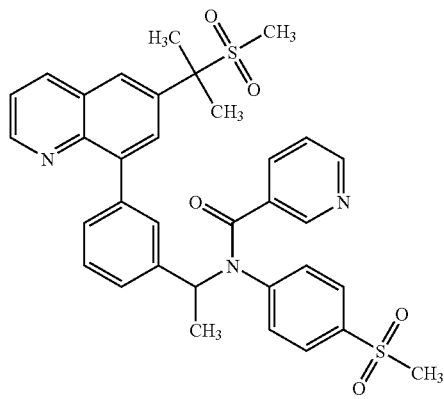

Prepared according to the procedure described in EXAMPLE 44 but using in the second step nicotinoyl chloride (HCl salt) as the starting material. Flash chromatography (EtOAc:Ace; 9:1) afforded the title compound as a light yellow solid.

$^1$H NMR (400 MHz, acetone-d$_6$): δ 8.93 (dd, 1H), 8.53 (d, 1H), 8.45 (dd, 1H), 8.40 (dd, 1H), 8.27 (d, 1H), 8.15 (d, 1H), 7.94 (s, 1H), 7.76 (d, 2H), 7.69 (dt, 1H), 7.64 (d, 1H), 7.57 (dd, 1H), 7.46 (t, 1H), 7.43 (d, 2H), 7.38 (d, 1H), 7.19 (dd, 1H), 6.40 (q, 1H), 3.01 (s, 3H), 2.72 (s, 3H), 1.99 (s, 3H), 1.98 (s, 3H), 1.65 (d, 3H).

LRMS (CI) 628 (M+H)$^+$

EXAMPLE 55

4-Fluoro-N-(1-{3-[6-(1 methanesulfonyl-1-methyl-ethyl)-quinolin-8-yl]-phenyl}-ethyl)-N-(4-methane-sulfonyl-phenyl)-3-trifluoromethyl-benzamide

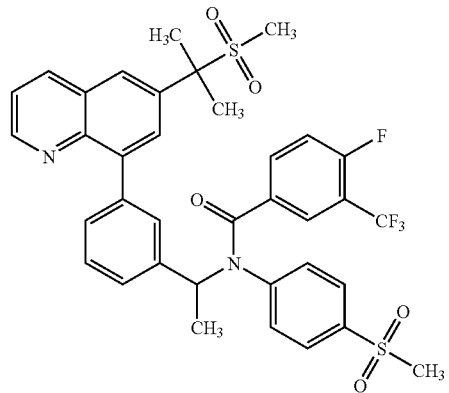

Prepared according to the procedure described in EXAMPLE 44 but using in the second step 4-fluoro-3-trifluoromethyl-benzoyl chloride as the starting material. Flash chromatography (Hex:EtOAc; 7:3) afforded the title compound as a foam.

$^1$H NMR (400 MHz, acetone-d$_6$): δ 8.90 (dd, 1H), 8.46 (dd, 1H), 8.27 (d, 1H), 8.14 (d, 1H), 7.91 (s, 1H), 7.78 (d, 2H), 7.67 (d, 2H), 7.63 (d, 1H), 7.57 (dd, 1H), 7.46 (m, 3H), 7.38 (d, 1H), 7.25 (t, 1H), 6.40 (q, 1H), 3.00 (s, 3H), 2.71 (s, 3H), 1.99 (s, 3H), 1.98 (s, 3H), 1.67 (d, 3H).

EXAMPLE 56

2,4,6-Trifluoro-N-(1-{3-[6-(1-methanesulfonyl-1-methyl-ethyl)-quinolin-8-yl]-phenyl}-ethyl)-N-(4-methanesulfonyl-phenyl)-benzamide

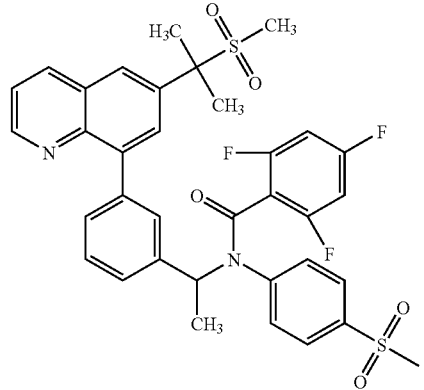

Prepared according to the procedure described in EXAMPLE 44 but using in the second step 2,4,6-trifluorobenzoyl chloride as the starting material. Flash chromatography (Hex:EtOAc; 7:3) afforded the title compound as a foam.

¹H NMR (400 MHz, acetone-d₆): δ 8.95 (dd, 1H), 8.47 (dd, 1H), 8.29 (d, 1H), 8.11 (d, 1H), 7.79 (m, 3H), 7.60 (m, 2H), 7.40 (m, 4H), 6.84 (t, 1H), 6.77 (t, 1H), 6.40 (q, 1H), 2.99 (s, 3H), 2.71 (s, 3H), 1.99 (s, 3H), 1.98 (s, 3H), 1.68 (d, 3H).

EXAMPLE 57

2-Chloro-N-(1-(3-[6-(1-methanesulfonyl-1-methyl-ethyl)-quinolin-8-yl]-phenyl}-ethyl)-N-(4-methane-sulfonyl-phenyl)-4-nitro-benzamide

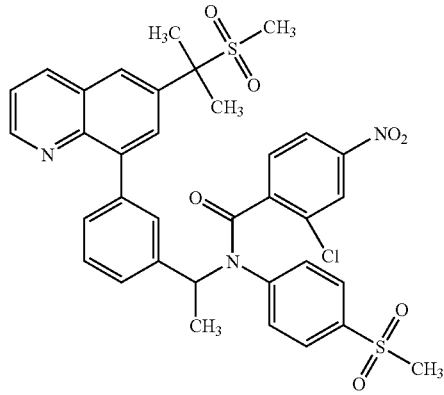

Prepared according to the procedure described in EXAMPLE 44 but using in the second step 2-chloro-4-nitrobenzoyl chloride as the starting material. Flash chromatography (Hex:EtOAc; 7:3) afforded the title compound as a foam.

¹H NMR (400 MHz, acetone-d₆): δ 8.98 (dd, 1H), 8.46 (dd, 1H), 8.28 (d, 1H), 8.12 (d, 1H), 8.07–8.01 (m, 2H), 7.86 (s, 1H), 7.73 (d, 2H), 7.63–7.58 (m, 3H), 7.50 (d, 2H), 7.49–7.41 (s, 2H), 6.46 (q, 1H), 2.94 (s, 3H), 2.72 (s, 3H), 1.99 (s, 3H), 1.98 (s, 3H), 1.69 (d, 3H).

EXAMPLE 58

3-Isopropyl-1-(1-{3-[6-(1-methanesulfonyl-1-methyl-ethyl)-quinolin-8-yl]-phenyl}-ethyl)-1-(4-methanesulfonyl-phenyl)-urea

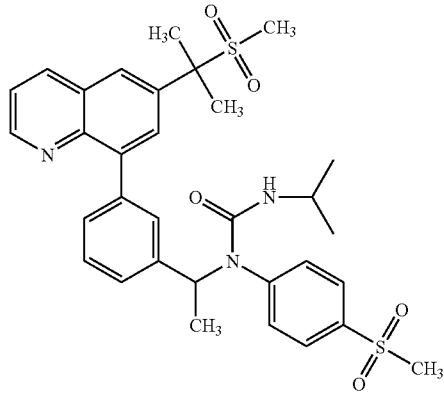

Prepared according to the procedure described in EXAMPLE 41 but using (1-{3-[6-(1-Methanesulfonyl-1-methyl-ethyl)-quinolin-8-yl]-phenyl}-ethyl)-(4-methylsulfanyl-phenyl)-amine (EXAMPLE 44, step 1) and iso-propyl isocyanate as the starting materials. Flash chromatography (CH₂Cl₂:EtOAc; 4:1) afforded the title compound as a foam.

¹H NMR (400 MHz, acetone-d₆): δ 8.95 (dd, 1H), 8.44 (dd, 1H), 8.26 (d, 1H), 8.10 (d, 1H), 7.86 (dd, 2H), 7.75 (s, 1H), 7.58–7.55 (m, 2H), 7.42–7.38 (m, 3H), 7.31 (d, 1H), 6.17 (q, 1H), 4.91 (d, NH), 3.95–3.89 (m, 1H), 3.06 (s, 3H), 2.71 (s, 3H), 1.99 (s, 3H), 1.98 (s, 3H), 1.49 (d, 3H), 1.00 (d, 3H), 0.94 (d, 3H).

LRMS (CI) 608 (M+H)⁺

EXAMPLE 59

3-(2-Chloro-phenyl)-1-(1-{3-[6-(1-methanesulfonyl-1-methyl-ethyl)-quinolin-8-yl]-phenyl}-ethyl)-[(4-methanesulfonyl-phenyl)-urea

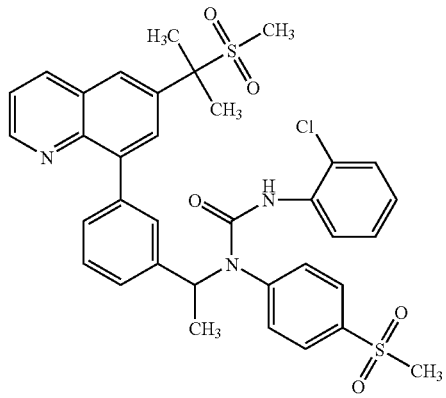

Prepared according to the procedure described in EXAMPLE 58 but using 1-chloro-2-isocyanato-benzene as the starting materials. Flash chromatography (CH₂Cl₂:EtOAc; 7:3) afforded the title compound as a foam.

¹H NMR (400 MHz, acetone-d₆): δ 8.88 (dd, 1H), 8.42 (dd, 1H), 8.26 (d, 1H), 8.20 (dd, 1H), 8.11 (d, 1H), 8.06 (d, 2H), 7.84 (s, 1H), 7.68 (d, 2H), 7.61 (d, 1H), 7.51 (dd, 1H), 7.43 (t, 1H), 7.38 (d, 1H), 7.25 (m, 1H), 6.98 (dt, 1H), 6.72 (br s, 1H), 6.22 (q, 1H), 3.12 (s, 3H), 2.70 (s, 3H), 1.98 (s, 6H), 1.62 (d, 3H).

EXAMPLE 60

3,4-Dichloro-N-(1-{3-[6-(1-methanesulfonyl-1-methyl-ethyl)-quinolin-8-yl]-phenyl}-ethyl)-N-(4-methanesulfonyl-phenyl)-benzenesulfonamide

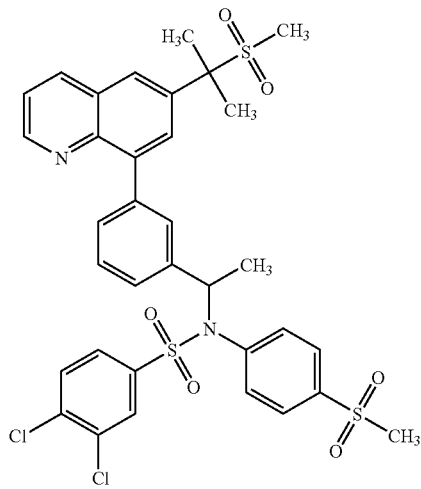

Step 1: 3,4-Dichloro-N-(1-{3-[6-(1-methanesulfonyl-1-methyl-ethyl)-quinolin-8-yl]-phenyl}-ethyl)-N-(4-methylsulfanyl-phenyl)-benzenesulfonamide To solution of (1-{3-[6-(1-Methanesulfonyl-1-methyl-ethyl)-quinolin-8-yl]-phenyl}-ethyl)-(4-methylsulfanyl-phenyl)-amine from EXAMPLE 44 (Step 1) (1.0 eq) in pyridine (0.38M) was added 3,4-dichloro-benzenesulfonyl chloride (3.2 eq). The resulting mixture was stirred at 80° C. for 12 h, cooled to room temperature, poured in saturated aqueous NaHCO$_3$ and extracted with EtOAc (2×). The combined organic extracts were washed with brine, dried over MgSO$_4$, filtered and concentrated. Flash chromatography (CH$_2$Cl$_2$:EtOAc; 9:1) afforded the desired compound as a foam.

Step 2: Example 60

Prepared according to the procedure described in EXAMPLE 13 but using the 3,4-dichloro-N-(1-{3-[6-(1-methanesulfonyl-1-methyl-ethyl)-quinolin-8-yl]-phenyl}-ethyl)-N-(4-methylsulfanyl-phenyl)-benzenesulfonamide from present Step 1 as the starting material. Flash chromatography (CH$_2$Cl$_2$:EtOAc; 9:1) afforded the title compound as a white solid.

$^1$H NMR (400 MHz, acetone-d$_6$): δ 8.87 (dd, 1H), 8.46 (dd, 1H), 8.28 (d, 1H), 8.07 (d, 1H), 7.89 (d, 2H), 7.84 (s, 1H), 7.68–7.55 (m, 5H), 7.44 (d, 2H), 7.37 (t, 1H), 7.20 (d, 1H), 5.81 (q, 1H), 3.10 (s, 3H), 2.71 (s, 3H), 1.98 (s, 6H), 1.59 (d, 3H).

LRMS (CI) 731 (M+H)$^+$

EXAMPLE 61

1-{2-Fluoro-5-[6-(1-methanesulfonyl-1-methyl-ethyl)-quinolin-8-yl]-benzyl}-3-isopropyl-1-(4-methanesulfonyl-phenyl)-urea

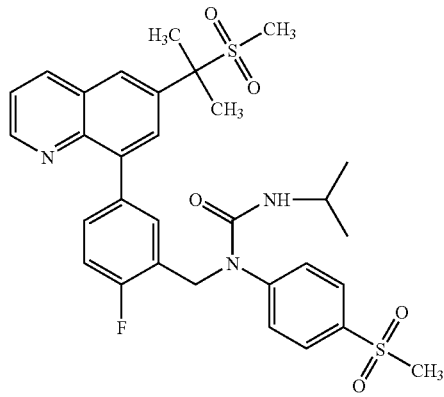

Step 1: 4-Fluoro-3-hydroxymethyl benzene boronic acid

To solution of (5-bromo-2-fluoro-phenyl)-methanol (1.0 eq) in THF (0.1M) at −78° C. was added dropwise n-BuLi (2.5M in Hex; 2.2 eq). The resulting mixture was stirred at −78° C. for 30 min then tri-isopropoxy borane (2.2 eq) was added. The final mixture was stirred 15 min at −78° C. then allowed to warm slowly to room temperature and stirred an extra hour. The reaction was quenched with HCl (10%) and extracted with EtOAc (2×). The combined organic extracts were washed with brine, dried over MgSO$_4$, filtered and concentrated. The residue was dissolved in EtOAc, water (few drops) was added then hexane until a precipitate formed. After 12 h of stirring, the desired compound was isolated by filtration as a white solid.

Step 2: {2-Fluoro-5-[6-(1-methanesulfonyl-1-methyl-ethyl)-quinolin-8-yl]-phenyl}-methanol Prepared according to the procedure described in Quinoline 4 but using the previous 4-Fluoro-3-hydroxymethyl benzene boronic acid from Step 1 and Quinoline 10 as the starting materials. Flash chromatography (CH$_2$Cl$_2$:EtOAc; 1:1) afforded the desired compound as a white solid.

Step 3: 2-Fluoro-5-[6-(1-methanesulfonyl-1-methyl-ethyl)-quinolin-8-yl]-benzaldehyde Prepared according to the oxidation procedure described in Quinoline 14 (Step 1) but using the {2-fluoro-5-[6-(1-methanesulfonyl-1-methyl-ethyl)-quinolin-8-yl]-phenyl)}-methanol from Step 2 as the starting material.

Step 4: {2-Fluoro-5-[6-(1-methanesulfonyl-1-methyl-ethyl)-quinolin-8-yl]-benzyl}-(4-methanesulfonyl-phenyl)-amine Prepared according to the procedure described in EXAMPLE 36 (Step 1) but using the 2-fluoro-5-[6-(1-methanesulfonyl-1-methyl-ethyl)-quinolin-8-yl]-benzaldehyde from present Step 3 as the starting material.

Step 5: Example 61

Prepared in two steps according to the procedures described in EXAMPLE 41 but using the {2-fluoro-5-[6-(1-methanesulfonyl-1-methyl-ethyl)-quinolin-8-yl]-benzyl}-(4-methanesulfonyl-phenyl)-amine from present Step 4 as the starting material. Flash chromatography (CH$_2$Cl$_2$:MeOH; 96:4) afforded the compound as a foam.

$^1$H NMR (400 MHz, acetone-d$_6$): δ 8.92 (dd, 1H), 8.42 (dd, 1H), 8.37 (d, 1H), 8.10 (d, 1H), 7.90 (m, 3H), 7.72 (d, 2H), 7.65 (m, 1H), 7.57 (dd, 1H), 7.17 (m, 1H), 5.70 (br d, 1H), 5.65 (s, 2H), 3.91 (m, 1H), 3.07 (s, 3H), 2.70 (s, 3H), 1.95 (s, 6H), 1.03 (d, 6H).

EXAMPLE 62

N-{2-Fluoro-5-[6-(1-methanesulfonyl-1-methyl-ethyl)-quinolin-8-yl]-benzyl}-N-(4-methanesulfonyl-phenyl)-benzamide

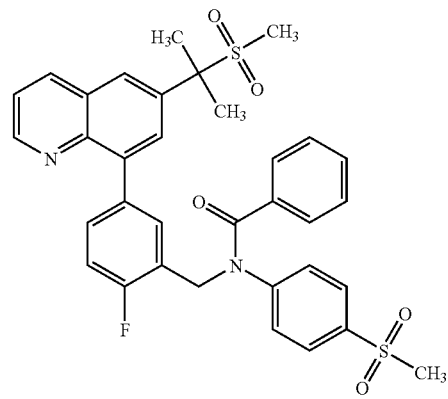

Prepared in two steps according to the procedures described in EXAMPLE 44 (Steps 2 and 3) but using {2-fluoro-5-[6-(1-methanesulfonyl-1-methyl-ethyl)-quinolin-8-yl]-benzyl}-(4-methanesulfonyl-phenyl)-amine from EXAMPLE 61 (Step 4) as the starting material. Flash chromatography (CH$_2$Cl$_2$:EtOAc; 3:7) afforded the title compound as a foam.

$^1$H NMR (400 MHz, acetone-d$_6$): δ 8.90 (dd, 1H), 8.42 (dd, 1H), 8.25 (d, 1H), 8.12 (d, 1H), 8.05 (dd, 1H), 7.82 (d, 2H), 7.68 (m, 1H), 7.57 (m, 3H), 7.38 (d, 2H), 7.30 (m, 1H), 7.20 (m, 3H), 5.39 (s, 2H), 3.03 (s, 3H), 2.71 (s, 3H), 1.97 (s, 6H).

EXAMPLE 63

N-(1-{2-Chloro-5-[6-(1-methanesulfonyl-1-methyl-ethyl)-quinolin-8-yl]-phenyl}-ethyl)-N-(4-methane-sulfonyl-phenyl)-benzamide

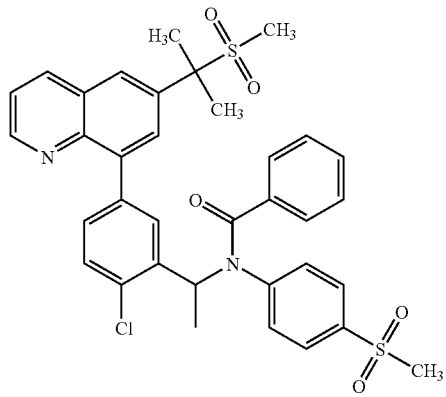

Step 1: (1-{2-Chloro-5-[6-(1-methanesulfonyl-1-methyl-ethyl)-quinolin-8-yl]-phenyl}-ethyl)-(4-methylsulfanyl-phenyl)-amine Prepared in four steps according to the procedure described in EXAMPLE 61 (Steps 1–3) and EXAMPLE 44 (Step 1), but using (5-bromo-2-chloro-phenyl)-methanol as the starting material. Flash chromatography (CH$_2$Cl$_2$:EtOAc; 9:1) afforded the desired compound as a foam.

Step 2: Example 63

Prepared in two steps according to the procedures described in EXAMPLE 44 (Steps 2 and 3) but using the (1-{2-chloro-5-[6-(1-methanesulfonyl-1-methyl-ethyl)-quinolin-8-yl]-phenyl}-ethyl)-(4-methylsulfanyl-phenyl)-amine from present Step 1 as the starting material. Flash chromatography (CH$_2$Cl$_2$:EtOAc; 2:3) afforded the title compound as a foam.

$^1$H NMR (400 MHz, acetone-d$_6$): δ 8.82 (dd, 1H), 8.32 (dd, 1H), 8.05 (d, 1H), 7.88 (d, 1H), 7.70–7.55 (m, 5H), 7.48 (dd, 1H), 7.35 (d, 2H), 7.25–7.11 (m, 5H), 6.50 (q, 1H), 2.93 (s, 3H), 2.87 (s, 3H), 1.69 (d, 3H), 1.64 (s, 6H).

EXAMPLE 64

1-{2-Chloro-5-[6-(1-methanesulfonyl-1-methyl-ethyl)-quinolin-8-yl]-benzyl}-3-isopropyl-1-(4-methanesulfonyl-phenyl)-urea

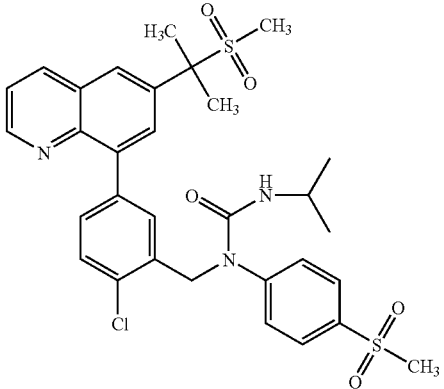

Prepared according to the procedures described in EXAMPLE 61 but using (5-bromo-2-fluoro-phenyl)-methanol as the starting material in the first step. Flash chromatography (CH$_2$Cl$_2$:EtOAc; 2:3) afforded the title compound as a foam.

$^1$H NMR (400 MHz, acetone-d$_6$): δ 8.92 (dd, 1H), 8.45 (dd, 1H), 8.38 (d, 1H), 8.10 (d, 1H), 7.92 (m, 3H), 7.72 (d, 2H), 7.64 (dd, 1H), 7.60 (d, 1H), 7.48 (d, 1H), 5.79 (br d, 1H), 5.19 (s, 2H), 3.92 (m, 1H), 3.10 (s, 3H), 2.71 (s, 3H), 1.99 (s, 6H), 1.02 (d, 6H).

EXAMPLE 65

4-Fluoro-3-(6-isopropyl-quinolin-8-yl)-N-(1-methyl-4-oxo-4,5-dihydro-1H imidazol-2-yl)-benzamide

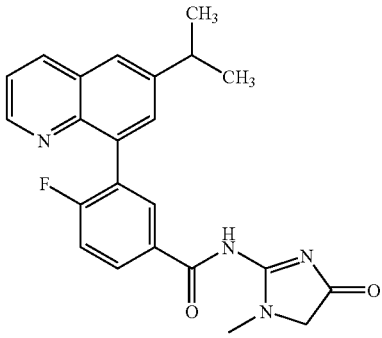

Step 1: 3-Dihydroxylboranyl-4-fluoro-benzoic acid

To solution of 3-Bromo-4-fluoro-benzoic acid (1.0 eq) in THF (0.2M) at −78° C. was added n-BuLi (2.5M in Hex; 2.2 eq). The resulting mixture was stirred at −78° C. for 15 min then tri-isopropoxy borane (2.2 eq). The final mixture was stirred 1 h at −78° C. then 4 h at room temperature and finally poured in HCl (10%). After stirring for 12 h, THP was evaporated and the residual mixture was diluted with EtOAc. The organic extract was washed with HCl (10%), brine, dried over MgSO$_4$, filtered and concentrated. The residue was suspended in EtOAc, stirred for 4 h and the desired compound was isolated by filtration.

Step 2:
4-Fluoro-3-(6-isopropyl-quinolin-8-yl)-benzoic acid

A mixture of Quinoline 1 (1.0 eq), the 3-dihydroxylboranyl-4-fluoro-benzoic acid from Step 1 (1.2 eq), Pd(PPh$_3$)$_4$ (0.05 eq) and aqueous Na$_2$CO$_3$ (2.0M; 4.0 eq) in propanol (0.1M) was stirred at 90° C. for 12 h. The resulting mixture was cooled to room temperature, poured in saturated aqueous NH$_4$Cl, the pH was adjusted to 5 with HCl (10%) and extracted with EtOAc (2×). The combined organic extracts were washed with brine, dried over MgSO$_4$, filtered. Upon concentration the desired compound crystallized and was isolated by filtration.

Step 3: Example 65

To solution of the 4-fluoro-3-(6-isopropyl-quinolin-8-yl)-benzoic acid from Step 2 (1.0 eq), EDCI (1.1 eq) and DMAP (1.1 eq) in CH$_2$Cl$_2$ (0.07M) was added 2-amino-1-methyl-1,5-dihydro-imidazol-4-one (1.1 eq). The resulting mixture was stirred for 12 h, poured in saturated aqueous NaHCO$_3$ and extracted with EtOAc (2×). The combined organic extracts were washed with brine, dried over MgSO$_4$, filtered and concentrated. Flash chromatography (EtOAc) afforded the compound as a white solid.

$^1$H NMR (300 MHz, acetone-d$_6$): δ 8.76 (dd, 1H), 8.39–8.31 (m, 3H), 7.86 (d, 1H), 7.73 (d, 1H), 7.48 (dd, 1H), 7.27 (t, 1H), 4.10 (s, 2H), 3.19 (s, 3H), 3.18 (m, 1H), 1.39 (d, 6H).

EXAMPLE 66

4-[3-(6-Isopropyl-quinolin-8-yl)-benzyloxy]-benzonitrile

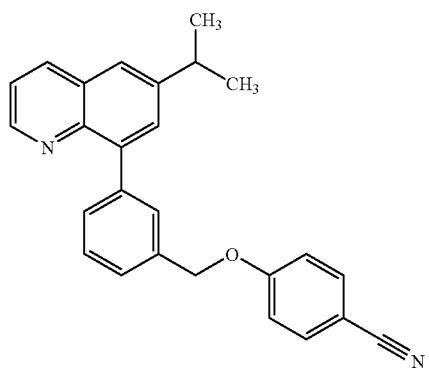

To solution of 4-hydroxy-benzonitrile (1.0 eq) in DMF (0.45M) was added NaH (60% dispersion in oil; 1.3 eq). The resulting mixture was stirred for 15 min then Quinoline 20 (0.93 eq) was added. The final mixture was stirred for 12 h, poured in water and extracted with Et$_2$O. The organic extract was washed with water (2×), brine, dried over MgSO$_4$, filtered and concentrated. Flash chromatography (Hex: EtOAc 0 to 50% gradiant) afforded the title compound as a foam.

$^1$H NMR (400 MHz, acetone-d$_6$): δ 8.80 (dd, 1H), 8.29 (dd, 1H), 7.84 (d, 1H), 7.78 (d, 1H), 7.72–7.67 (m, 4H), 7.51–7.45 (m, 3H), 7.20 (dd, 2H), 5.30 (s, 2H), 3.16 (sept, 1H), 1.36 (d, 6H).

LRMS (CI) 379 (M+H)$^+$

EXAMPLE 67

6-Isopropyl-8-[3-(4-methanesulfonyl-phenoxymethyl)-phenyl]-quinoline

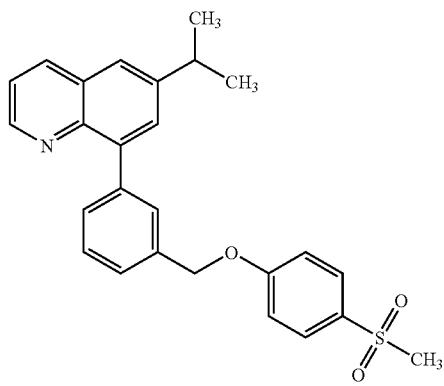

Step 1: 6-Isopropyl-8-[3-(4-methylsulfanyl-phenoxymethyl)-phenyl]-quinoline

Prepared according to the procedure described in EXAMPLE 66 but using 4-methylsulfanyl-phenol as the starting material.

Step 2: Example 67

Prepared according to the procedure described in EXAMPLE 13 but using the 6-Isopropyl-8-[3-(4-methylsulfanyl-phenoxymethyl)-phenyl]-quinoline from present Step 1 as the starting material. Flash chromatography (Hex: EtOAc 0 to 70% gradient) afforded the title compound as a foam.

$^1$H NMR (400 MHz, acetone-d$_6$): δ 8.80 (dd, 1H), 8.30 (dd, 1H), 7.88–7.85 (m, 3H), 7.77 (d, 1H), 7.72–7.70 (m, 2H), 7.51–7.49 (m, 2H), 7.46 (dd, 1H), 7.25 (dd, 1H), 5.32 (s, 2H), 3.15 (sept, 1H), 3.04 (s, 3H), 1.36 (d, 6H).
LRMS (CI) 432 (M+H)$^+$

EXAMPLE 68

2-{4-[3-(6-Isopropyl-quinolin-8-yl)-benzyloxy]-phenyl}-propan-2-ol

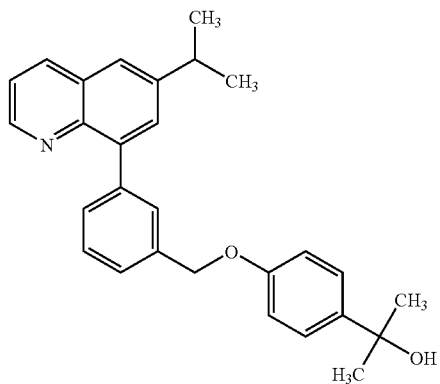

Step 1: 4-[3-(6-Isopropyl-quinolin-8-yl)-benzyloxy]-benzoic acid isopropyl ester Prepared according to the procedure described in EXAMPLE 66 but using 4-hydroxy-benzoic acid isopropyl ester as the starting material.

Step 2: Example 67

Prepared according to the procedure described in EXAMPLE 11 but using the previous ester from step 1 as the starting material. Flash chromatography (Hex:EtOAc 0 to 70% gradient) afforded the compound as a foam.

$^1$H NMR (400 MHz, acetone-$d_6$): δ 8.81 (dd, 1H), 8.29 (dd, 1H), 7.82 (s, 1H), 7.77 (d, 1H), 7.72 (d, 1H), 7.68 (dt, 1H), 7.49–7.41 (m, 5H), 6.97 (dd, 2H), 5.19 (s, 2H), 3.92 (s, OH), 3.16 (sept, 1H), 1.47 (s, 6H), 1.37 (d, 6H).

LRMS (CI) 412 (M+H)$^+$

EXAMPLE 69

1-(5-Methanesulfonyl-2-{3-[6-(1-methanesulfonyl-1-methylethyl)-quinolin-8-yl]-benzyloxy}-phenyl)-ethanone

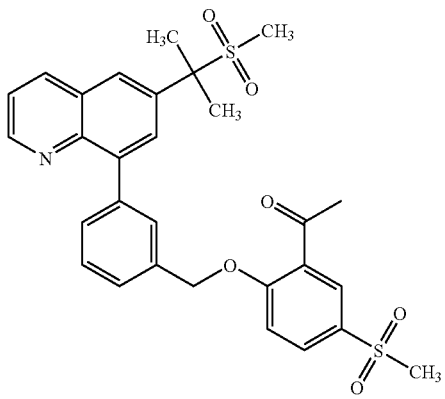

To solution of Quinoline 12 (1.0 eq) and 1-(2-hydroxy-5-methanesulfonyl-phenyl)-ethanone (1.08 eq) (from the procedure described in *Synthesis*, 1982, 11, 940) in DMF (0.05M) was added Cs$_2$CO$_3$ (1.08 eq). The mixture was stirred for 12 h then poured in saturated aqueous NH$_4$Cl and extracted with EtOAc (2×). The combined organic extracts were washed with brine, dried over MgSO$_4$, filtered and concentrated. Flash chromatography (CH$_2$Cl$_2$:EtOAc; 50 to 100%) afforded the title compound as a white solid.

$^1$H NMR (300 MHz, acetone-$d_6$): δ 8.90 (dd, 1H), 8.43 (dd, 1H), 8.27 (d, 1H), 8.17 (d, 1H), 8.14 (d, 1H), 8.05 (dd, 1H), 7.97 (s, 1H), 7.75 (d, 1H), 7.67–7.52 (m, 4H), 5.50 (s, 2H), 3.10 (s, 3H), 2.70 (s, 3H), 2.65 (s, 3H), 1.97 (s, 6H).

EXAMPLE 70

1-(5-Methanesulfonyl-2-{3-[C-(1-methanesulfonyl-1-methyl-ethyl)-quinolin-8-yl]-benzyloxy}-phenyl)-ethanol

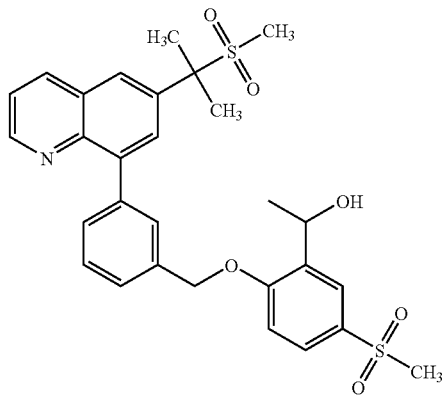

To solution of 1-(5-Methanesulfonyl-2-{3-[6-(1-methanesulfonyl-1-methyl-ethyl)-quinolin-8-yl]-benzyloxy}-phenyl)-ethanone from EXAMPLE 69 (1.0 eq) in ethanol (0.01M) was added NaBH$_4$ (200 eq). The mixture was stirred for 12 h then poured in aqueous HCl (10%) and extracted with EtOAc (2×). The combined organic extracts were washed with saturated aqueous NaHCO$_3$, brine, dried over MgSO$_4$, filtered and concentrated. Flash chromatography (CH$_2$Cl$_2$:EtOAc; 50 to 100%) afforded the title compound as a white solid.

$^1$H NMR (300 MHz, acetone-$d_6$): δ 8.92 (dd, 1H), 8.45 (dd, 1H), 8.27 (d, 1H), 8.13 (dd, 2H), 7.92 (s, 1H), 7.82–7.72 (m, 2H), 7.61–7.52 (m, 3H), 7.34 (d, 1H), 5.40 (d, 2H), 5.36–5.28 (m, 1H), 4.32 (d, 1H), 3.04 (s, 3H), 2.71 (s, 3H), 1.98 (s, 6H), 1.42 (d, 3H).

EXAMPLE 71

1-(2-Hydroxy-4-{3-[6-(1-methanesulfonyl-1-methyl-ethyl)-quinolin-8-yl]-benzyloxy}-phenyl)-ethanone

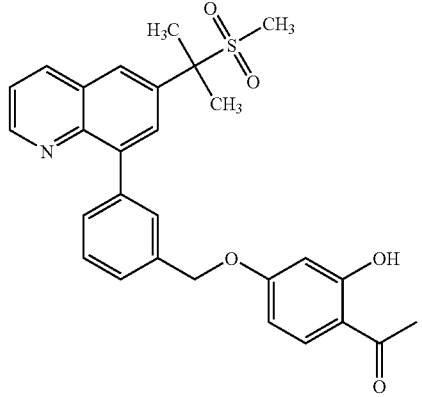

To solution of Quinoline 12 (1.0 eq) and 1-(2,4-dihydroxy-phenyl)-ethanone (1.9 eq) in acetone (0.36M) was added K$_2$CO$_3$ (1.27 eq). The resulting mixture was refluxed for 2 h, cooled to room temperature then poured in water and extracted with EtOAc (2×). The combined organic extracts were washed with brine, dried over MgSO$_4$, filtered and concentrated. Flash chromatography (Hex:EtOAc; 1:1) afforded the title compound as a white solid.

¹H NMR (500 MHz, acetone-d₆): δ 12.7 (s, 1H), 8.92 (d, 1H), 8.43 (d, 1H), 8.27 (s, 1H), 8.11 (s, 1H), 7.98 (dd, 2H), 7.71 (d, 1H), 7.55 (m, 3H), 6.68 (d, 1H), 6.55 (s, 1H), 5.32 (s, 2H), 2.72 (s, 3H), 2.62 (s, 3H), 2.12 (s, 6H).
LRMS (CI) 490 (M+H)⁺

EXAMPLE 72

1-(2-Hydroxy-4-{3-[6-(1-methanesulfonyl-methyl-ethyl)-quinolin-8-yl]-benzyloxy}-3-propyl-phenyl)-ethanone

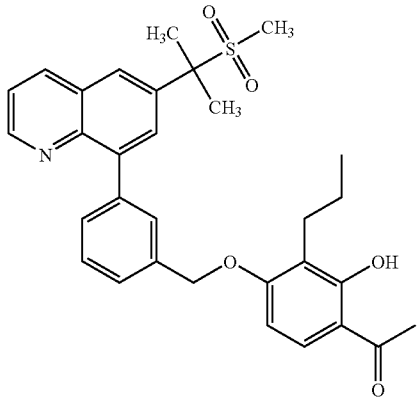

Prepared according to the procedure described in EXAMPLE 71 but using 1-(2,4-dihydroxy-3-propyl-phenyl)-ethanone as the starting material. Flash chromatography (Hex:EtOAc; 1:1) afforded the title compound as a white solid.

¹H NMR (500 MHz, acetone-d₆): δ 12.9 (s, 1H), 8.91 (dd, 1H), 8.44 (dd, 1H), 8.2 (s, 1H), 8.14 (s, 1H), 7.88 (s, 1H), 7.78 (d, 1H), 7.71 (s, 1H), 7.56 (d, 1H), 7.53 (s, 2H), 6.76 (d, 1H), 5.3 (s, 2H), 2.71 (s, 5H), 2.56 (s, 3H), 1.95 (s, 6H), 1.54 (t, 2H), 0.82 (dd, 3H).
LRMS (CI) 532 (M+H)⁺

EXAMPLE 73

6-(1-Methanesulfonyl-1-methyl-ethyl)-8-[3-(2-methylsulfanyl-phenoxymethyl)-phenyl]-quinoline

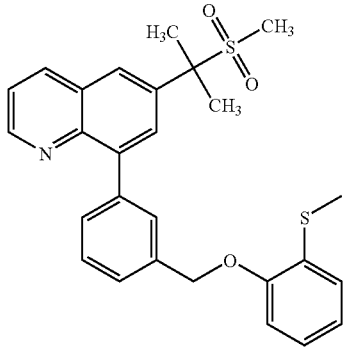

To solution of Quinoline 12 (1.0 eq) and 2-methylsulfanyl-phenol (1.2 eq) in THF (0.04M) was added Cs₂CO₃ (1.6 eq). The resulting mixture was stirred for 12 h then poured in saturated aqueous NH₄Cl and extracted with EtOAc. The organic extract was washed with water, brine and concentrated. Flash chromatography (Hex:EtOAc; 40 to 100% in 15 min) afforded the title compound as a foam.

¹H NMR (400 MHz, acetone-d₆): δ 8.92 (dd, 1H), 8.45 (dd, 1H), 8.28 (d, 1H), 8.15 (d, 1H), 7.92 (s, 1H), 7.72 (d, 1H), 7.56 (m, 2H), 7.51 (t, 1H), 7.19 (d, 1H), 7.11 (m, 2H), 6.97 (dt, 1H), 5.29 (s, 2H), 2.71 (s, 3H), 2.39 (s, 3H), 1.99 (s, 6H).

EXAMPLE 74

(2-{3-[6-(1-Methanesulfonyl-1-methyl-ethyl)-quinolin-8-yl]-benzyloxy}-phenyl)-phenyl-methanone

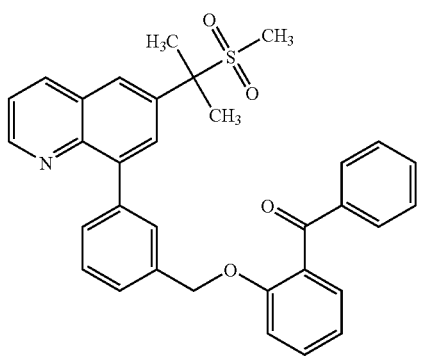

Prepared according to the procedure described in EXAMPLE 73 but using (2-hydroxy-phenyl)-phenyl-methanone as the starting material. The title compound was obtained as a foam.

¹H NMR (400 MHz, acetone-d₆): δ 8.86 (dd, 1H), 8.47 (dd, 1H), 8.29 (d, 1H), 8.01 (d, 1H), 7.64 (m, 2H), 7.58 (dd, 1H), 7.54 (m, 2H), 7.40–7.29 (m, 4H), 7.16 (m, 3H), 7.11 (t, 1H), 7.05 (d, 1H), 5.17 (s, 2H), 2.73 (s, 3H), 2.00 (s, 6H).

EXAMPLE 75

2-{3-[6-(1-Methanesulfonyl-1-methyl-ethyl)-quinolin-8-yl]-benzyloxy}-benzoic acid methyl ester

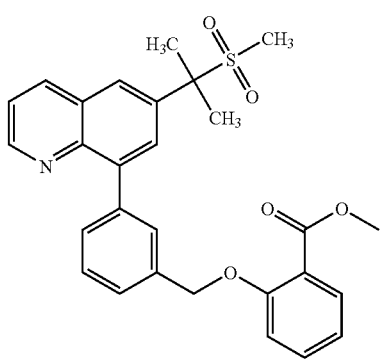

Prepared according to the procedure described in EXAMPLE 73, but using 2-hydroxy-benzoic acid methyl ester as the starting material. The title compound was obtained as a foam.

¹H NMR (400 MHz, acetone-d₆): δ 8.91 (dd, 1H), 8.45 (dd, 1H), 8.28 (d, 1H), 8.15 (d, 1H), 7.93 (s, 1H), 7.7 (dt, 1H), 7.62–7.49 (m, 4H), 7.28 (d, 1H), 7.03 (t, 1H), 5.33 (s, 2H), 3.75 (s, 3H), 2.71 (s, 3H), 2.00 (s, 6H).

EXAMPLE 76

8-[3-(2-Cyclopentyl-phenoxymethyl)-phenyl]-6-(1-methanesulfonyl-1-methyl-ethyl)-quinoline

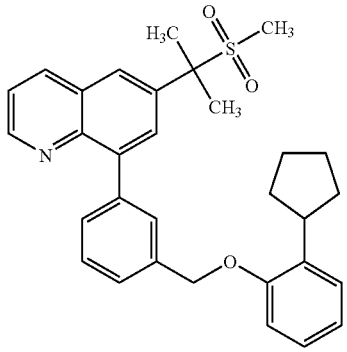

Prepared according to the procedure described in EXAMPLE 73, but using 2-cyclopentyl-phenol as the starting material. The title compound was obtained as a foam.

$^1$H NMR (400 MHz, acetone-d$_6$): δ 8.91 (dd, 1H), 8.45 (dd, 1H), 8.27 (d, 1H), 8.14 (d, 1H), 7.90 (s, 1H), 7.70 (dt, 1H), 7.59–7.50 (m, 3H), 7.23 (dd, 1H), 7.14 (dt, 1H), 7.07 (d, 1H), 6.90 (dt, 1H), 5.23 (s, 2H), 3.44 (m, 1H), 2.70 (s, 3H), 2.00 (m, 2H), 1.99 (s, 6H), 1.7 (m, 2H), 1.58 (m, 4H).

EXAMPLE 77

2'-{3-[6-(1-Methanesulfonyl-1-methyl-ethyl)-quinolin-8-yl]-benzyloxy}-biphenyl-2-ol

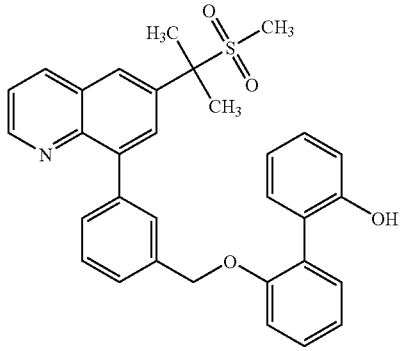

Prepared according to the procedure described in EXAMPLE 73, but using biphenyl-2,2'-diol as the starting material. The title compound was obtained as a foam.

$^1$H NMR (400 MHz, acetone-d$_6$): δ 8.88 (dd, 1H), 8.44 (dd, 1H), 8.27 (d, 1H), 8.07 (d, 1H), 7.76 (s, 1H), 7.73 (s, OH), 7.63 (d, 1H), 7.56 (dd, 1H), 7.43 (m, 2H), 7.33 (dt, 1H), 7.26 (dd, 1H), 7.19 (dd, 2H), 7.04 (m, 2H), 6.83 (d, 1H), 6.79 (dt, 1H), 5.24 (s, 2H), 2.71 (s, 3H), 1.99 (s, 6H).

EXAMPLE 78

8-[3-(2-Benzyl-phenoxymethyl)-phenyl]-6-(1-methanesulfonyl-1-methyl-ethyl)-quinoline

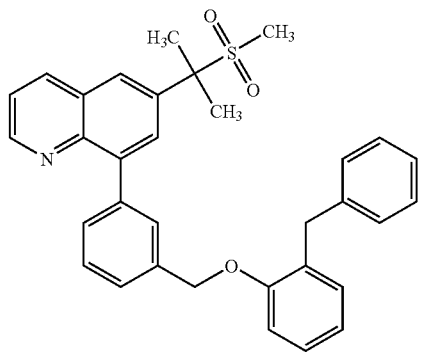

Prepared according to the procedure described in EXAMPLE 73, but using 2-benzyl-phenol as the starting material. The title compound was obtained as a foam.

$^1$H NMR (400 MHz, acetone-d$_6$): δ 8.88 (dd, 1H), 8.45 (dd, 1H), 8.28 (d, 1H), 8.12 (d, 1H), 7.82 (s, 1H), 7.67 (d, 1H), 7.56 (dd, 1H), 7.47 (m, 2H), 7.21–7.05 (m, 7H), 6.99 (t, 1H), 6.88 (dt, 1H), 5.22 (s, 2H), 4.01 (s, 2H), 2.69 (s, 3H), 1.98 (s, 6H).

EXAMPLE 79

3-(2-{3-[6-(1-Methanesulfonyl-1-methyl-ethyl)-quinolin-8-yl]-benzyloxy}-phenyl)-1-phenyl-propenone

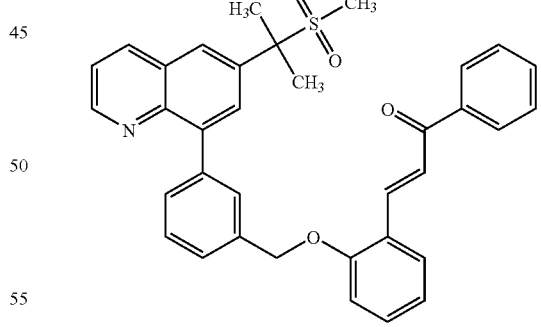

Prepared according to the procedure described in EXAMPLE 73, but using 3-(2-hydroxy-phenyl)-1-phenyl-propenone as the starting material. The title compound was obtained as a foam.

$^1$H NMR (400 MHz, acetone-d$_6$): δ 8.90 (dd, 1H), 8.43 (dd, 1H), 8.26 (d, 1H), 8.14 (d, 1H), 8.10 (d, 1H), 7.96 (d, 2H), 7.91 (m, 2H), 7.81 (dt, 1H), 7.66–7.51 (m, 4H), 7.45 (m, 3H), 7.30 (d, 1H), 7.06 (t, 1H), 5.38 (s, 2H), 2.67 (s, 3H), 1.95 (s, 6H).

EXAMPLE 80

6-(1-Methanesulfonyl-1-methyl-ethyl)-8-[3-(4-methyl-2-piperidin-1-ylmethyl-phenoxymethyl)-phenyl]-quinoline

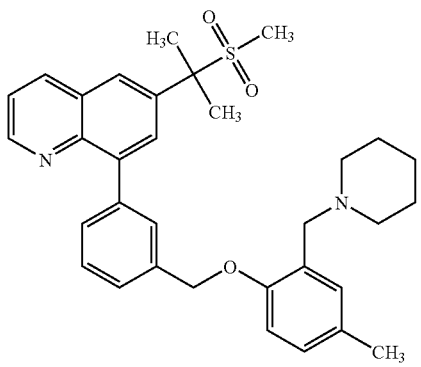

Prepared according to the procedure described in EXAMPLE 73, but using 4-methyl-2-piperidin-1-ylmethyl-phenol as the starting material. The title compound was obtained as a foam.

$^1$H NMR (400 MHz, acetone-d$_6$): δ 8.92 (dd, 1H), 8.44 (dd, 1H), 8.27 (d, 1H), 8.13 (d, 1H), 7.89 (s, 1H), 7.67 (d, 1H), 7.58–7.49 (m, 3H), 7.16 (s, 1H), 6.98 (m, 2H), 5.19 (s, 2H), 3.47 (s, 2H), 2.87 (m, 4H), 2.70 (s, 3H), 2.23 (s, 3H), 1.98 (s, 6H), 1.41 (m, 3H), 1.31 (m, 3H).

EXAMPLE 81

8-[3-(2-Benzothiazol-2-yl-phenoxymethyl)-phenyl]-6-(1-methanesulfonyl-1-methyl-ethyl)-quinoline

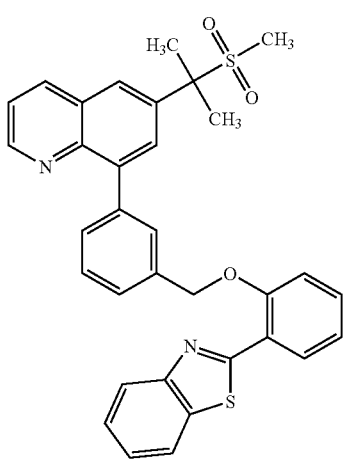

Prepared according to the procedure described in EXAMPLE 73, but using 2-benzothiazol-2-yl-phenol as the starting material. The title compound was obtained as a foam.

$^1$H NMR (400 MHz, acetone-d$_6$): δ 8.86 (dd, 1H), 8.56 (dd, 1H), 8.25 (d, 1H), 8.14 (d, 1H), 8.03 (s, 1H), 8.00 (d, 1H), 7.96 (d, 1H), 7.76 (d, 1H), 7.69 (d, 1H), 7.57–7.49 (m, 4H), 7.44 (d, 1H), 7.42 (dd, 1H), 7.38 (dt, 1H), 7.16 (dt, 1H), 5.59 (s, 2H), 2.66 (s, 3H), 1.93 (s, 6H).

EXAMPLE 82

1-(2-{3-[6-(1-Methanesulfonyl-1-methyl-ethyl)-quinolin-8-yl]-benzyloxy}-phenyl)-3-phenyl propan-1-one

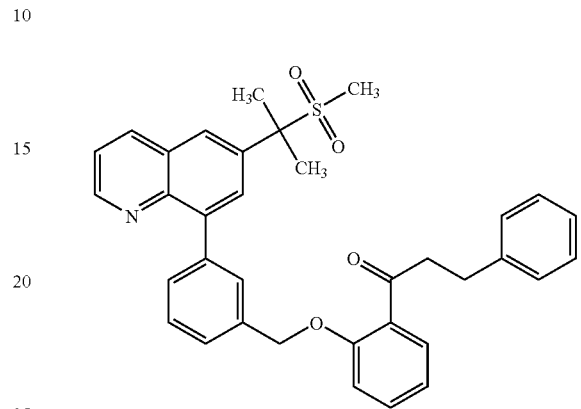

Prepared according to the procedure described in EXAMPLE 73, but using 1-(2-hydroxy-phenyl)-3-phenyl-propan-1-one as the starting material. The title compound was obtained as a foam.

$^1$H NMR (400 MHz, acetone-d$_6$): δ 8.89 (dd, 1H), 8.44 (dd, 1H), 8.27 (d, 1H), 8.12 (d, 1H), 7.94 (s, 1H), 7.74 (d, 1H), 7.62–7.47 (m, 5H), 7.31 (d, 1H), 7.11–7.00 (m, 6H), 5.36 (s, 2H), 3.34 (t, 2H), 2.89 (t, 2H), 2.67 (s, 3H), 1.96 (s, 6H).

EXAMPLE 83

6-(1-Methanesulfonyl-1-methyl-ethyl)-8-[3-(2-morpholin-4-yl-phenoxymethyl)-phenyl]-quinoline

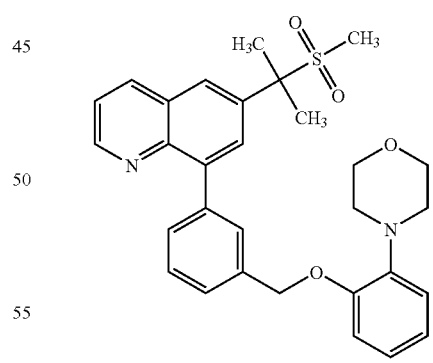

Prepared according to the procedure described in EXAMPLE 73, but using 2-morpholin-4-yl-phenol as the starting material. The title compound was obtained as a foam.

$^1$H NMR (400 MHz, acetone-d$_6$): δ 8.91 (dd, 1H), 8.45 (dd, 1H), 8.28 (d, 1H), 8.14 (d, 1H), 7.89 (s, 1H), 7.67 (d, 1H), 7.58–7.50 (m, 3H), 7.09 (d, 1H), 6.94 (m, 3H), 5.26 (s, 2H), 3.65 (t, 4H), 3.04 (t, 4H), 2.70 (s, 3H), 1.99 (s, 6H).

EXAMPLE 84

6-(1-Methanesulfonyl-1-methyl-ethyl)-8-(3-(2-methoxy-phenoxymethyl)-phenyl]-quinoline

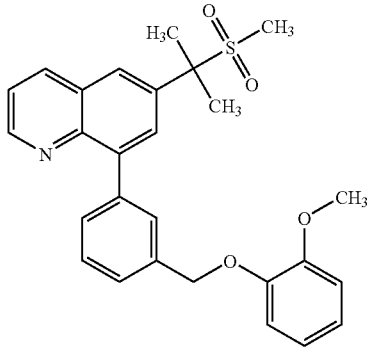

Prepared according to the procedure described in EXAMPLE 73, but using 2-methoxy-phenol as the starting material. The title compound was obtained as a foam.

$^1$H NMR (400 MHz, acetone-d$_6$): δ 8.91 (dd, 1H), 8.44 (dd, 1H), 8.27 (d, 1H), 8.13 (d, 1H), 7.86 (s, 1H), 7.69 (d, 1H), 7.58–7.48 (m, 3H), 7.09 (dd, 1H), 6.97 (dd, 1H), 6.92–6.84 (m, 2H), 5.2 (s, 2H), 3.8 (s, 3H), 2.7 (s, 3H), 1.99 (s, 6H).

EXAMPLE 85

6-(1-Methanesulfonyl-1-methyl-ethyl)-8-[3-(2-trifluoromethyl-phenoxymethyl)-phenyl]-quinoline

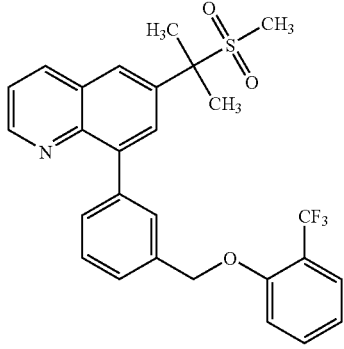

Prepared according to the procedure described in EXAMPLE 73, but using 2-trifluoromethyl-phenol as the starting material. The title compound was obtained as a foam.

$^1$H NMR (400 MHz, acetone-d$_6$): δ 8.91 (dd, 1H), 8.45 (dd, 1H), 8.28 (d, 1H), 8.13 (d, 1H), 7.9 (s, 1H), 7.72 (d, 1H), 7.65–7.50 (m, 5H), 7.39 (d, 1H), 7.10 (t, 1H), 5.4 (s, 2H), 2.70 (s, 3H), 1.99 (s, 6H).

EXAMPLE 86

2-{3-[6-(1-Methanesulfonyl-1-methyl-ethyl)-quinolin-8-yl]-benzyloxy)}-benzonitrile

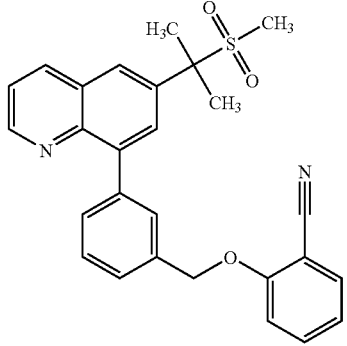

Prepared according to the procedure described in EXAMPLE 73, but using 2-hydroxy-benzonitrile as the starting material. The title compound was obtained as a foam.

$^1$H NMR (400 MHz, acetone-d$_6$): δ 8.91 (dd, 1H), 8.44 (dd, 1H), 8.28 (d, 1H), 8.14 (d, 1H), 7.92 (s, 1H), 7.73 (d, 1H), 7.69–7.64 (m, 2H), 7.59–7.51 (m, 3H), 7.38 (d, 1H), 7.11 (t, 1H), 5.43 (s, 2H), 2.70 (s, 3H), 1.99 (s, 6H).

EXAMPLE 87

8-[3-(2-Allyl-6-methoxy-phenoxymethyl)-phenyl]-6-(1-methanesulfonyl-1-methyl-ethyl)-quinoline

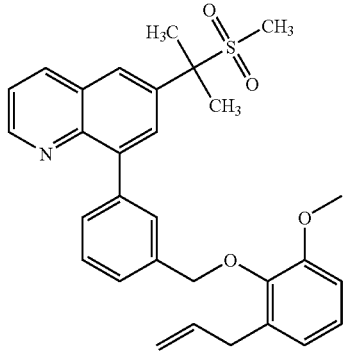

Prepared according to the procedure described in EXAMPLE 73, but using 2-allyl-6-methoxy-phenol as the starting material. The title compound was obtained as a foam.

$^1$H NMR (400 MHz, acetone-d$_6$): δ 8.92 (dd, 1H), 8.44 (dd, 1H), 8.27 (d, 1H), 8.13 (d, 1H), 7.86 (s, 1H), 7.70 (d, 1H), 7.58–7.47 (m, 3H), 7.00 (t, 1H), 6.92 (d, 1H), 6.76 (dd, 1H), 5.92 (m, 1H), 5.10 (s, 2H), 5.03–4.93 (m, 2H), 3.88 (s, 3H), 3.41 (d, 2H), 2.71 (s, 3H), 1.99 (s, 6H).

EXAMPLE 88

8-[3-(2-Benzyloxy-phenoxymethyl)-phenyl]-6-(1-methanesulfonyl-1-methyl-ethyl)-quinoline

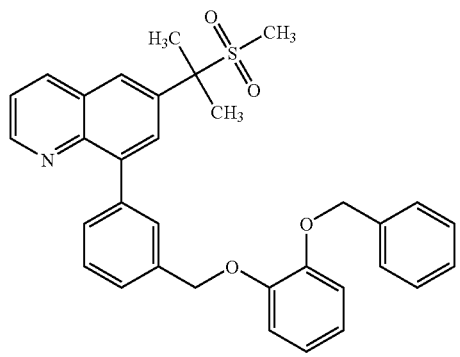

Prepared according to the procedure described in EXAMPLE 73, but using 2-benzyloxy-phenol as the starting material. The title compound was obtained as a foam.

$^1$H NMR (400 MHz, acetone-$d_6$): δ 8.88 (dd, 1H), 8.44 (dd, 1H), 8.27 (d, 1H), 8.11 (d, 1H), 7.90 (s, 1H), 7.67 (d, 1H), 7.55 (m, 2H), 7.50 (d, 1H), 7.42 (m, 2H), 7.21 (m, 3H), 7.14 (dd, 1H), 7.04 (dd, 1H), 6.90 (m, 2H), 5.26 (s, 2H), 5.13 (s, 2H), 2.67 (s, 3H), 1.96 (s, 6H).

EXAMPLE 89

(2-{3-[6-(1-Methanesulfonyl-1-methyl-ethyl)-quinolin-8-yl]-benzyloxy}-phenyl)-(1-phenyl-1H-pyrazol-4-yl)-methanone

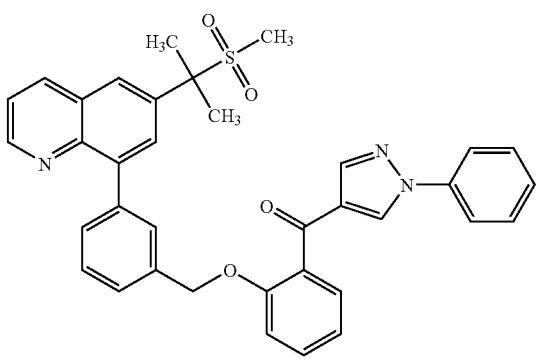

Prepared according to the procedure described in EXAMPLE 73, but using (2-hydroxy-phenyl)-(1-phenyl-1H-pyrazol-4-yl)-methanone as the starting material. The title compound was obtained as a foam.

$^1$H NMR (400 MHz, acetone-$d_6$): δ 8.82 (dd, 1H), 8.63 (s, 1H), 8.39 (dd, 1H), 8.22 (d, 1H), 8.03 (d, 1H), 7.97 (s, 1H), 7.70 (d, 1H), 7.69 (d, 1H), 7.52 (m, 3H), 7.44 (dd, 1H), 7.41–7.28 (m, 7H), 7.09 (t, 1H), 5.29 (s, 2H), 2.68 (s, 3H), 1.97 (s, 6H).

EXAMPLE 90

6-(1-Methanesulfonyl-1-methyl-ethyl)-8-[3-(2-methanesulfonyl-phenoxymethyl)-phenyl]-quinoline

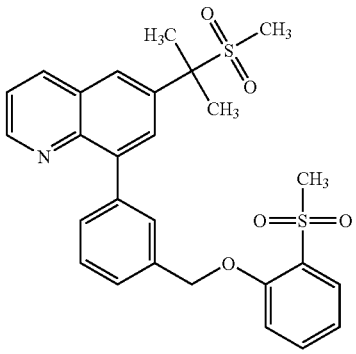

Prepared according to the procedure described in EXAMPLE 17 (Step 5), but using 6-(1-Methanesulfonyl-1-methyl-ethyl)-8-[3-(2-methylsulfanyl-phenoxymethyl)-phenyl]-quinoline (EXAMPLE 73) as the starting material. Flash chromatography (Hex:EtOAc; 40 to 100% in 15 min) afforded the title compound as a foam.

$^1$H NMR (400 MHz, acetone-$d_6$): δ 8.90 (dd, 1H), 8.42 (dd, 1H), 8.27 (d, 1H), 8.15 (d, 1H), 7.98 (s, 1H), 7.90 (dd, 1H), 7.75 (d, 1H), 7.64 (m, 2H), 7.54 (m, 2H), 7.40 (d, 1H), 7.15 (t, 1H), 5.44 (s, 2H), 3.25 (s, 3H), 2.70 (s, 3H), 1.98 (s, 6H).

EXAMPLE 91

Cyclopropyl-(2-{3-[6-(1-methanesulfonyl-1-methyl-ethyl)-quinolin-8-yl]-benzyloxy}-phenyl)-phenyl-methanol

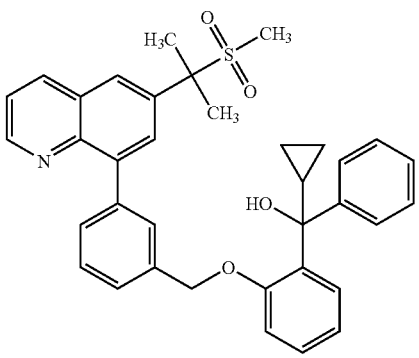

To solution of (2-{3-[6-(1-Methanesulfonyl-1-methyl-ethyl)-quinolin-8-yl]-benzyloxy}-phenyl)-phenyl-methanone (EXAMPLE 74) (1.0 eq) in THF (0.03M) was added CeCl$_3$ (2.7 eq). The resulting mixture was stirred for 1 h, then cooled to −78° C. Cyclopropyl magnesium bromide (0.24M in THF; 4.8 eq) was added and the final mixture was allowed to warm-up to room temperature. After stirring for 1 h the mixture was poured in saturated aqueous NH$_4$Cl and extracted with EtOAc (2×). The combined organic extracts were washed with brine, dried over MgSO$_4$, filtered and concentrated. Flash chromatography (Hex:EtOAc; 40 to 100% in 15 min) afforded the title compound as a foam.

$^1$H NMR (400 MHz, acetone-$d_6$): δ 8.89 (dd, 1H), 8.46 (dd, 1H), 8.30 (d, 1H), 8.06 (d, 1H), 7.92 (dd, 1H), 7.57 (m, 2H), 7.32 (m, 3H), 7.17 (m, 2H), 7.10 (d, 1H), 7.05 (t, 1H), 6.88 (m, 3H), 6.74 (t, 1H), 5.00 (d, 1H), 4.88 (d, 1H), 4.29 (s, OH), 2.72 (s, 3H), 2.00 (s, 6H), 1.67 (m, 1H), 0.68 (m, 1H), 0.43 (m, 3H).

EXAMPLE 92

Dicyclopropyl-(2-{3-[6-(1-methanesulfonyl-1-methyl-ethyl)-quinolin-8-yl]-benzyloxy}-phenyl)-methanol

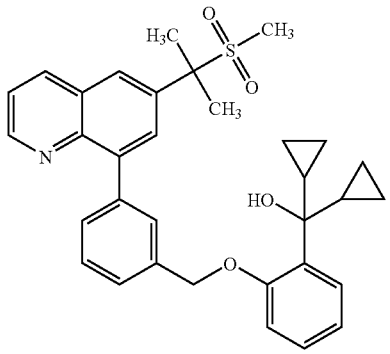

Prepared according to the procedure described in EXAMPLE 91, but using 2-{3-[6-(1-methanesulfonyl-1-methyl-ethyl)-quinolin-8-yl]-benzyloxy}-benzoic acid methyl ester (EXAMPLE 75) as the starting material. The title compound was obtained as a foam.

$^1$H NMR (400 MHz, acetone-$d_6$): δ 8.91 (dd, 1H), 8.43 (dd, 1H), 8.27 (d, 1H), 8.14 (d, 1H), 7.94 (s, 1H), 7.74 (d, 1H), 7.60–7.50 (m, 4H), 7.24–7.15 (m, 2H), 6.93 (dt, 1H), 5.30 (s, 2H), 3.94 (s, OH), 2.69 (s, 3H), 1.98 (s, 6H), 1.60 (m, 2H), 0.61 (m, 2H), 0.30 (m, 4H), 0.18 (m, 2H).

EXAMPLE 93

1-Cyclopropyl-1-(2-{3-[6-(1-methanesulfonyl-1-methyl-ethyl)-quinolin-8-yl]-benzyloxy}-phenyl)-3-phenyl-propan-1-ol

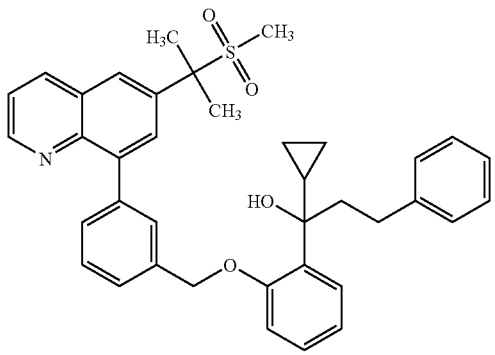

Prepared according to the procedure described in EXAMPLE 91, but using 1-(2-{3-[6-(1-methanesulfonyl-1-methyl-ethyl)-quinolin-8-yl]-benzyloxy}-phenyl)-3-phenyl-propan-1-one (EXAMPLE 82) as the starting material. The title compound was obtained as a foam.

$^1$H NMR (400 MHz, acetone-$d_6$): δ 8.87 (dd, 1H), 8.42 (dd, 1H), 8.26 (d, 1H), 8.12 (d, 1H), 7.95 (s, 1H), 7.71 (d, 1H), 7.67 (d, 1H), 7.56–7.48 (m, 3H), 7.24 (dt, 1H), 7.16 (d, 1H), 7.03–6.94 (m, 6H), 5.31 (s, 2H), 3.80 (s, OH), 2.8–2.6 (m, 2H), 2.66 (s, 3H), 2.35 (m, 1H), 2.11 (m, 1H), 1.96 (s, 3H), 1.95 (s, 3H), 1.75 (m, 1H), 0.64 (m, 1H), 0.30 (m, 2H), 0.12 (m, 1H).

EXAMPLE 94

8-[3-(4,6-Dimethyl-pyrimidin-2-ylsulfanylmethyl)-phenyl]-6-pyridin-4-ylmethyl-quinoline

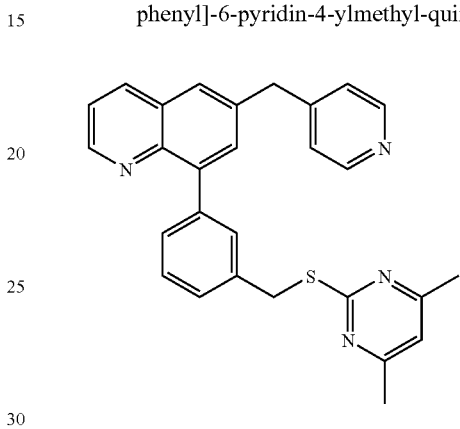

To a solution of Quinoline 8 (1.0 eq) in $CH_2Cl_2$/DMF (1/1; 0.07M) was added 4,6-dimethyl-pyrimidine-2-thiol (2.0 eq) and diisopropyl-ethyl amine (3.0 eq). The final resulting mixture was stirred for 12 h, poured in saturated aqueous $NH_4Cl$ and extracted with EtOAc (2×). The combined organic extracts were washed with brine, dried over $MgSO_4$, filtered and concentrated. Flash chromatography (Hex:EtOH; 9:1) afforded the title compound as a yellow solid.

$^1$H NMR (400 MHz, $CDCl_3$): δ 8.88 (dd, 1H), 8.52 (dd, 2H), 8.12 (dd, 1H), 7.72 (s, 1H), 7.54 (d, 3H), 7.47 (d, 1H), 7.38 (m, 2H), 7.16 (dd, 2H), 6.68 (s, 1H), 4.44 (s, 2H), 4.17 (s, 2H), 2.33 (s, 6H).

EXAMPLE 95

6-Pyridin-4-ylmethyl-8-[3-(pyridin-4-ylsulfanylmethyl)-phenyl]-quinoline

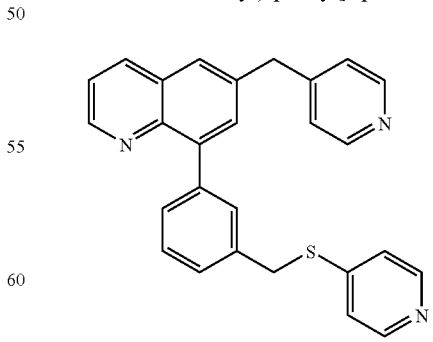

Prepared according to the procedure described in EXAMPLE 94, but using pyridine-4-thiol as the starting material. The title compound was obtained as a yellow foam.

¹H NMR (300 MHz, CDCl₃): δ 8.86 (dd, 1H), 8.53 (dd, 2H), 8.35 (dd, 2H), 8.12 (dd, 1H), 7.68 (s, 1H), 7.58 (t, 2H), 7.48 (d, 1H), 7.41 (m, 3H), 7.12 (m, 4H), 4.28 (s, 2H), 4.17 (s, 2H).

EXAMPLE 96

6-Isopropyl-8-(3-phenylsulfanylmethyl-phenyl)-quinoline

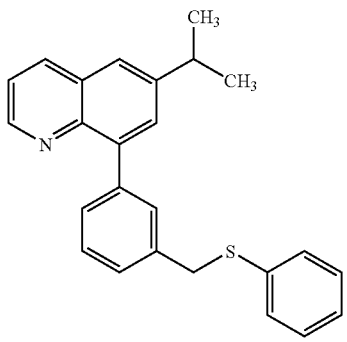

Prepared according to the procedure described in EXAMPLE 94, but using Quinoline 20 and benzenethiol as the starting materials. The title compound was obtained as a yellow foam.

¹H NMR (500 MHz, acetone-d₆): δ 8.79 (dd, 1H), 8.28 (dd, 1H), 7.77 (d, 1H), 7.66 (s, 1H), 7.64 (dd, 2H), 7.48 (q, 1H), 7.38 (dd, 4H), 7.27 (t, 2H), 7.18 (t, 1H), 4.30 (s, 2H), 3.14 (m, 1H), 1.38 (d, 6H).

LRMS (CI) 370 (M+H)⁺

EXAMPLE 97

8-(3-Benzenesulfonylmethyl-phenyl)-6-isopropyl-quinoline

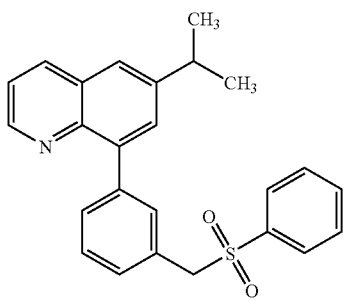

Prepared according to the procedure described in EXAMPLE 17 (Step 5) but using 6-isopropyl-8-(3-phenyl-sulfanylmethyl-phenyl)-quinoline (EXAMPLE 96) as the starting material. The title compound was obtained as a white solid.

¹H NMR (500 MHz, acetone-d₆): δ 8.79 (dd, 1H), 8.28 (dd, 1H), 7.78 (t, 3H), 7.72 (d, 1H), 7.58 (t, 2H), 7.48 (q, 1H), 7.43 (d, 1H), 7.38 (t, 2H), 7.25 (d, 1H), 4.61 (s, 2H), 3.15 (m, 1H), 1.37 (d, 6H).

LRMS (CI) 402 (M+H)⁺

EXAMPLE 98

6-Isopropyl-8-[3-(pyridin-4-ylsulfanylmethyl)-phenyl]-quinoline

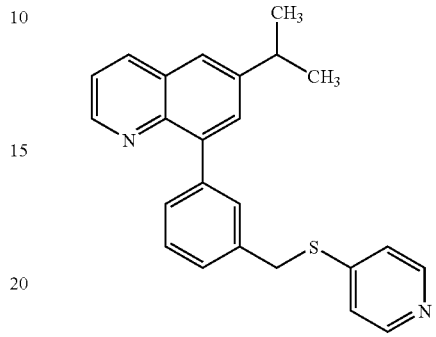

Prepared according to the procedure described in EXAMPLE 96, but using pyridine-4-thiol as the starting material. The title compound was obtained as a foam.

¹H NMR (300 MHz, acetone-d₆): δ 8.81 (dd, 1H), 8.37 (d, 2H), 8.28 (dd, 1H), 7.82 (d, 1H), 7.78 (d, 1H), 7.68 (d, 1H), 7.62 (d, 1H), 7.46 (m, 3H), 7.31 (dd, 2H), 4.43 (s, 2H), 3.12 (m, 1H), 1.38 (d, 6H).

EXAMPLE 99

6-(1-Methanesulfonyl-1-methyl-ethyl)-8-[3-(5-methylsulfanyl-[1,3,4]thiadiazol-2-ylsulfanylmethyl)-phenyl]-quinoline

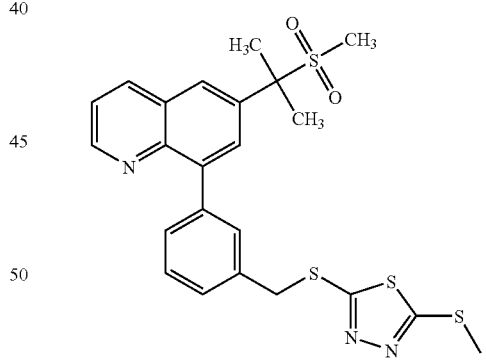

To solution of Quinoline 12 (1.0 eq) and 5-methylsulfanyl-[1,3,4]thiadiazole-2-thiol (1.0 eq) in DMSO (0.09M) was added aqueous KOH (2.0M; 1.0 eq). The resulting mixture was stirred for 12 h, poured in water and extracted with EtOAc. The combined organic extracts were washed with brine and concentrated. Flash chromatography (Hex: EtOAc; 40 to 100% in 15 min) afforded the title compound as a foam.

¹H NMR (400 MHz, acetone-d₆): δ 8.91 (dd, 1H), 8.45 (dd, 1H), 8.28 (d, 1H), 8.11 (d, 1H), 7.85 (s, 1H), 7.68 (d, 1H), 7.56 (dd, 1H), 7.53 (d, 1H), 7.46 (t, 1H), 4.64 (s, 2H), 2.74 (s, 3H), 2.71 (s, 3H), 1.98 (s, 6H).

EXAMPLE 100

6-(1-Methanesulfonyl-1-methyl-ethyl)-8-[3-(2,3,5,6-tetrachloro-pyridin-4-ylsulfanylmethyl)-phenyl]-quinoline

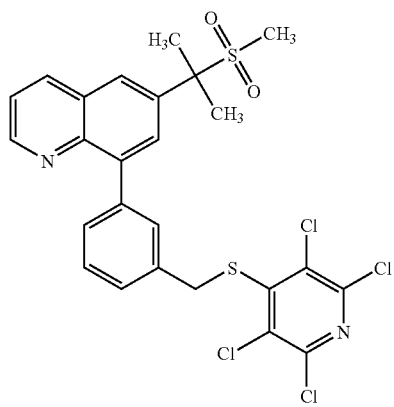

Prepared according to the procedure described in EXAMPLE 99, but using 2,3,5,6-tetrachloro-pyridine-4-thiol as the starting material. The title compound was obtained as a foam.

$^1$H NMR (400 MHz, acetone-$d_6$): δ 8.92 (dd, 1H), 8.46 (dd, 1H), 8.28 (d, 1H), 8.07 (d, 1H), 7.66 (s, 1H), 7.61–7.57 (m, 2H), 7.72–7.38 (m, 2H), 4.51 (s, 2H), 2.71 (s, 3H), 1.99 (s, 6H).

EXAMPLE 101

6-(1-Methanesulfonyl-1-methyl-ethyl)-8-[3-([1,3,4]thiadiazol-2-ylsulfanylmethyl)-phenyl]-quinoline

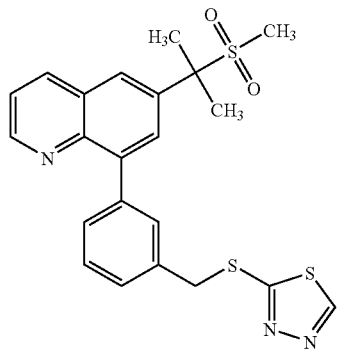

Prepared according to the procedure described in EXAMPLE 99, but using [1,3,4]thiadiazole-2-thiol as the starting material. The title compound was obtained as a foam.

$^1$H NMR (400 MHz, acetone-$d_6$): δ 9.36 (s, 1H), 8.91 (dd, 1H), 8.45 (dd, 1H), 8.27 (d, 1H), 8.10 (d, 1H), 7.87 (s, 1H), 7.68 (d, 1H), 7.58–7.55 (m, 2H), 7.47 (t, 1H), 4.72 (s, 2H), 2.71 (s, 3H), 1.99 (s, 6H).

EXAMPLE 102

6-(1-Methanesulfonyl-1-methyl-ethyl)-8-[3-(4-nitro-phenylsulfanylmethyl)-phenyl]-quinoline

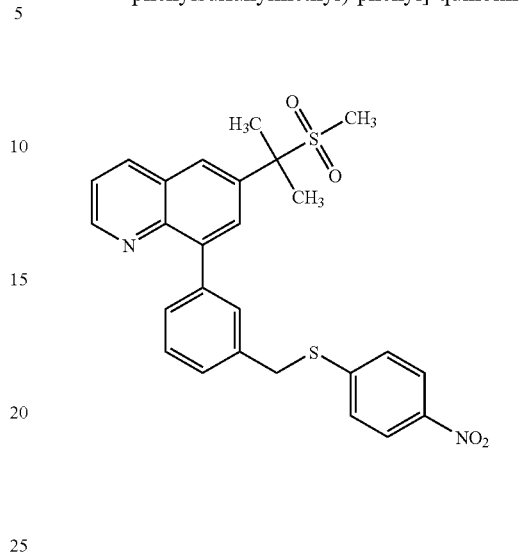

Prepared according to the procedure described in EXAMPLE 99, but using 4-nitro-benzenethiol as the starting material. The title compound was obtained as a foam.

$^1$H NMR (400 MHz, acetone-$d_6$): δ 8.91 (dd, 1H), 8.45 (dd, 1H), 8.27 (d, 1H), 8.16 (d, 2H), 8.10 (d, 1H), 7.85 (s, 1H), 7.66 (d, 1H), 7.61 (d, 2H), 7.58 (dd, 1H), 7.55 (d, 1H), 7.46 (t, 1H), 4.53 (s, 2H), 2.70 (s, 3H), 1.98 (s, 6H).

EXAMPLE 103

6-(1-Methanesulfonyl-1-methyl-ethyl)-8-[3-(pyrimidin-2-ylsulfanylmethyl)-phenyl]-quinoline

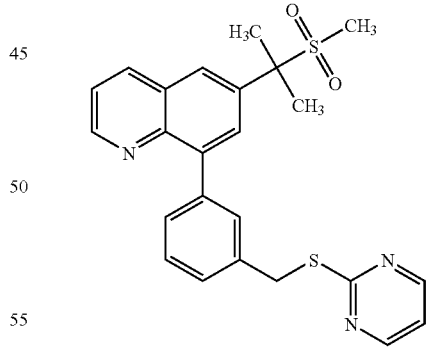

Prepared according to the procedure described in EXAMPLE 99, but using pyrimidine-2-thiol as the starting material. The title compound was obtained as a foam.

$^1$H NMR (400 MHz, acetone-$d_6$): δ 8.89 (dd, 1H), 8.62 (d, 2H), 8.43 (dd, 1H), 8.26 (d, 1H), 8.10 (d, 1H), 7.85 (s, 1H), 7.63 (d, 1H), 7.55 (dd, 1H), 7.51 (d, 1H), 7.42 (t, 1H), 7.18 (t, 1H), 4.53 (s, 2H), 2.70 (s, 3H), 1.98 (s, 6H).

EXAMPLE 104

6-(1-Methanesulfonyl-1-methyl-ethyl)-8-[3-(4-methyl-4H-[1,2,4]triazol-3-ylsulfanylmethyl)-phenyl]-quinoline

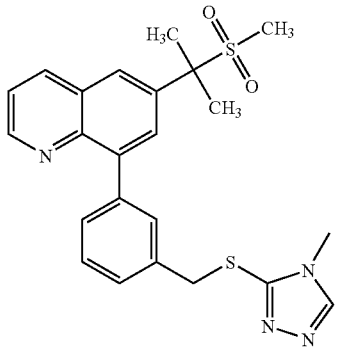

Prepared according to the procedure described in EXAMPLE 99, but using 4-methyl-4H-[1,2,4]triazole-3-thiol as the starting material. The title compound was obtained as a foam.

$^1$H NMR (400 MHz, acetone-d$_6$): δ 8.92 (dd, 1H), 8.44 (dd, 1H), 8.31 (s, 1H), 8.26 (d, 1H), 8.05 (d, 1H), 7.65–7.60 (m, 2H), 7.56 (dd, 1H), 7.43–7.38 (m, 2H), 4.40 (s, 2H), 3.45 (s, 3H), 2.73 (s, 3H), 1.99 (s, 6H).

EXAMPLE 105

6-(1-Methanesulfonyl-1-methyl-ethyl)-8-[3-(1H-pyrazolo[3,4-d]pyrimidin-4-ylsulfanylmethyl)-phenyl]-quinoline

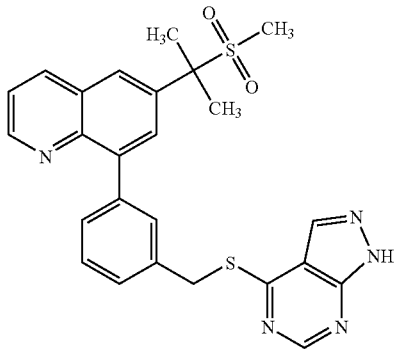

Prepared according to the procedure described in EXAMPLE 99, but using 1H-pyrazolo[3,4-d]pyrimidine-4-thiol as the starting material. The title compound was obtained as a foam.

$^1$H NMR (400 MHz, acetone-d$_6$): δ 8.87 (dd, 1H), 8.76 (s, 1H), 8.43 (dd, 1H), 8.26 (d, 1H), 8.18 (s, 1H), 8.11 (d, 1H), 7 (s, 1H), 7.91 (s, 1H), 7.65 (d, 1H), 7.57–7.54 (m, 2H), 7.44 (t, 1H), 4.81 (s, 2H), 2.69 (s, 3H), 1.97 (s, 6H).

EXAMPLE 106

6-(1-Methanesulfonyl-1-methyl-ethyl)-8-[3-(5-phenyl-[1,3,4]oxadiazol-2-ylsulfanylmethyl)-phenyl]-quinoline

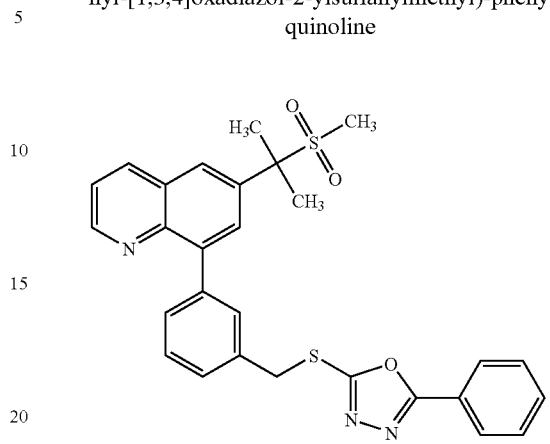

Prepared according to the procedure described in EXAMPLE 99, but using 5-phenyl-[1,3,4]oxadiazole-2-thiol as the starting material. The title compound was obtained as a foam.

$^1$H NMR (400 MHz, acetone-d$_6$): δ 8.88 (dd, 1H), 8.44 (dd, 1H), 8.27 (d, 1H), 8.11 (d, 1H), 7.98 (dd, 2H), 7.93 (app s, 1H), 7.69 (d, 1H), 7.61–7.46 (m, 6H), 4.71 (s, 2H), 2.69 (s, 3H), 1.97 (s, 6H).

EXAMPLE 107

2-{3-[6-(1-Methanesulfonyl-1-methyl-ethyl)-quinolin-8-yl]-benzylsulfanyl}-nicotinic acid

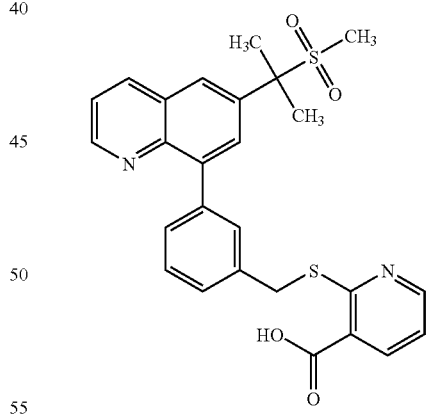

Prepared according to the procedure described in EXAMPLE 99, but using 2-mercapto-nicotinic acid as the starting material and 2 equivalent of KOH.

The title compound was obtained as a foam.

$^1$H NMR (400 MHz, acetone-d$_6$): δ 8.89 (dd, 1H), 8.69 (dd, 1H), 8.43 (dd, 1H), 8.30 (dd, 1H), 8.26 (d, 1H), 8.10 (d, 1H), 7.83 (s, 1H), 7.61 (d, 1H), 7.55 (dd, 1H), 7.50 (dd, 1H), 7.41 (t, 1H), 7.24 (dd, 1H), 4.52 (s, 2H), 2.69 (s, 3H), 1.98 (s, 6H).

EXAMPLE 108

2-{3-[6-(1-Methanesulfonyl-1-methyl-ethyl)-quinolin-8-yl]-benzylsulfanyl}-4,6-dimethyl-nicotinonitrile

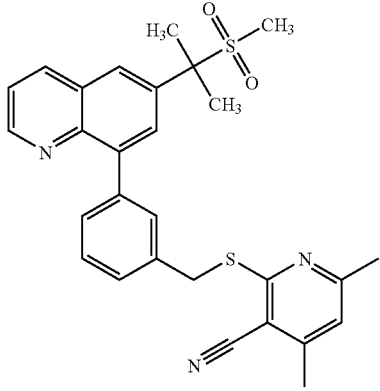

Prepared according to the procedure described in EXAMPLE 99, but using 2-mercapto-4,6-dimethyl-nicotinonitrile as the starting material. The title compound was obtained as a foam.
$^1$H NMR (400 MHz, acetone-d$_6$): δ 8.88 (dd, 1H), 8.44 (dd, 1H), 8.26 (d, 1H), 8.10 (d, 1H), 7.85 (s, 1H), 7.61 (d, 1H), 7.56 (s, 1H), 7.52 (d, 1H), 7.42 (t, 1H), 7.03 (s, 1H), 4.65 (s, 2H), 2.69 (s, 3H), 2.50 (s, 3H), 2.42 (s, 3H), 1.98 (s, 6H).

EXAMPLE 109

8-[3-(3-Chloro-phenylsulfanylmethyl)-phenyl]-6-(1-methanesulfonyl-1-methyl-ethyl)-quinoline

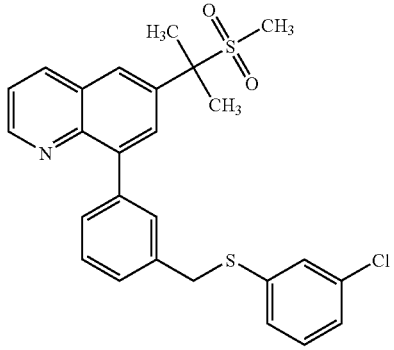

Prepared according to the procedure described in EXAMPLE 99, but using 3-chloro-benzenethiol as the starting material. The title compound was obtained as a foam.
$^1$H NMR (400 MHz, acetone-d$_6$): δ 8.91 (dd, 1H), 8.44 (dd, 1H), 8.27 (d, 1H), 8.09 (d, 1H), 7.78 (s, 1H), 7.62 (app dt, 1H), 7.56 (dd, 1H), 7.46–7.40 (m, 3H), 7.36–7.28 (m, 2H), 7.19 (app dt, 1H), 4.38 (s, 2H), 2.70 (s, 3H), 1.98 (s, 6H).

EXAMPLE 110

6-(1-Methanesulfonyl-1-methyl-ethyl)-8-[3-(6-nitro-benzothiazol-2-ylsulfanylmethyl)-phenyl]-quinoline

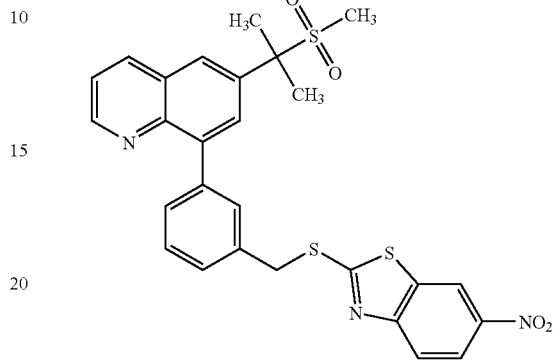

Prepared according to the procedure described in EXAMPLE 99, but using 6-nitro-benzothiazole-2-thiol as the starting material. The title compound was obtained as a foam.
$^1$H NMR (400 MHz, acetone-d$_6$): δ 8.97 (d, 1H), 8.85 (dd, 1H), 8.44 (dd, 1H), 8.33 (dd, 1H), 8.27 (d, 1H), 8.12 (d, 1H), 8.04 (d, 1H), 7.95 (s, 1H), 7.69 (d, 1H), 7.61 (d, 1H), 7.55 (dd, 1H), 7.48 (t, 1H), 4.86 (s, 2H), 2.70 (s, 3H), 1.97 (s, 6H).

EXAMPLE 111

2-{3-[6-(1-Methanesulfonyl-1-methyl-ethyl)-quinolin-8-yl]-benzylsulfanyl}-benzoic acid methyl ester

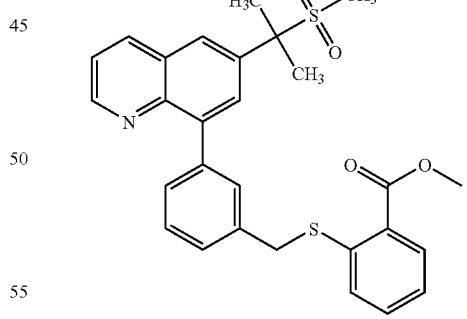

Prepared according to the procedure described in EXAMPLE 99, but using 2-mercapto-benzoic acid methyl ester as the starting material. The title compound was obtained as a foam.
$^1$H NMR (400 MHz, acetone-d$_6$): δ 8.91 (dd, 1H), 8.44 (dd, 1H), 8.27 (d, 1H), 8.11 (d, 1H), 7.91 (dd, 1H), 7.83 (s, 1H), 7.65–7.61 (m, 2H), 7.57–7.51 (m, 3H), 7.45 (t, 1H), 7.23 (dt, 1H), 5.29 (s, 2H), 3.83 (s, 3H), 2.70 (s, 3H), 1.98 (s, 6H).

EXAMPLE 112

6-(1-Methanesulfonyl-1-methyl-ethyl)-8-[3-(pyridin-4-ylsulfanylmethyl)-phenyl]-quinoline

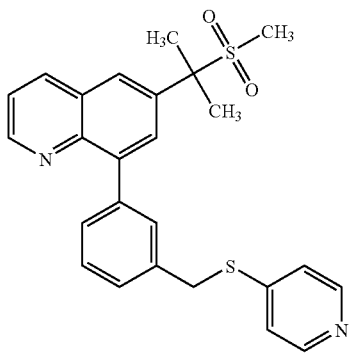

Prepared according to the procedure described in EXAMPLE 99, but using pyridine-4-thiol as the starting material. The title compound was obtained as a foam.

$^1$H NMR (500 MHz, acetone-$d_6$): δ 8.90 (dd, 1H), 8.45 (dd, 1H), 8.37 (d, 2H), 8.27 (d, 1H), 8.11 (d, 1H), 7.85 (s, 1H), 7.65 (d, 1H), 7.57 (dd, 1H), 7.53 (d, 1H), 7.46 (t, 1H), 7.32 (d, 2H), 4.46 (s, 2H), 2.70 (s, 3H), 1.98 (s, 6H).

EXAMPLE 113

8-[3-(2,6-Dichloro-phenylsulfanylmethyl)-phenyl]-6-(1-methanesulfonyl-1-methyl-ethyl)-quinoline

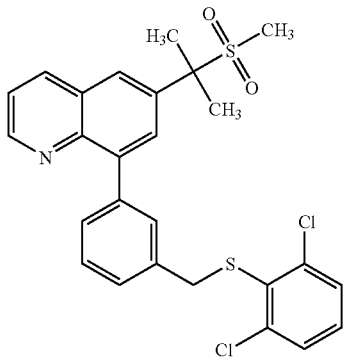

Prepared according to the procedure described in EXAMPLE 99, but using 2,6-dichloro-benzenethiol as the starting material. The title compound was obtained as a foam.

$^1$H NMR (500 MHz, acetone-$d_6$): δ 8.90 (dd, 1H), 8.43 (dd, 1H), 8.26 (d, 1H), 8.03 (d, 1H), 7.59–7.54 (m, 3H), 7.46 (d, 2H), 7.36–7.30 (m, 3H), 4.26 (s, 2H), 2.71 (s, 3H), 1.99 (s, 6H).

EXAMPLE 114

8-[3-(2-Chloro-phenylsulfanylmethyl)-phenyl]-6-(1-methanesulfonyl-1-methyl-ethyl)-quinoline

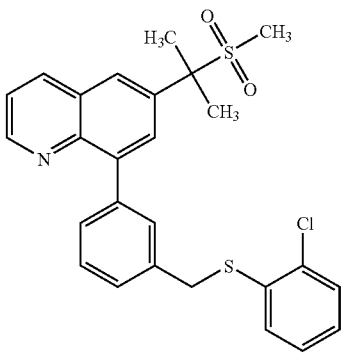

Prepared according to the procedure described in EXAMPLE 99, but using 2-chloro-benzenethiol as the starting material. The title compound was obtained as a foam.

$^1$H NMR (500, acetone-$d_6$): δ 8.91 (dd, 1H), 8.44 (dd, 1H), 8.27 (d, 1H), 8.10 (d, 1H), 7.82 (s, 1H), 7.64 (d, 1H), 7.56 (dd, 1H), 7.51 (app dt, 2H), 7.45 (d, 1H), 7.41 (dd, 1H), 7.30 (dt, 1H), 7.18 (dt, 1H), 4.37 (s, 2H), 2.70 (s, 3H), 1.98 (s, 6H).

EXAMPLE 115

2-{3-[6-(1-Methanesulfonyl-1-methyl-ethyl)-quinolin-8-yl]-benzylsulfanyl}-3H-quinazolin-4-one

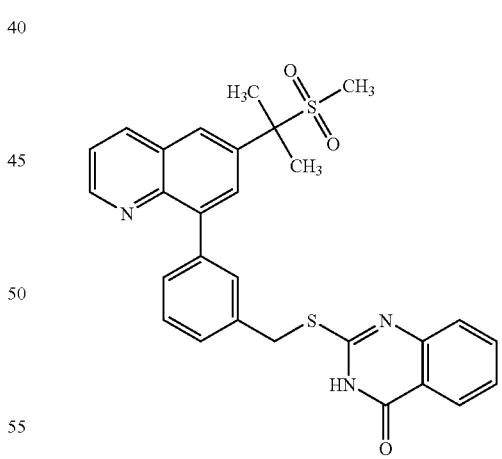

Prepared according to the procedure described in EXAMPLE 99, but using 2-mercapto-3H-quinazolin-4-one as the starting material. The title compound was obtained as a foam.

$^1$H NMR (500 MHz, acetone-$d_6$): δ 11.5 (s, 0.5H), 8.83 (dd, 1H), 8.42 (dd, 1H), 8.25 (d, 1H), 8.09 (app dd, 2H), 7.92 (s, 1H), 7.74 (app dt, 1H), 7.64 (app t, 2H), 7.58 (d, 1H), 7.53 (dd, 1H), 7.46–7.40 (m, 2H), 4.68 (s, 2H), 2.68 (s, 3H), 1.95 (s, 6H).

EXAMPLE 116

4-Amino-2-{3-[6-(1-methanesulfonyl-1-methyl-ethyl)-quinolin-8-yl]-benzylsulfanyl}-pyrimidine-5-carboxylic acid methyl ester

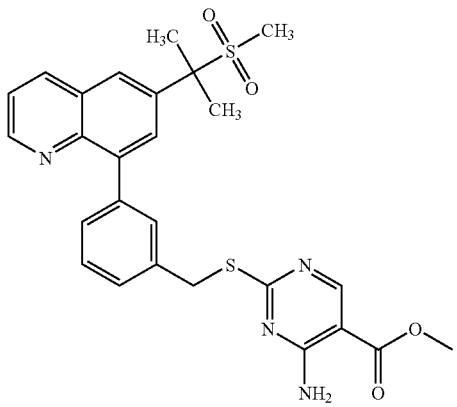

Prepared according to the procedure described in EXAMPLE 99, but using 4-amino-2-mercapto-pyrimidine-5-carboxylic acid methyl ester as the starting material. The title compound was obtained as a foam.

$^1$H NMR (400 MHz, acetone-$d_6$): δ 8.90 (dd, 1H), 8.66 (s, 1H), 8.44 (dd, 1H), 8.26 (d, 1H), 8.11 (d, 1H), 7.83 (brs, 2H), 7.63 (d, 1H), 7.56 (dd, 1H), 7.50 (d, 1H), 7.41 (t, 1H), 7.16 (brs, 1H), 4.48 (s, 2H), 4.33 (q, 2H), 2.70 (s, 3H), 1.98 (s, 6H), 1.35 (t, 3H).

EXAMPLE 117

N-(3,5-Dichloro-pyridin-4-yl)-3-[6-(1-methanesulfonyl-1-methyl-ethyl)-quinolin-8-yl]-benzamide

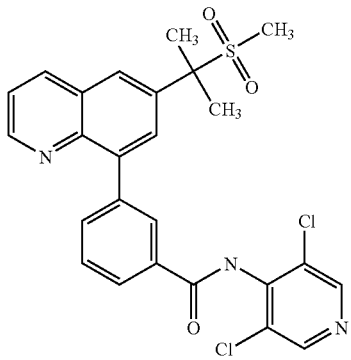

Step 1:
3-Bromo-N-(3,5-dichloro-pyridin-4-yl)-benzamide

To a solution of 4-amino 3,5-dichloro pyridine in THF (0.5M) at 0° C. was added NaH (1.5 eq). The mixture was stirred at 0° C. for 30 min then 3-bromo benzoyl chloride (2.0 eq.) was added dropwise. The resulting mixture was stirred 12 hours at room temperature, poured in water and extracted with EtOAc (2×). The combined organic extracts were washed with brine, dried over Na$_2$SO$_4$, filtered and concentrated. Flash chromatography (Hex:EtOAc; 1:1) afforded the desired compound a yellow solid.

Step 2: Example 117

The title compound was prepared in a two steps one-pot procedure. A mixture of the 3-bromo-N-(3,5-dichloro-pyridin-4-yl)-benzamide from Step 1, diboron pinacole ester (1.6 eq), KOAc (4 eq) and PdCl$_2$(dppf)$_2$ (cat) in DME (0.1M from benzamide) was stirred at 80° C. for 12 h. To the resulting mixture was added Quinoline 10 (0.8 eq) and aqueous Na$_2$CO$_3$ (2M; 3 eq). The mixture was stirred at 80° C. for 12 h, poured in H$_2$O and extracted with EtOAc (2×). The combined organic extracts were washed with water, brine, dried over MgSO$_4$, filtered and concentrated. Flash chromatography (Hex:EtOAc; 1:1) and subsequent suspension-filtration sequence of the residue in Hex:EtOAc:Et$_2$O afforded the title compound as a white solid.

$^1$H NMR (500 MHz, acetone-$d_6$): δ 9.76 (s, NH), 8.93 (m, 1H), 8.65 (s, 2H), 8.48 (dd, 1H), 8.42 (br s, 1H), 8.33 (m, 1H), 8.19 (d, 1H), 8.12 (s, 1H), 7.99 (dd, 1H), 7.68 (t, 1H), 7.60 (dd, 1H), 2.81 (s, 3H), 2.05 (s, 6H).

EXAMPLE 118

N-(3,5-Dichloro-1-oxy-pyridin-4-yl)-3-[6-(1-methanesulfonyl-1-methyl-ethyl)-quinolin-8-yl]-benzamide

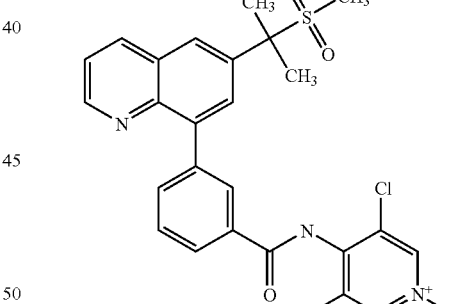

To a solution of N-(3,5-dichloro-pyridin-4-yl)-3-[6-(1-methanesulfonyl-1-methyl-ethyl)-quinolin-8-yl]-benzamide from EXAMPLE 117 in CHCl$_3$ (0.1M) was added CH$_3$C(O)OOH (10 eq). The mixture was stirred at 50° C. for 12 h cooled to room temperature. Flash chromatography of the crude mixture (CH$_2$Cl$_2$:EtOH; 9:1) afforded the title compound a yellow solid.

$^1$H NMR (500 MHz, acetone-$d_6$): δ 9.68 (s, NH), 8.93 (m, 1H), 8.48 (dd, 1H), 8.41 (m, 3H), 8.34 (brs, 1H), 8.19 (d, 1H), 8.11 (dd, 1H), 7.97 (dd, 1H), 7.68 (t, 1H), 7.60 (dd, 1H), 2.81 (s, 3H), 2.05 (s, 6H).

EXAMPLE 119

3-[6-(1-Methanesulfonyl-1-methyl-ethyl)-quinolin-8-yl]-N-(3-methylsulfanyl-phenyl)-benzamide

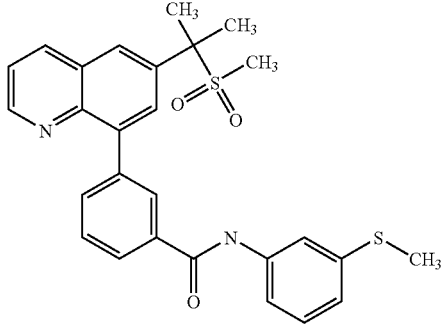

To solution of Quinoline 21 in DMF (0.2M) was added 3-methylsulfanyl-phenylamine (1.1 eq), HATU (1.2 eq) and DIPEA (2.5 eq). The mixture was stirred for 12 h, poured in water and extracted with EtOAc (2×). The combined organic extracts were washed with water, brine, dried over $MgSO_4$, filtered and concentrated. A suspension-filtration sequence of the residue in EtOAc afforded the title compound as a white solid.

$^1$H NMR (500 MHz, acetone-$d_6$): δ 9.61 (s, NH), 8.93 (m, 1H), 8.49 (dd, 1H), 8.33 (m, 2H), 8.19 (d, 1H), 8.02 (dd, 1H), 7.92 (dd, 1H), 7.87 (m, 1H), 7.62 (m, 3H), 7.29 (t, 1H), 7.01 (dd, 1H), 2.78 (s, 3H), 2.48 (s, 3H), 2.03 (s, 6H).

MS+ESI (M+1) 491.2

EXAMPLE 120

3-[6-(1-Methanesulfonyl-1-methyl-ethyl)-quinolin-8-yl]-N-(4-methylsulfanyl-phenyl)-benzamide

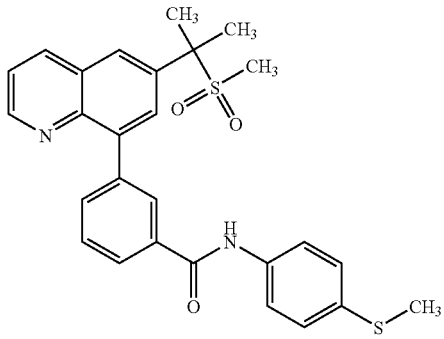

Prepared according to the procedure described in EXAMPLE 119 but using 4-methylsulfanyl-phenylamine as the starting material. A suspension-filtration sequence of the residue in EtOAc afforded the title compound as a white solid.

$^1$H NMR (500 MHz, acetone-$d_6$): δ 9.62 (s, NH), 8.93 (m, 1H), 8.48 (dd, 1H), 8.32 (m, 2H), 8.19 (d, 1H), 8.02 (dd, 1H), 7.90 (dd, 1H), 7.82 (d, 2H), 7.62 (m, 2H), 7.29 (d, 2H), 2.78 (s, 3H), 2.47 (s, 3H), 2.04 (s, 6H).

MS+ESI (M+1) 491.3

EXAMPLE 121

3-[6-(1-Methanesulfonyl-1-methyl-ethyl)-quinolin-8-yl]-N-(3-methanesulfonyl-phenyl)-benzamide

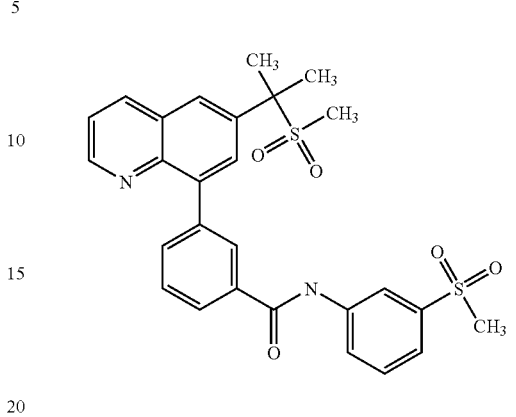

Prepared according to the procedure described in EXAMPLE 17 (Step 5) but using 3-[6-(1-methanesulfonyl-1-methyl-ethyl)-quinolin-8-yl]-N-(3-methylsulfanyl-phenyl)-benzamide from EXAMPLE 119 as the starting material. A suspension-filtration sequence of the residue p in EtOAc afforded the title compound as a white solid.

$^1$H NMR (500 MHz, acetone-$d_6$): δ 9.95 (s, NH), 8.93 (m, 1H), 8.52 (m, 1H), 8.49 (dd, 1H), 8.37 (br s, 1H), 8.32 (d, 1H), 8.19 (m, 2H), 8.09 (dd, 1H), 7.94 (dd, 1H), 7.85 (m, 3H), 7.60 (dd, 1H), 3.12 (s, 3H), 2.77 (s, 3H), 2.02 (s, 6H).

MS+ESI (M+1) 523.4

EXAMPLE 122

3-[6-(1-Methanesulfonyl-1-methyl-ethyl)-quinolin-8-yl]-N-(4-methanesulfonyl-phenyl)-benzamide

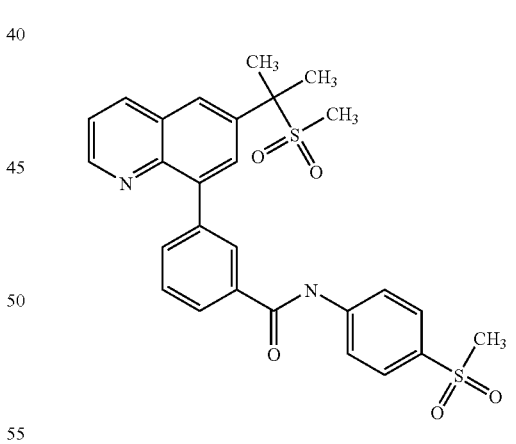

Prepared according to the procedure described in EXAMPLE 17 (Step 5) but using 3-[6-(1-methanesulfonyl-1-methyl-ethyl)-quinolin-8-yl]-N-(4-methylsulfanyl-phenyl)-benzamide from EXAMPLE 120 as the starting material. A suspension-filtration sequence of the residue p in EtOAc afforded the title compound as a white solid.

$^1$H NMR (500 MHz, acetone-$d_6$): δ 10.05 (s, NH), 8.93 (s, 1H), 8.49 (dd, 1), 8.36 (br s, 1H), 8.34 (d, 1H), 8.19 (d, 1H), 8.12 (d, 2H), 8.06 (dd, 1H), 7.92 (dd, 1H), 7.90 (d, 2H), 7.65 (t, 1H), 7.60 (dd, 1H), 3.10 (s, 3H), 2.76 (s, 3H), 2.05 (s, 6H).

EXAMPLE 123

3-[6-(1-Methanesulfonyl-1-methyl-ethyl)-quinolin-8-yl]-N-pyridin-3-yl-benzamide

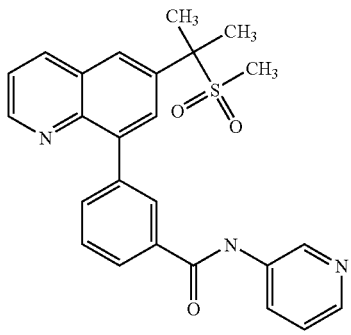

Prepared according to the procedure described in EXAMPLE 120 but using 3-aminopyridine as the starting material. Flash chromatography (CH$_2$Cl$_2$:MeOH; 95:5) afforded the title compound as a white solid.

$^1$H NMR (500 MHz, acetone-d$_6$): δ 9.87 (s, NH), 8.98 (m, 2H), 8.50 (d, 1H), 8.35 (m, 4H), 8.21 (s, 1H), 8.08 (d, 1H), 7.94 (d, 1H), 7.66 (t, 1H), 7.62 (dd, 1H), 7.37 (m, 1H), 2.79 (s, 3H), 2.07 (s, 6H).

EXAMPLE 124

3-[6-(1-Methanesulfonyl-1-methyl-ethyl)-quinolin-8-yl]-N-(1-oxy-pyridin-3-yl)-benzamide

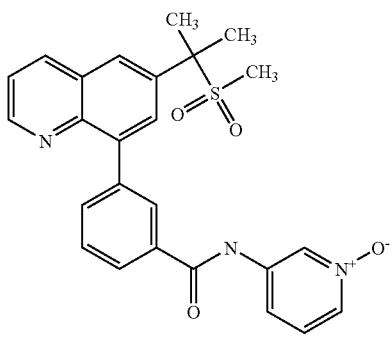

To solution of 3-[6-(1-methanesulfonyl-1-methyl-ethyl)-quinolin-8-yl]-N-pyridin-3-yl-benzamide EXAMPLE 123 in CH$_2$Cl$_2$ (0.05M) was added 3-chloroperoxybenzoic acid (1.2 eq). The mixture was stirred for 12 h and then concentrated. Flash chromatography (CH$_2$CL$_2$:MeOH; 2:1) afforded the title compound as a white solid.

$^1$H NMR (500 MHz, acetone-d$_6$): δ 10.04 (s, NH), 9.00 (m, 1H), 8.97 (dd, 1H), 8.51 (dd, 1H), 8.38 (m, 2H), 8.23 (d, 1H), 8.07 (dd, 1H), 7.96 (m, 2H), 7.75 (m, 1H), 7.67 (m, 1H), 7.62 (dd, 1H), 7.38 (m, 1H), 2.79 (s, 3H), 2.08 (s, 6H). +ESI, Q1 (M+1) 462.2

EXAMPLE 125

3-[6-(1-Methanesulfonyl-1-methyl-ethyl)-quinolin-8-yl]-N-(5-methyl-thiazol-2-yl)-benzamide

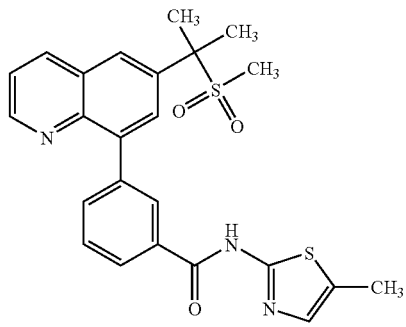

Prepared according to the procedure described in EXAMPLE 120 but using 5-methyl thiazol-2-ylamine as the starting material. Flash chromatography (CH$_2$Cl$_2$:MeOH; 95:5) and subsequent suspension-filtration sequence in Tol:CH$_2$Cl$_2$:MeOH afforded the title compound as a light yellow solid.

$^1$H NMR (500 MHz, acetone-d$_6$): δ 12.52 (s, NH), 8.95 (s, 1H), 8.54 (dd, 1H), 8.30 (m, 2H), 8.12 (dd, 1H), 8.07 (s, 1H), 7.91 (dd, 1H), 7.66 (m, 2H), 7.22 (s, 1H), 2.81 (s, 3H), 2.40 (s, 3H), 1.99 (s, 6H). +ESI, Q1 (M+1) 466.1

EXAMPLE 126

3-[6-(1-Methanesulfonyl-1-methyl-ethyl)-quinolin-8-yl]-N-quinolin-3-yl-benzamide

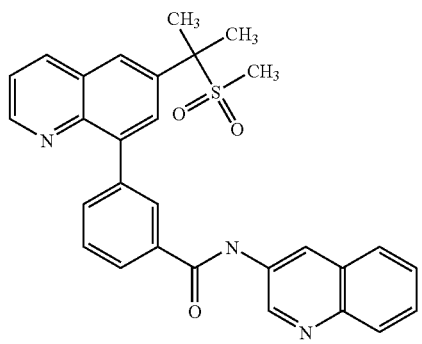

Prepared according to the procedure described in EXAMPLE 120 but using 3-aminoquinoline as the starting material. Flash chromatography (CH$_2$Cl$_2$:MeOH; 95:5) afforded the title compound as a white solid.

$^1$H NMR (500 MHz, acetone-d$_6$): δ 10.08 (s, NH), 9.17 (d, 1H), 8.99 (m, 2H), 8.50 (dd, 1H), 8.45 (m, 1H), 8.35 (m, 1H), 8.23 (m, 1H), 8.13 (dd, 1H), 8.02 (d, 1H), 7.98 (m, 2H), 7.68 (m, 2H), 7.52 (m, 2H), 2.79 (s, 3H), 2.06 (s, 6H). +ESI, Q1 (M+1) 496.3

EXAMPLE 127

N-(6-Methanesulfonyl-benzothiazol-2-yl)-3-[6-(1-methanesulfonyl-1-methyl-ethyl)-quinolin-8-yl]-benzamide

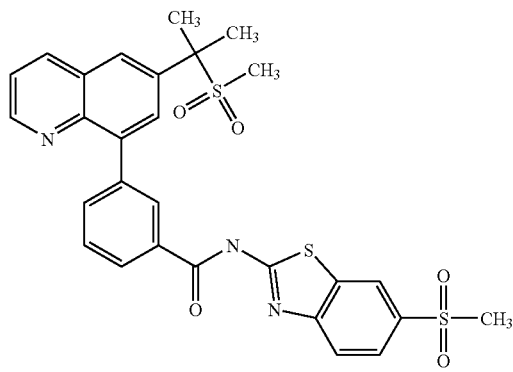

Prepared according to the procedure described in EXAMPLE 120 but using 6-methanesulfonyl-benzothiazol-2-ylamine as the starting material. Flash chromatography (CH$_2$Cl$_2$:MeOH; 95:5) afforded the title compound as a white solid.

$^1$H NMR (500 MHz, DMSO-d$_6$): δ 11.96 (s, NH), 8.97 (m, 1H), 8.63 (m, 2H), 8.51 (dd, 1H), 8.37 (m, 1H), 8.30 (dd, 1H), 8.26 (d, 1H), 8.08 (m, 1H), 7.97 (m, 1H), 7.93 (s, 1H), 7.74 (t, 1H), 7.62 (dd, 1H), 2.79 (s, 3H), 2.77 (m, 3H), 2.04 (s, 6H). +ESI, Q1 (M+1) 580.0

EXAMPLE 128

N-(5-Cyclopropyl-[1,3,4]thiadiazol-2-yl)-3-[6-(1-methanesulfonyl-1-methyl-ethyl)-quinolin-8-yl]-benzamide

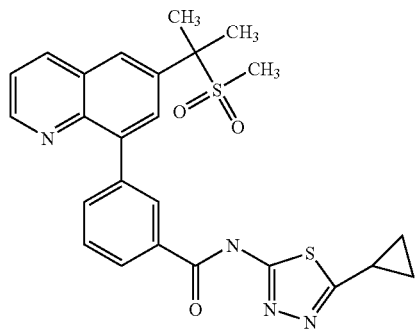

Prepared according to the procedure described in EXAMPLE 120 but using 5-cyclopropyl-[1,3,4]thiadiazol-2-ylamine as the starting material. Flash chromatography (CH$_2$Cl$_2$:MeOH; 95:5) afforded the title compound as a white solid.

$^1$H NMR (500 MHz, DMSO-d$_6$): δ 12.99 (s, NH), 8.98 (m, 1H), 8.56 (dd, 1H), 8.34 (m, 2H), 8.16 (d, 1H), 8.08 (s, 1H), 7.96 (s, 1H), 7.68 (s, 1H), 7.65 (dd, 1H), 2.81 (s, 3H), 2.45 (m, 1H), 1.98 (s, 6H), 1.18 (m, 2H), 1.03 (m, 2H). +ESI, Q1 (M+1) 493.2

EXAMPLE 129

3-[6-(1-Methanesulfonyl-1-methyl-ethyl)-quinolin-8-yl]-N-(5-trifluoromethyl-[1,3,4]thiadiazol-2-yl)-benzamide

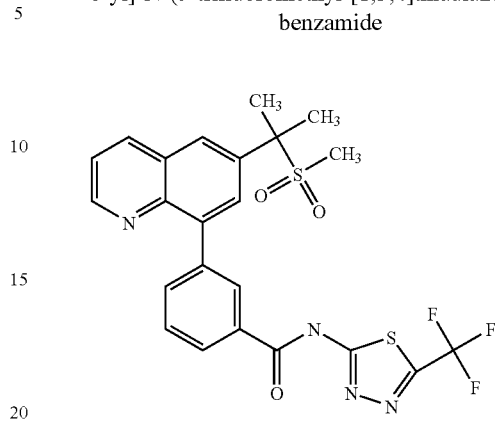

Prepared according to the procedure described in EXAMPLE 120 but using 5-trifluoromethylthiadiazol-2-ylamine as the starting material. Flash chromatography (CH$_2$Cl$_2$:MeOH; 95:5) afforded the title compound as a white solid.

$^1$H NMR (500 MHz, acetone-d$_6$): δ 12.22 (s, NH), 8.97 (dd, 1H), 8.60 (m, 1H), 8.53 (dd, 1H), 8.38 (d, 1H), 8.31 (dd, 1H), 8.25 (d, 1H), 8.10 (dd, 1H), 7.78 (t, 1H), 7.63 (dd, 1H), 2.79 (s, 3H), 2.05 (s, 6H). +ESI, Q1 (M+1) 521.1

EXAMPLE 130

N-Benzothiazol-2-yl-3-[6-(1-methanesulfonyl-1-methyl-ethyl)-quinolin-8-yl]-benzamide

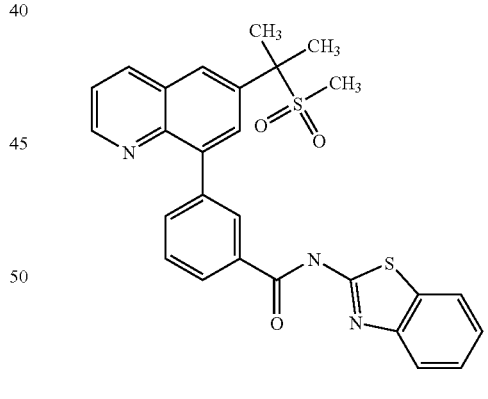

Prepared according to the procedure described in EXAMPLE 120 but using benzothiazol-2-ylamine as the starting material. Flash chromatography (CH$_2$Cl$_2$:MeOH; 95:5) afforded the title compound as a white solid.

$^1$H NMR (500 MHz, acetone-d$_6$): δ 12.98 (s, NH), 8.98 (dd, 1H), 8.57 (dd, 1H), 8.40 (s, 1H), 8.33 (s, 1H), 8.20 (dd, 1H), 8.11 (m, 1H), 8.04 (dd, 1H), 7.98 (dd, 1H), 7.81 (m, 1H), 7.71 (t, 1H), 7.66 (dd, 1H), 7.48 (t, 1H), 7.37 (t, 1H), 2.81 (s, 3H), 1.99 (s, 6H). +ESI, Q1 (M+1) 502.0

EXAMPLE 131

3-[6-(1-Methanesulfonyl-1-methyl-ethyl)-quinolin-8-yl]-N-(4-phenyl-thiazol-2-yl)-benzamide

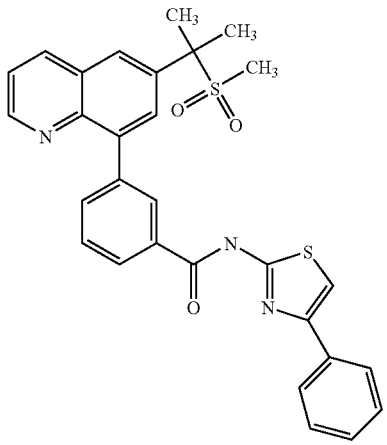

Prepared according to the procedure described in EXAMPLE 120 but using 4-phenylthiazol-2-ylamine as the starting material. Flash chromatography (CH$_2$Cl$_2$:MeOH; 95:5) afforded the title compound as a white solid.

$^1$H NMR (500 MHz, acetone-d$_6$): δ 12.89 (s, NH), 8.97 (dd, 1H), 8.57 (dd, 1H), 8.39 (s, 1H), 8.34 (s, 1H), 8.20 (dd, 1H), 8.10 (s, 1H), 7.86 (m, 3H), 7.72 (m, 1H), 7.69 (t, 1H), 7.65 (dd, 1H), 7.46 (m, 2H), 7.35 (s, 1H), 2.82 (s, 3H), 1.98 (s, 6H). +ESI, Q1 (M+1) 528.3

EXAMPLE 132

3-[6-(1-Methanesulfonyl-1-methyl-ethyl)-quinolin-8-yl]-N-pyridin-2-yl-benzamide

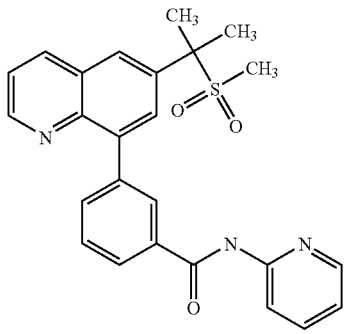

Prepared according to the procedure described in EXAMPLE 120 but using 2-aminopyridine as the starting material. Flash chromatography (EtOAc) afforded the title compound as a white solid.

$^1$H NMR (500 MHz, acetone-d$_6$): δ 9.78 (s, 1H), 8.94 (m, 1H), 8.51 (dd, 1H), 8.47 (s, 1H), 8.42 (dd, 1H), 8.35 (m, 2H), 8.25 (m, 1H), 8.18 (dd, 1H), 7.99 (dd, 1H), 7.85 (td, 1H), 7.68 (t, 1H), 7.62 (dd, 1H), 7.16 (t, 1H), 2.78 (s, 3H), 2.05 (s, 6H). +ESI, Q1 (M+1) 446.2

EXAMPLE 133

3-[6-(1-Methanesulfonyl-1-methyl-ethyl)-quinolin-8-yl]-N-pyridin-4-yl-benzamide

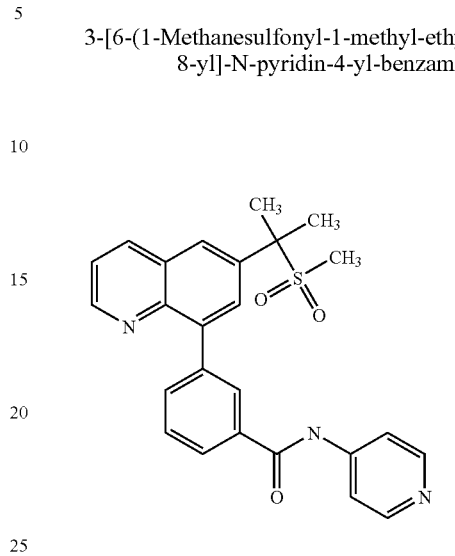

Prepared according to the procedure described in EXAMPLE 120 but using 4-aminopyridine as the starting material. Flash chromatography (EtOAc) afforded the title compound as a white solid.

$^1$H NMR (500 MHz, acetone-d$_6$): δ 10.45 (s, NH), 8.96 (dd, 1H), 8.72 (d, 2H), 8.53 (dd, 1H), 8.39 (s, 1H), 8.37 (d, 1H), 8.23 (d, 1H), 8.17 (d, 2H), 8.10 (dd, 1H), 8.02 (dd, 1H), 7.72 (t, 1H), 7.64 (dd, 1H), 2.78 (s, 3H), 2.04 (s, 6H). +ESI, Q1 (M+1) 446.2

EXAMPLE 134

N-(5-Bromo-thiazol-2-yl)-3-[6-(1-methanesulfonyl-1-methyl-ethyl)-quinolin-8-yl]-benzamide

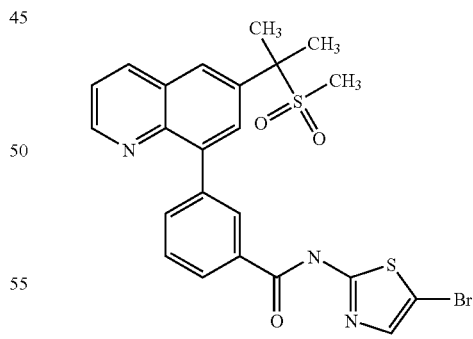

Prepared according to the procedure described in EXAMPLE 120 but using 5-bromothiazol-2-ylamine as the starting material. Flash chromatography (EtOAc:Hex; 4:1) afforded the title compound as a white solid.

$^1$H NMR (500 MHz, acetone-d$_6$): δ 11.72 (s, NH), 8.97 (dd, 1H), 8.52 (m, 2H), 8.36 (d, 1H), 8.24 (d, 1H), 8.21 (dd, 1H), 8.05 (dd, 1H), 7.71 (t, 1H), 7.63 (dd, 1H), 7.51 (s, 1H), 2.79 (s, 3H), 2.04 (s, 6H). +ESI, Q1 (M+1) 530.1

EXAMPLE 135

3-[6-(1-Methanesulfonyl-1-methyl-ethyl)-quinolin-8-yl]-N-(4-pyridin-4-ylmethyl-phenyl)-benzamide

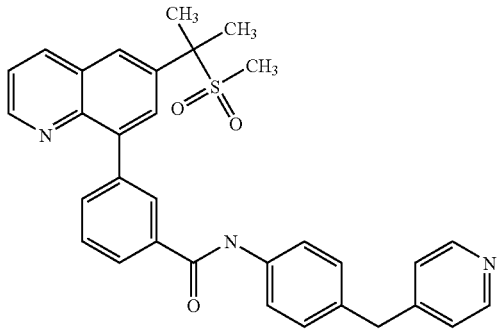

Prepared according to the procedure described in EXAMPLE 120 but using 4-pyridin-4-ylmethyl-phenylamine as the starting material. Flash chromatography (CH$_2$Cl$_2$:MeOH; 95:5) afforded the title compound as a white solid.

$^1$H NMR (500 MHz, acetone-d$_6$): δ 9.73 (s, NH), 8.94 (dd, 1H), 8.48 (m, 3H), 8.33 (m, 2H), 8.20 (d, 1H), 8.03 (dd, 1H), 7.98 (s, 1H), 7.92 (dd, 1H), 7.83 (d, 1H), 7.62 (t, 1H), 7.60 (dd, 1H), 7.25 (m, 4H), 3.99 (s, 2H), 2.79 (s, 3H), 2.01 (s, 6H). +ESI, Q1 (M+1) 536.2

EXAMPLE 136

3-[6-(1-Methanesulfonyl-1-methyl-ethyl)-quinolin-8-yl]-N-[4-(1-oxy-pyridin-4-ylmethyl)-phenyl]-benzamide

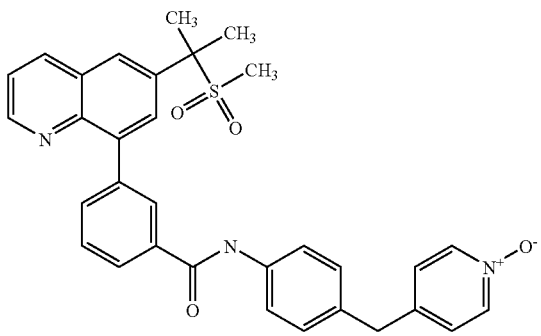

Prepared according to the procedure described in EXAMPLE 124 but using 3-[6-(1-Methanesulfonyl-1-methyl-ethyl)-quinolin-8-yl]-N-(4-pyridin-4-ylmethyl-phenyl)-benzamide from EXAMPLE 135 as the starting material. Flash chromatography (CH$_2$Cl$_2$:MeOH; 9:1) afforded the title compound as a white solid.

$^1$H NMR (500 MHz, acetone-d$_6$): δ 9.79 (s, NH), 8.95 (dd, 1H), 8.50 (dd, 1H), 8.34 (m, 2H), 8.21 (d, 1H), 8.05 (m, 3H), 8.01 (dd, 1H), 7.92 (dd, 1H), 7.85 (d, 1H), 7.63 (m, 2H), 7.27 (d, 2H), 7.23 (d, 2H), 3.99 (s, 2H), 2.78 (s, 3H), 2.03 (s, 6H). +ESI Q1 (M+1) 552.3

EXAMPLE 137

3-[6-(1-Methanesulfonyl-1-methyl-ethyl)-quinolin-8-yl]-N-(1-oxy-pyridin-4-yl)-benzamide

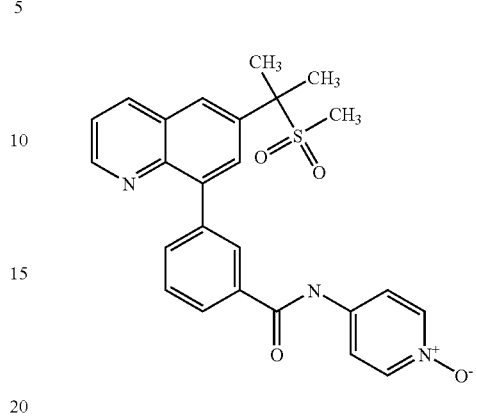

Prepared according to the procedure described in EXAMPLE 124 but using 3-[6-(1-Methanesulfonyl-1-methyl-ethyl)-quinolin-8-yl]-N-pyridin-4-yl-benzamide from EXAMPLE 133 as the starting material. Flash chromatography (CH$_2$Cl$_2$:MeOH; 9:1) afforded the title compound as a white solid.

$^1$H NMR (500 MHz, DMSO-d$_6$): δ 10.82 (s, NH), 8.98 (dd, 1H), 8.56 (d, 1H), 8.33 (s, 1H), 8.22 (s, 1H), 8.17 (d, 2H), 8.08 (s, 1H), 8.02 (dd, 1H), 7.92 (dd, 1H), 7.85 (d, 2H), 7.70 (t, 1H), 7.66 (dd, 1H), 2.82 (s, 3H), 1.99 (s, 6H). +ESI Q1 (M+1) 462.3

EXAMPLE 138

N-(2-Bromo-4-pyridin-4-ylmethyl-phenyl)-3-[6-(1-methanesulfonyl-1-methyl-ethyl)-quinolin-8-yl]-benzamide

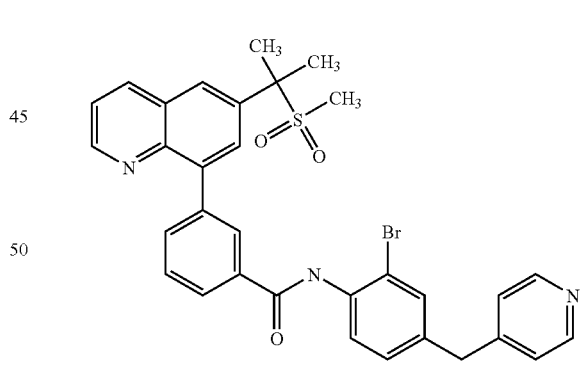

Prepared according to the procedure described in EXAMPLE 120 but using 2-bromo-4-pyridin-4-ylmethyl-phenylamine as the starting material. Flash chromatography (CH$_2$Cl$_2$:MeOH; 95:5) afforded the title compound as a white solid.

$^1$H NMR (500 MHz, acetone-d$_6$): δ 9.09 (s, NH), 8.98 (dd, 1H), 8.49 (m, 3H), 8.44 (br s, 1H), 8.35 (d, 1H), 8.25 (d, 1H), 8.18 (d, 1H), 8.08 (dd, 1H), 8.01 (dd, 1H), 7.69 (t, 1H), 7.61 (m, 2H), 7.36 (dd, 1H), 7.27 (d, 2H), 4.05 (s, 2H), 2.78 (s, 3H), 2.02 (s, 6H). +ESI Q1 (M+1) 614.2

EXAMPLE 139

N-[2-Bromo-4-(1-oxy-pyridin-4-ylmethyl)-phenyl]-3-[6-(1-methanesulfonyl-1-methyl-ethyl)-quinolin-8-yl]-benzamide

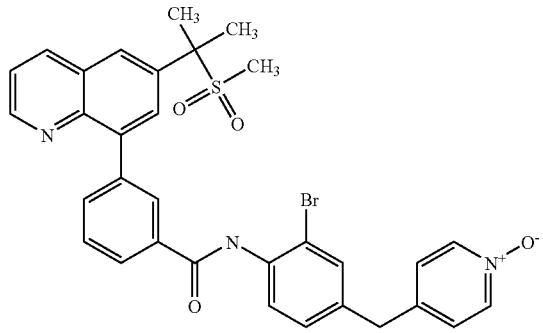

Prepared according to the procedure described in EXAMPLE 124 but using N-(2-Bromo-4-pyridin-4-ylmethyl-phenyl)-3-[6-(1-methanesulfonyl-1-methyl-ethyl)-quinolin-8-yl]-benzamide from EXAMPLE 138 as the starting material. Flash chromatography (CH$_2$Cl$_2$:MeOH; 9:1) afforded the title compound as a white solid.

$^1$H NMR (500 MHz, acetone-d$_6$): δ 9.15 (s, NH), 8.98 (dd, 1H), 8.50 (dd, 1H), 8.46 (s, 1H), 8.35 (d, 1H), 8.26 (d, 1H), 8.17 (d, 1H), 8.08 (m, 3H), 8.00 (dd, 1H), 7.69 (t, 1H), 7.62 (m, 2H), 7.37 (dd, 1H), 7.29 (d, 2H), 4.03 (s, 2H), 2.79 (s, 3H), 2.03 (s, 6H). +ESI Q1 (M+1) 631.8

EXAMPLE 140

N-(6-Chloro-pyridin-3-yl)-3-[6-(1-methanesulfonyl-1-methyl-ethyl)-quinolin-8-yl]-benzamide

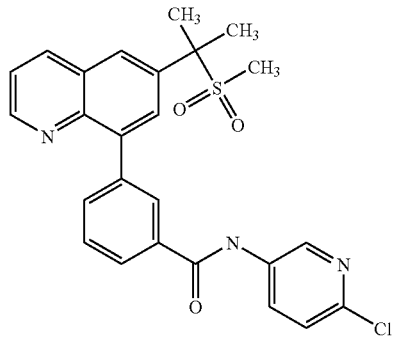

Prepared according to the procedure described in EXAMPLE 120 but using 3-amino-6-chloro-pyridine as the starting material. Flash chromatography (CH$_2$Cl$_2$:MeOH; 95:5) afforded the title compound as a white solid.

$^1$H NMR (500 MHz, DMSO-d$_6$): δ 10.68 (s, NH), 8.98 (dd, 1H), 8.82 (d, 1H), 8.56 (dd, 1H), 8.33 (d, 1H), 8.28 (dd, 1H), 8.22 (br s, 1H), 8.07 (d, 1H), 8.04 (dd, 1H), 7.90 (dd, 1H), 7.70 (t, 1H), 7.64 (dd, 1H), 7.53 (d, 1H), 2.82 (s, 3H), 1.97 (s, 6H). +ESI Q1 (M+1) 480.0

EXAMPLE 141

3-[6-(1-Methanesulfonyl-1-methyl-ethyl)-quinolin-8-yl]-N-[6-(4-methylsulfanyl-phenyl)-pyridin-3-yl]-benzamide

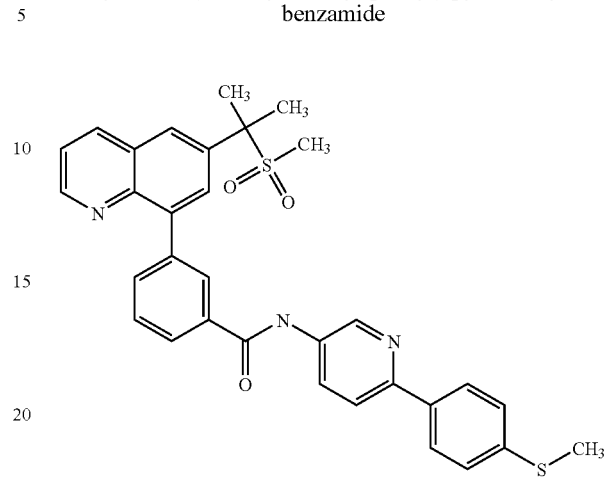

A mixture of N-(6-Chloro-pyridin-3-yl)-3-[6-(1-methanesulfonyl-1-methyl-ethyl)-quinolin-8-yl]-benzamide, 4-methylsulfanyl-phenyl boronic acid (2 eq), PdCl$_2$(dppf)$_2$ (0.05 eq) and aqueous Na2CO3 (4 eq) in DME (0.04M from benzamide) was stirred at 100° C. for 12 h. The resulting mixture was poured in water and extracted with EtOAc (2×). The combined organic extracts were washed with water, brine, dried over MgSO$_4$, filtered and concentrated. Flash chromatography (EtOAc) afforded the title compound as a white solid.

$^1$H NMR (500 MHz, DMSO-d$_6$): δ 9.97 (s, NH), 9.06 (d, 1H), 8.95 (m, 1H), 8.50 (dd, 1H), 8.42 (dd, 1H), 8.39 (s, 1H), 8.34 (d, 1H), 8.21 (d, 1H), 8.08 (m, 3H), 7.96 (m, 2H), 7.66 (t, 1H), 7.61 (dd, 1H), 7.37 (d, 2H), 2.94 (s, 3H), 2.79 (s, 3H), 2.05 (s, 6H). +ESI Q1 (M+1) 568.2

Other variations or modifications, which will be obvious to those skilled in the art, are within the scope and teachings of this invention. This invention is not to be limited except as set forth in the following claims.

What is claimed is:

1. A compound represented by Formula (I):

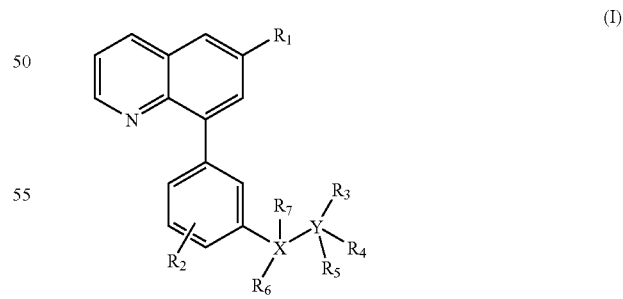

(I)

or a pharmaceutically acceptable salt thereof, wherein
R$_1$ is hydrogen or a halogen, -carbonyl-C$_0$–C$_6$alkyl, —C$_1$–C$_6$alkyl group, -cycloC$_3$–C$_6$alkyl group, —C$_1$–C$_6$alkenyl group, —C$_1$–C$_6$alkoxy group, aryl group, heteroaryl group, —CN, -heterocycloC$_3$–C$_6$alkyl group, —N(C$_0$–C$_6$alkyl)(C$_0$–C$_6$alkyl) group, —C$_1$–C$_6$alkyl-N(C$_0$–C$_6$alkyl)

($C_0$–$C_6$alkyl) group, —$C_1$–$C_6$alkyl(oxy)$C_1$–$C_6$alkyl group, —C(O)NH(aryl) group, —C(O)NH(heteroaryl) group, —$SO_n$NH(aryl) group, —$SO_n$NH(heteroaryl) group, —$SO_n$NH($C_1$–$C_6$alkyl) group, —C(O)N ($C_0$–$C_6$alkyl)($C_0$–$C_6$alkyl) group, —NH—$SO_n$— ($C_1$–$C_6$alkyl) group, —$SO_n$—($C_1$–$C_6$alkyl) group, -carbamoyl group, —($C_1$–$C_6$alkyl)-O—C(CN) —N($C_0$–$C_6$alkyl)($C_0$–$C_6$alkyl) group, or —($C_1$–$C_6$alkyl)-$SO_n$—($C_1$–$C_6$alkyl) group, wherein any of the groups is optionally substituted with 1–5 substituents; wherein each substituent is independently a halogen, —OH, —CN, —C(O) (heterocyclo$C_3$–$C_6$alkyl), —C(O)—O—($C_0$–$C_6$alkyl), —C(O)—O-aryl, $C_1$–$C_6$alkoxy, —$C_3$–$C_6$cycloalkyloxy, acyl, acyloxy, -cyclo$C_3$–$C_6$alkyl, heterocyclo$C_3$–$C_6$alkyl, aryl, heteroaryl, pyridyl N-oxide, pyridyl N-chloride, -carbonyl-$C_0$–$C_6$alkyl, carbamoyl, or —$SO_n$—($C_1$–$C_6$alkyl);

$R_2$ is hydrogen, halogen, hydroxyl, —$C_1$–$C_6$alkyl, or —$C_1$–$C_6$alkoxy, wherein the alkyl and alkoxy are optionally substituted with 1–3 independently halogen or OH;

$R_3$ is absent, —H, —COOH, —C(O)$NH_2$, or a —$C_1$–$C_6$alkyl group, —$C_1$–$C_4$alkyl$C_3$–$C_6$cycloalkyl group, —C(O)$C_3$–$C_6$cycloalkyl group, —C(O) $C_1$–$C_6$alkyl group, —C(O)phenyl group, —C(O) NHphenyl group, —C(O)NH$C_1$–$C_6$alkyl group, —C(O)—O—$C_1$–$C_6$alkyl group, —S(O)$_2$$C_1$–$C_6$alkyl group, —S(O)$_2$phenyl group, —S(O)$_2$$C_1$–$C_4$alkenyl group, —S(O)$_2$(5-membered heteroaryl containing 1–3 heteroatoms independently O, N, or S) group, —C(O) (5-membered heteroaryl containing 1–3 heteroatoms independently O, N, or S) group, or —C(O)(6-membered heteroaryl containing 1–4 heteroatoms independently O, N, or S) group, wherein any of the groups is optionally substituted with 1–5 substituents; wherein each substituent is independently —OH, halogen, —N(O)$_2$, COOH, phenyl substituent group, or —$C_1$–$C_4$alkyl substituent group, wherein any of the substituent groups is optionally substituted with 1–5 independently —OH or halogen;

$R_4$ is a phenyl group, pyrazolopyrimidinyl group, benzothiazolyol group, quinazolinonyl group, 5-membered heteroaryl containing 1–3 heteroatoms independently O, N, or S group, or 6-membered heteroaryl containing 1–4 heteroatoms independently O, N, or S group, wherein any of the groups is optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl ($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl (6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen;

$R_5$ is —H or absent;

$R_6$ is absent, —H or —$C_1$–$C_6$alkyl;

$R_7$ is —H or absent;

X is O, S, N, C, or C=O, wherein when X is O, S, or C=O then $R_6$ and $R_7$ are absent and when X is N then $R_7$ is absent;

Y is C, S, N, S(O)$_2$, O, or C=O wherein when Y is S, S(O)$_2$, O, or C=O then $R_3$ and $R_5$ are absent, and when Y is N then $R_5$ is absent;

at least one of X and Y must be O, N, S, or S(O)$_2$;

when X and Y are both N, then $R_3$, $R_5$, $R_6$, and $R_7$ are absent; and n is 0, 1, or 2.

2. The compound according to claim 1, or a pharmaceutically acceptable salt thereof, wherein:

$R_4$ is a phenyl group optionally substituted with 1–5 substituents; wherein each substituent is independently —OH, —CN, =O, halogen, —$N_3$, —$NO_2$, —COOH, —$C_1$–$C_6$alkyl substituent group, —$C_2$–$C_6$alkenyl substituent group, —$C_3$–$C_6$cycloalkyl substituent group, morpholinyl substituent group, benzothiazolyl substituent group, —$C_0$–$C_6$alkyl(aryl) substituent group, —N($C_0$–$C_6$alkyl)($C_0$–$C_6$alkyl) substituent group, —C(O)—$C_0$–$C_6$alkyl(aryl) substituent group, —C(O)-pyrazolyl-phenyl substituent group, —$C_2$–$C_6$alkenyl-C(O)—$C_0$–$C_4$alkyl(aryl) substituent group, —O—$C_1$–$C_6$alkyl(aryl) substituent group, —$C_1$–$C_6$alkyl($C_3$–$C_6$cycloalkyl)(—$C_0$–$C_6$alkylphenyl) substituent group, —$C_1$–$C_6$alkyl ($C_3$–$C_6$cycloalkyl)($C_3$–$C_6$cycloalkyl) substituent group, —$C_1$–$C_4$alkyl-S(O)$_2$phenyl substituent group, —O—$C_1$–$C_6$alkyl substituent group, —S—$C_1$–$C_6$alkyl substituent group, —$C_0$–$C_6$alkyl(5-membered heteroaryl containing 1–3 heteroatoms independently O, N, or S) substituent group, —$C_0$–$C_6$alkyl (6-membered heteroaryl containing 1–3 heteroatoms independently O, N, or S) substituent group, —$C_0$–$C_6$alkyl(6-membered heterocycloalkyl containing 1–3 heteroatoms independently O, N, or S) substituent group, —C(O)$C_1$–$C_6$alkyl substituent group, —C(O)—O—$C_1$–$C_6$alkyl substituent group, —S$C_1$–$C_6$alkyl substituent group, —S(O)$_2$$C_1$–$C_6$alkyl substituent group, wherein any of the substituent groups is optionally substituted with 1–5 independently —OH or halogen.

3. The compound according to claim 2, or a pharmaceutically acceptable salt thereof, wherein:

X is C;

Y is S; and $R_3$ and $R_5$ are absent.

4. The compound according to claim 2, or a pharmaceutically acceptable salt thereof, wherein:

X is C;

Y is S(O)$_2$; and $R_3$ and $R_5$ are absent.

5. The compound according to claim 2, or a pharmaceutically acceptable salt thereof, wherein:

X is C;

Y is N; and

R$_5$ is absent.

6. The compound according to claim 2, or a pharmaceutically acceptable salt thereof, wherein:

X is C;

Y is O; and

R$_3$ and R$_5$ are absent.

7. The compound according to claim 2, or a pharmaceutically acceptable salt thereof, wherein:

X is N;

R$_7$ is absent;

Y is C=O; and

R$_3$ and R$_5$ are absent.

8. The compound according to claim 2, or a pharmaceutically acceptable salt thereof, wherein:

X is N;

R$_7$ is absent;

Y is S(O)$_2$; and

R$_3$ and R$_5$ are absent.

9. The compound according to claim 2, or a pharmaceutically acceptable salt thereof, wherein X is N;

Y is N; and

R$_3$, R$_5$, R$_6$, and R$_7$ are absent.

10. The compound according to claim 2, or a pharmaceutically acceptable salt thereof, wherein:

X is O;

R$_6$ and R$_7$ are absent; and

Y is C.

11. The compound according to claim 2, or a pharmaceutically acceptable salt thereof, wherein X is O;

R$_6$ and R$_7$ are absent;

Y is S(O)$_2$; and

R$_3$ and R$_5$ are absent.

12. The compound according to claim 2, or a pharmaceutically acceptable salt thereof, wherein X is S;

R$_6$ and R$_7$ are absent; and

Y is C.

13. The compound according to claim 1, or a pharmaceutically acceptable salt thereof, wherein:

R$_4$ is a 5-membered heteroaryl containing 1–3 heteroatoms independently O, N, or S group, optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1-3 heteroatoms independently O, N, or S) substituent group, —C$_0$–C$_6$alkyl (6-membered heteroaryl containing 1-3 heteroatoms independently O, N, or S) substituent group, —C$_0$–C$_6$alkyl(6-membered heterocycloalkyl containing 1-3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen.

14. The compound according to claim 13, or a pharmaceutically acceptable salt thereof, wherein, X is N;

R$_7$ is absent;

Y is S(O)$_2$; and

R$_3$ and R$_5$ are absent.

15. The compound according to claim 13, or a pharmaceutically acceptable salt thereof, wherein, X is C=O;

R$_6$ and R$_7$ are absent;

Y is N; and

R$_5$ is absent.

16. The compound according to claim 1, or a pharmaceutically acceptable salt thereof, wherein R$_4$ is a 6-membered heteroaryl containing 1-4 heteroatoms independently O, N, or S group, optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl (C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1-3 heteroatoms independently O, N, or S) substituent group, —C$_0$–C$_6$alkyl (6-membered heteroaryl containing 1-3 heteroatoms independently O, N, or S) substituent group, —C$_0$–C$_6$alkyl(6-membered heterocycloalkyl containing 1-3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen.

17. The compound according to claim 16, or a pharmaceutically acceptable salt thereof, wherein X is C;

Y is S; and

R$_3$ and R$_5$ are absent.

18. The compound according to claim 16, or a pharmaceutically acceptable salt thereof, wherein X is C;

Y is N; and

R$_5$ is absent.

19. The compound according to claim 1, or a pharmaceutically acceptable salt thereof, wherein R$_4$ is pyrazolopyrimidinyl optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl (6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen.

20. The compound according to claim 19, or a pharmaceutically acceptable salt thereof, wherein X is C;

Y is S; and

R$_3$ and R$_5$ are absent.

21. The compound according to claim 1, or a pharmaceutically acceptable salt thereof, wherein R$_4$ is benzothiazolyl optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl (6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen.

22. The compound according to claim 21, or a pharmaceutically acceptable salt thereof, wherein X is C;

Y is S; and

R$_3$ and R$_5$ are absent.

23. The compound according to claim 1, or a pharmaceutically acceptable salt thereof, wherein R$_4$ is quinazolinonyl optionally substituted with 1–5 substituents; wherein each substituent is independently —OH, —CN, =O, halogen, —N$_3$, —NO$_2$, —COOH, —C$_1$–C$_6$alkyl substituent group, —C$_2$–C$_6$alkenyl substituent group, —C$_3$–C$_6$cycloalkyl substituent group, morpholinyl substituent group, benzothiazolyl substituent group, —C$_0$–C$_6$alkyl(aryl) substituent group, —N(C$_0$–C$_6$alkyl)(C$_0$–C$_6$alkyl) substituent group, —C(O)—C$_0$–C$_6$alkyl(aryl) substituent group, —C(O)-pyrazolyl-phenyl substituent group, —C$_2$–C$_6$alkenyl-C(O)—C$_0$–C$_4$alkyl(aryl) substituent group, —O—C$_1$–C$_6$alkyl(aryl) substituent group, —C$_1$–C$_6$alkyl(C$_3$–C$_6$cycloalkyl)(—C$_0$–C$_6$alkylphenyl) substituent group, —C$_1$–C$_6$alkyl(C$_3$–C$_6$cycloalkyl)(C$_3$–C$_6$cycloalkyl) substituent group, —C$_1$–C$_4$alkyl-S(O)$_2$phenyl substituent group, —O—C$_1$–C$_6$alkyl substituent group, —S—C$_1$–C$_6$alkyl substituent group, —C$_0$–C$_6$alkyl(5-membered heteroaryl containing 1–3 heteroatoms independently O, N, or S) substituent group, —C$_0$–C$_6$alkyl (6-membered heteroaryl containing 1–3 heteroatoms independently O, N, or S) substituent group, —C$_0$–C$_6$alkyl(6-membered heterocycloalkyl containing 1–3 heteroatoms independently O, N, or S) substituent group, —C(O)C$_1$–C$_6$alkyl substituent group, —C(O)—O—C$_1$–C$_6$alkyl substituent group, —SC$_1$–C$_6$alkyl substituent group, —S(O)$_2$C$_1$–C$_6$alkyl substituent group, wherein any of the substituent groups is optionally substituted with 1–5 independently —OH or halogen.

24. The compound according to claim 23, or a pharmaceutically acceptable salt thereof, wherein X is C;

Y is S; and

R$_3$ and R$_5$ are absent.

25. The compound according to claim 1, represented by

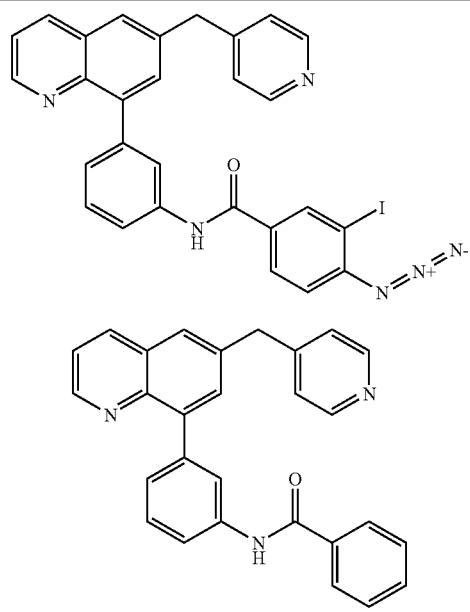

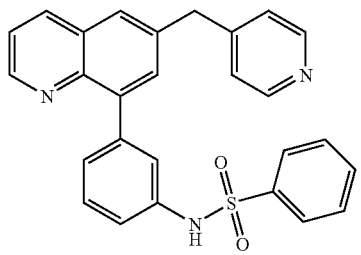
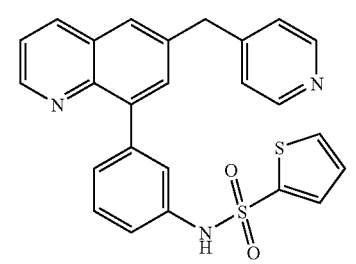
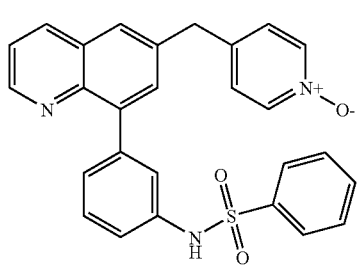
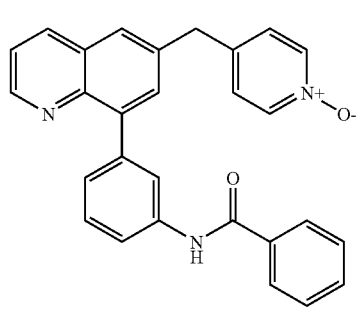
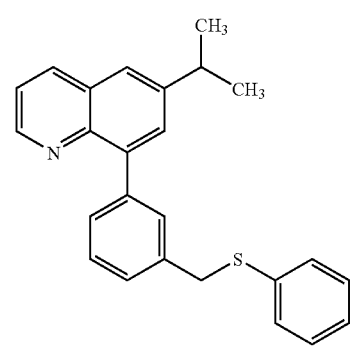
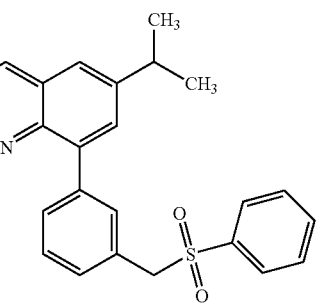
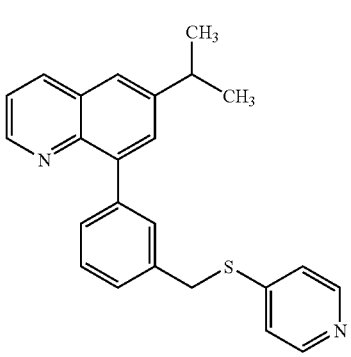
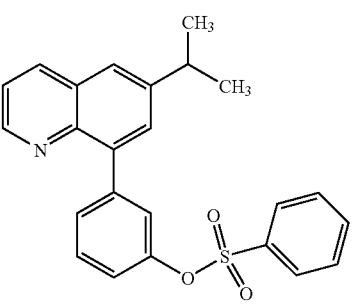
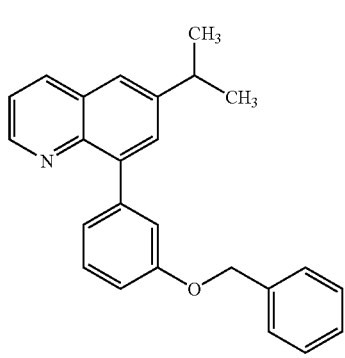
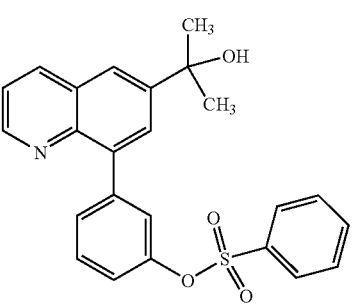

-continued
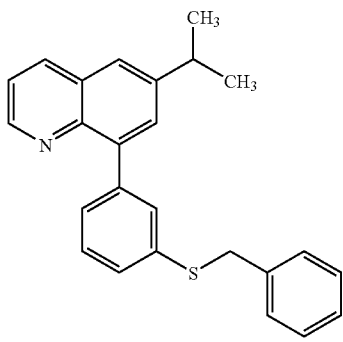
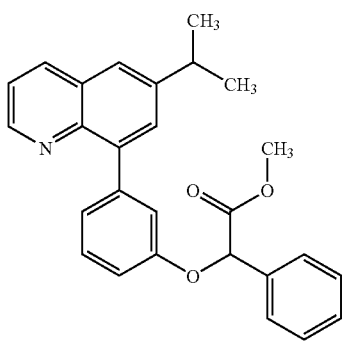
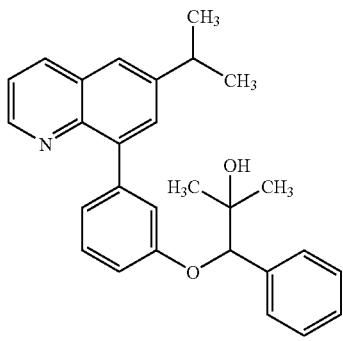
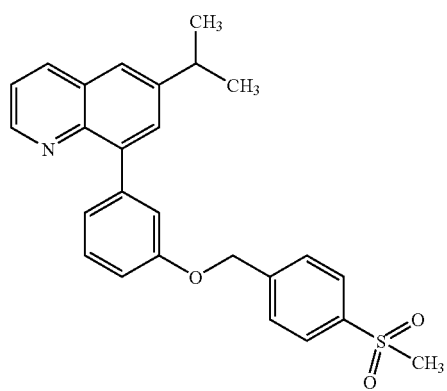
-continued
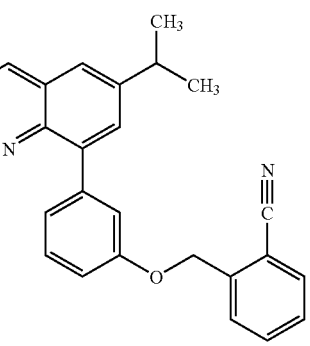
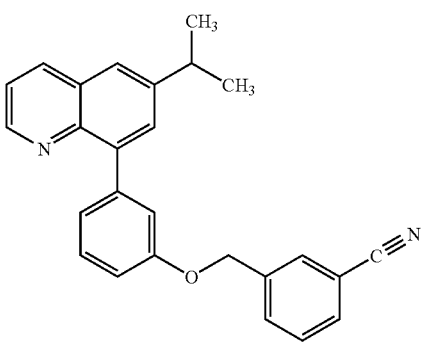
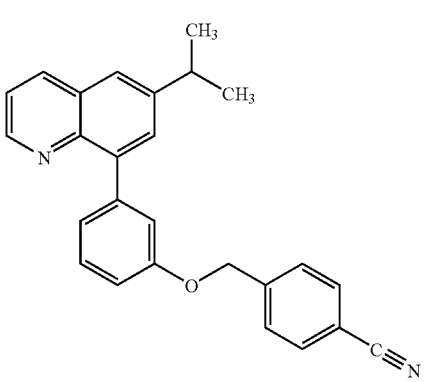
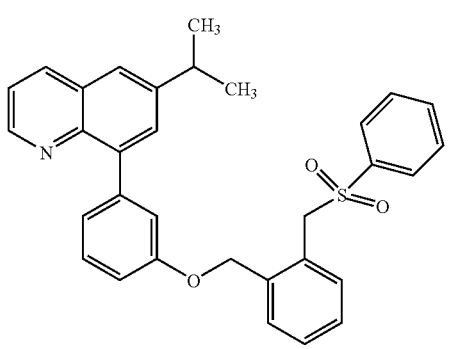

-continued
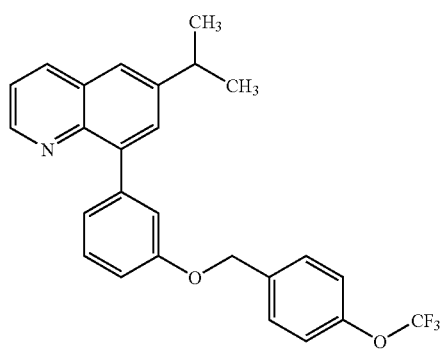
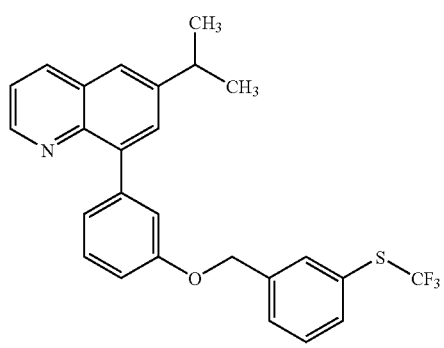
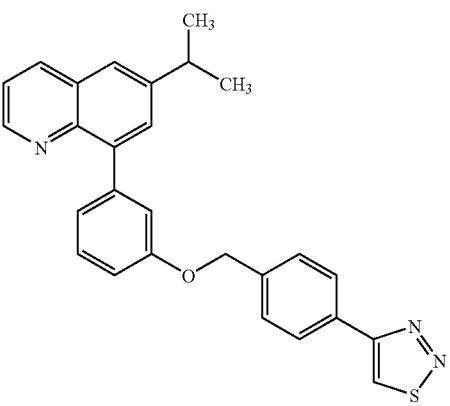
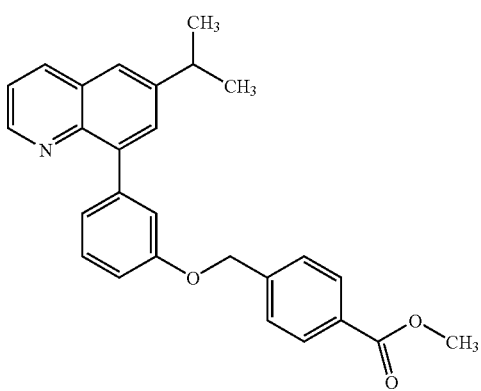
-continued
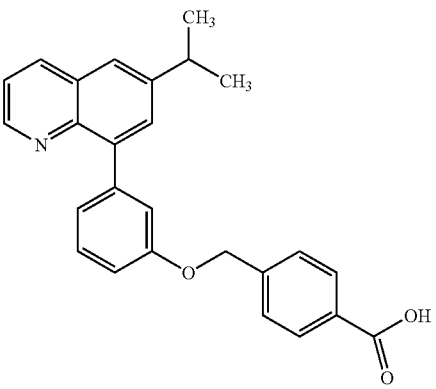
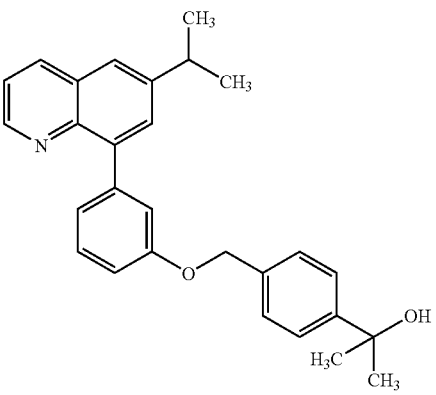
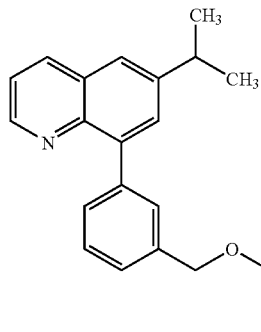
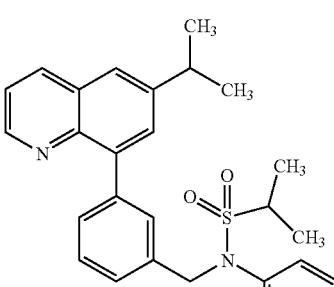

| 151 | 152 |
|---|---|
| -continued | -continued |
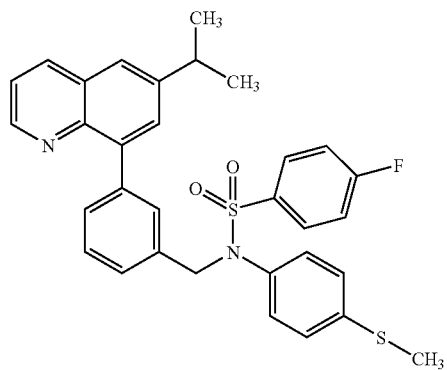
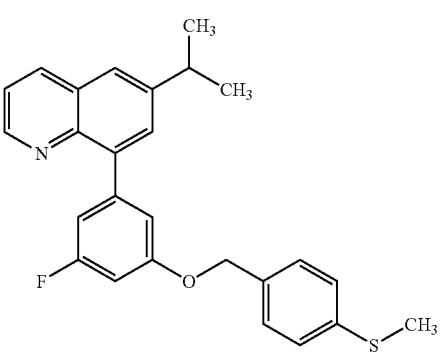

153                                             154
-continued                                      -continued
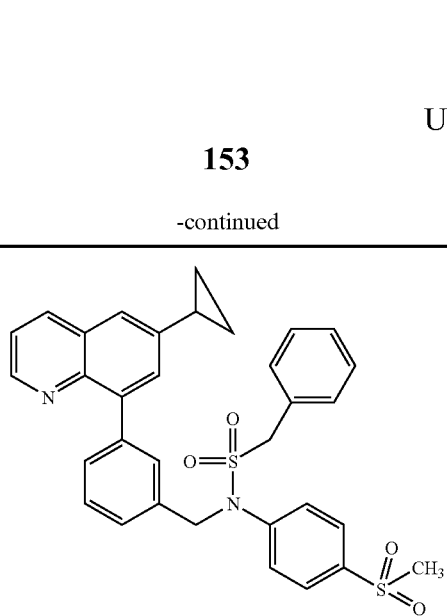
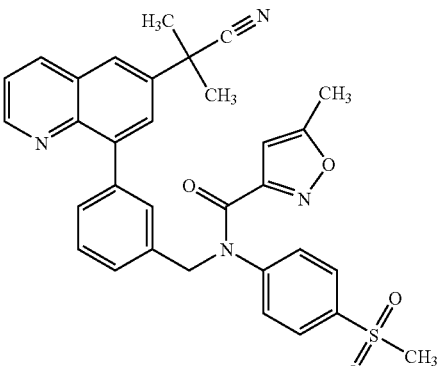
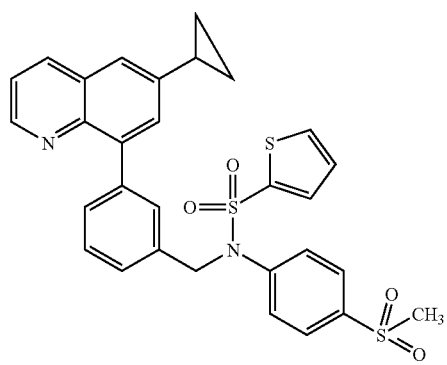
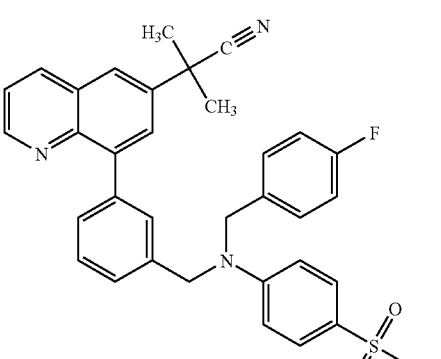
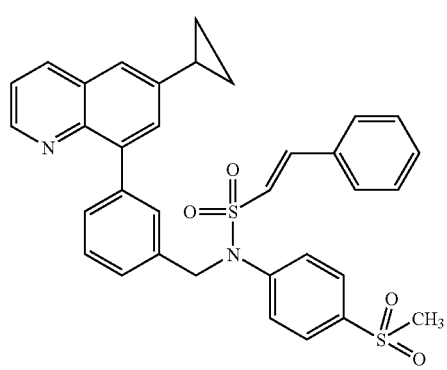
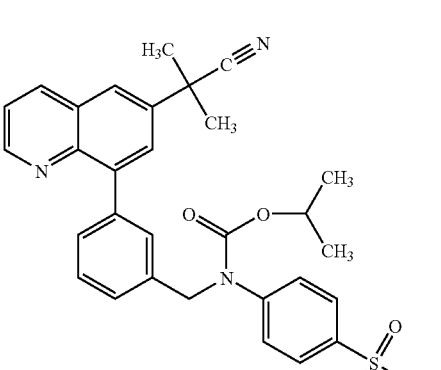
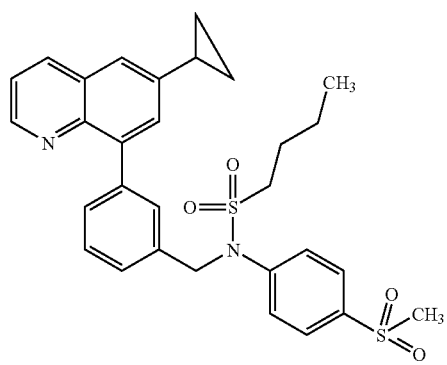
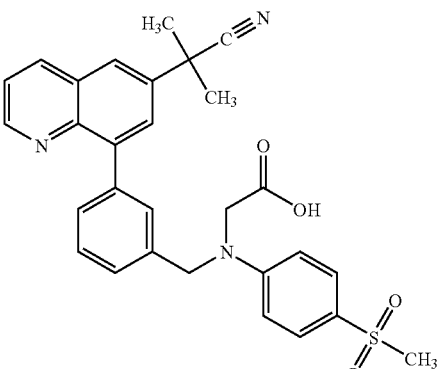

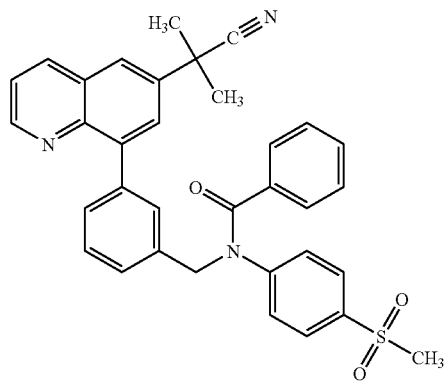
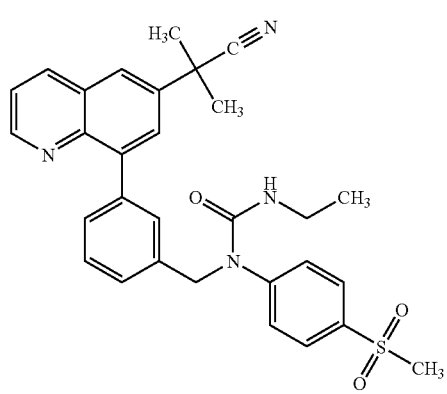
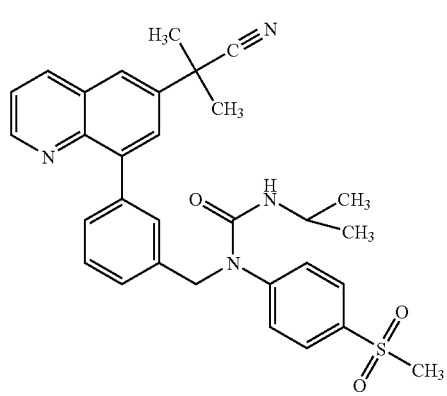
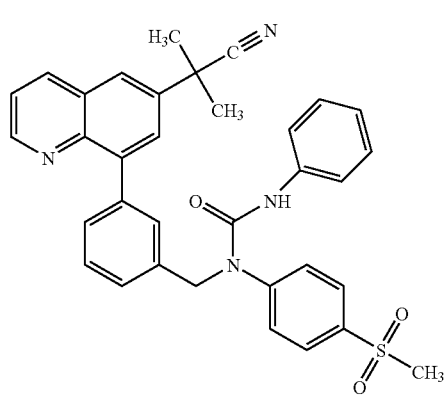
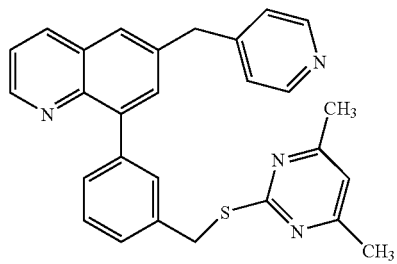
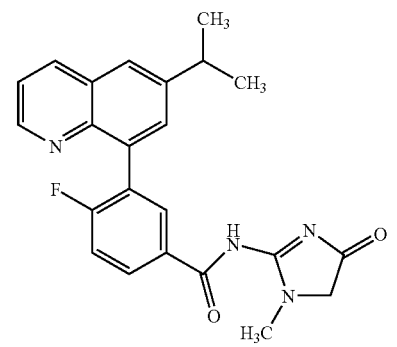
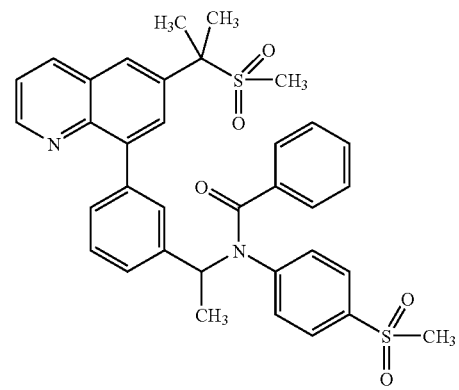
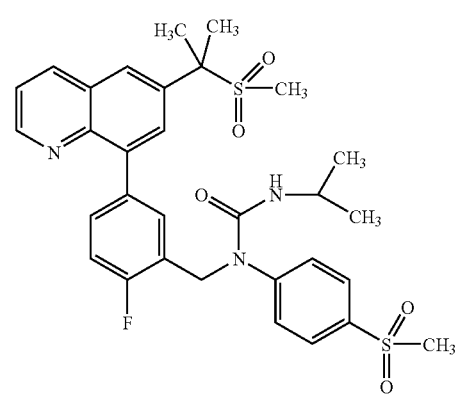

157
-continued
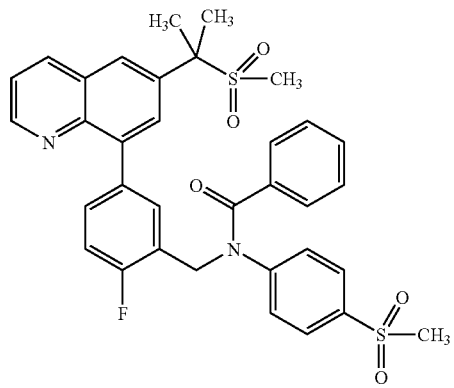
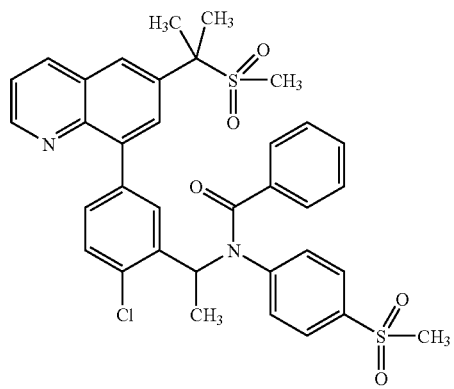
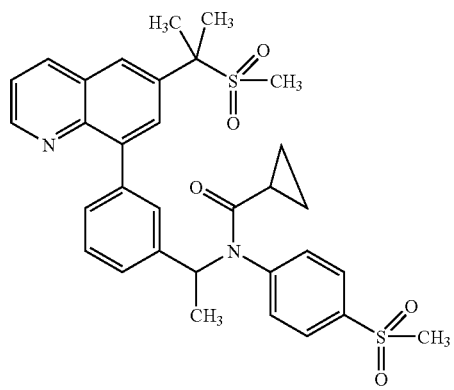
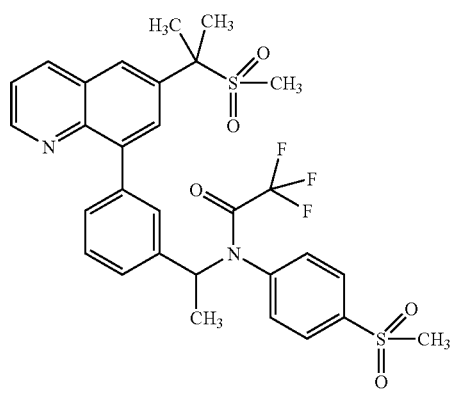
158
-continued
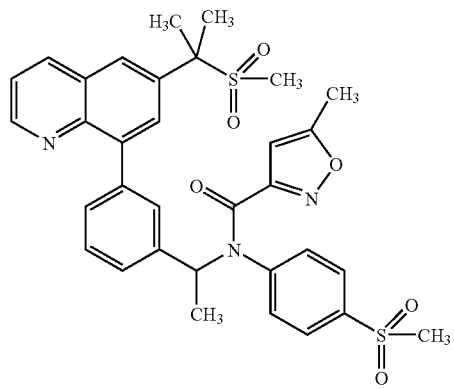
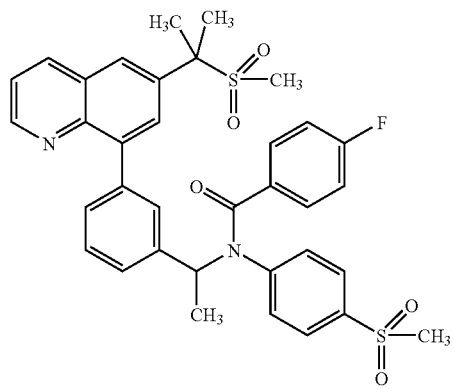
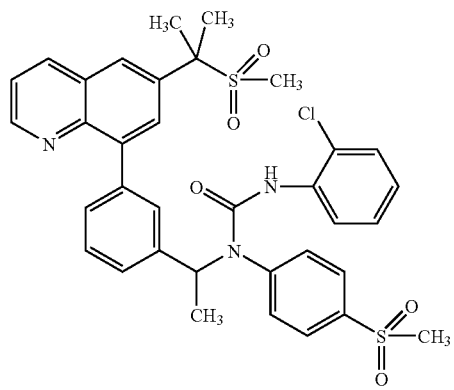
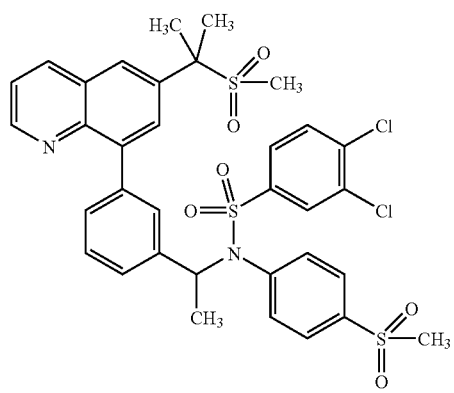

| 159 | 160 |
|---|---|
| -continued | -continued |
| 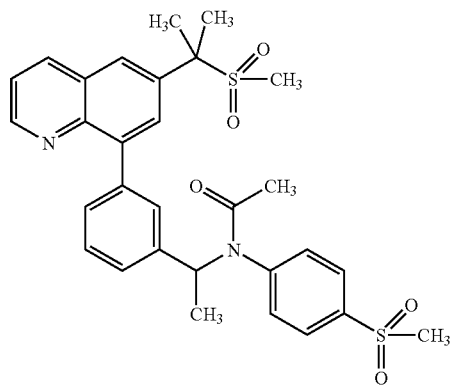 | 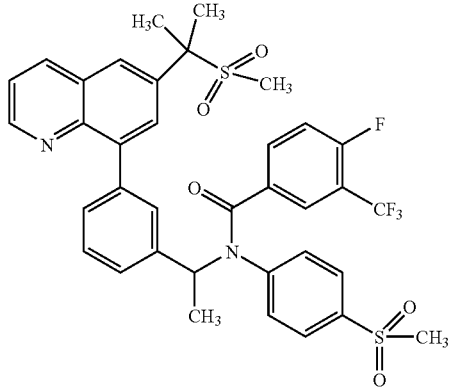 |
| 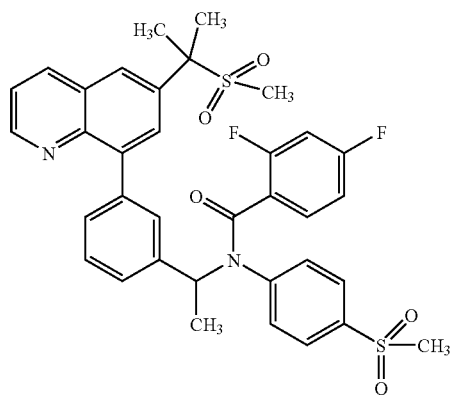 | 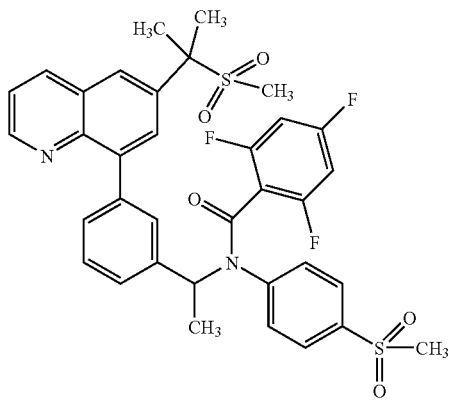 |
| 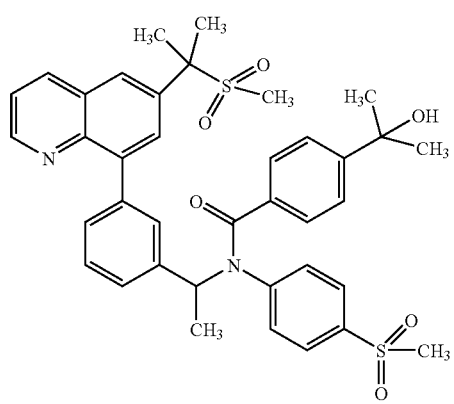 | 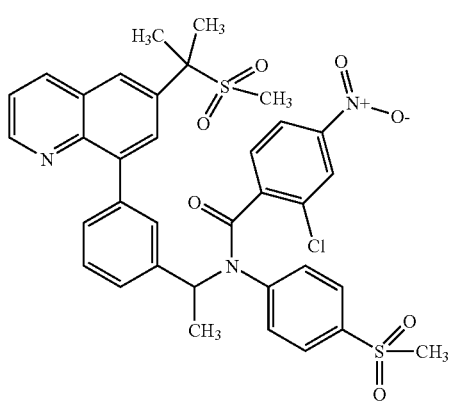 |
| 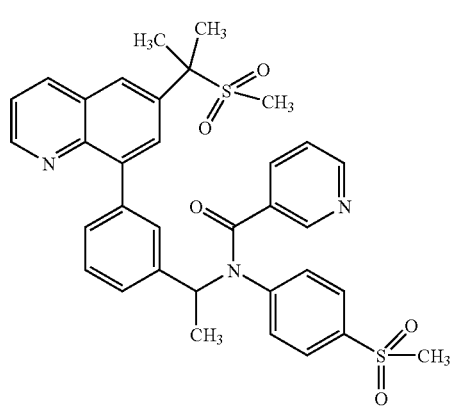 | 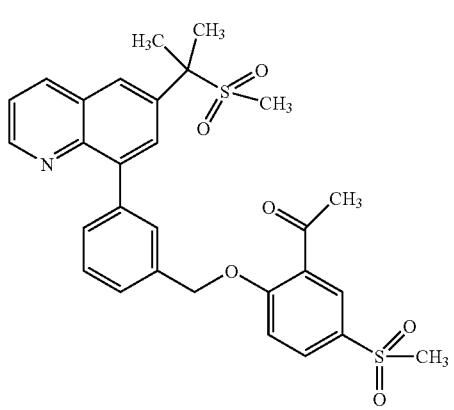 |

| 161 | 162 |
|---|---|
| 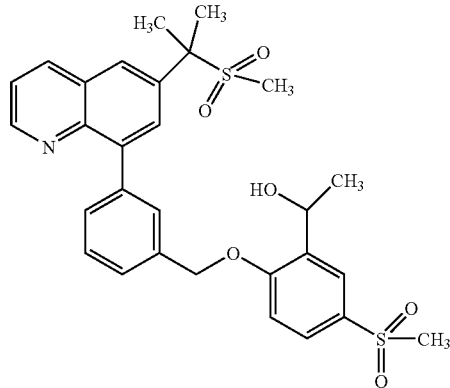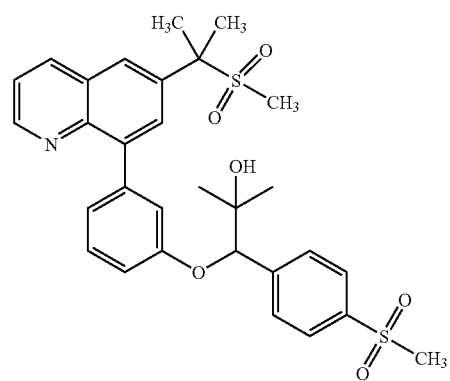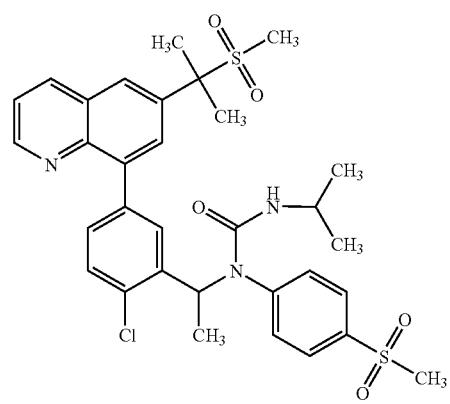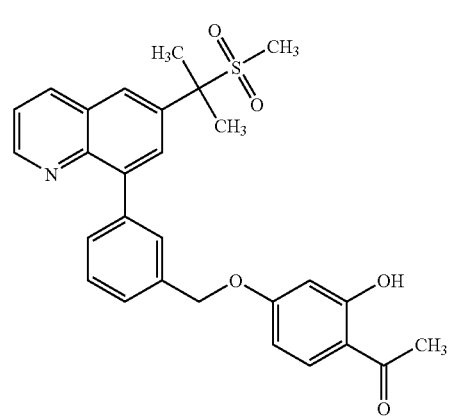 | 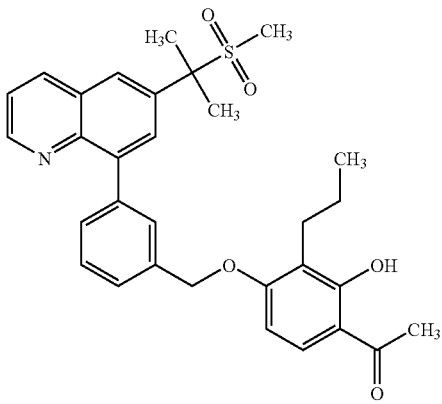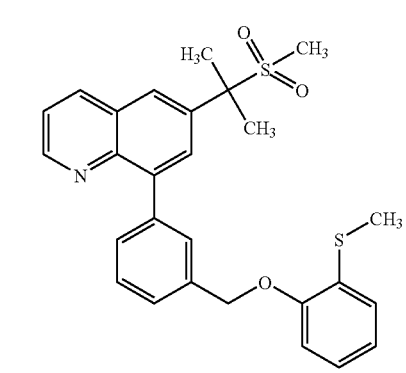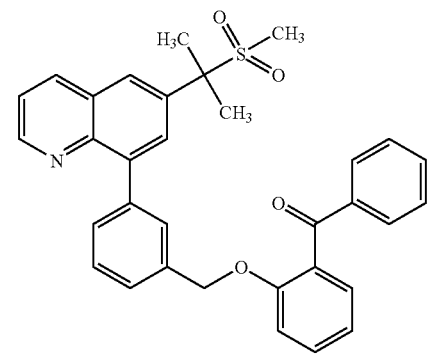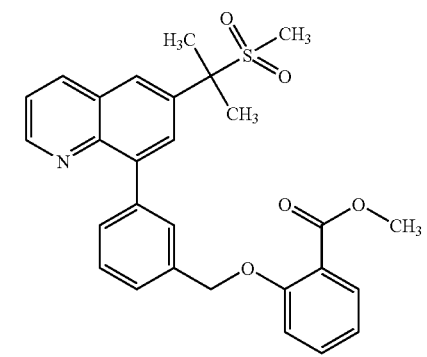 |

163
-continued
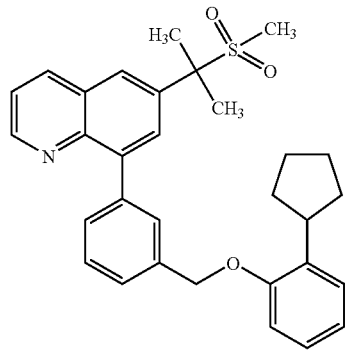
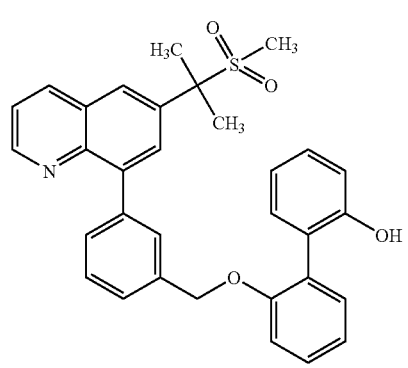
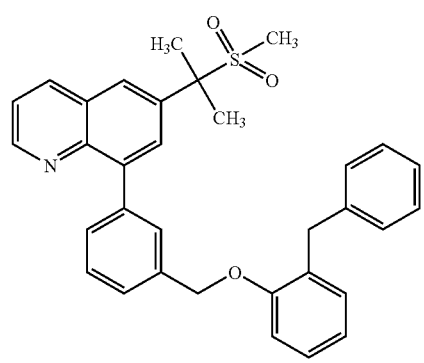
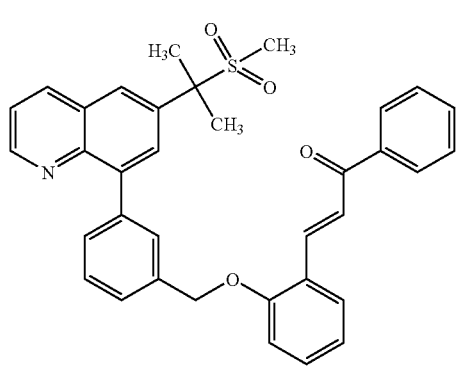
164
-continued
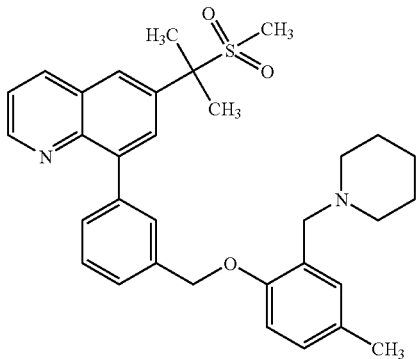
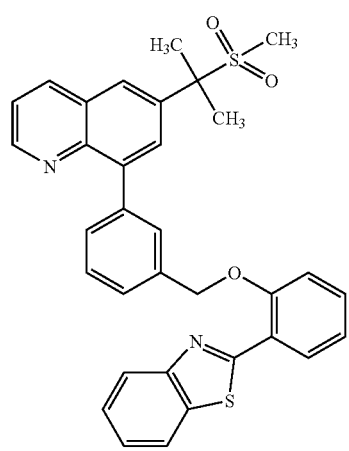
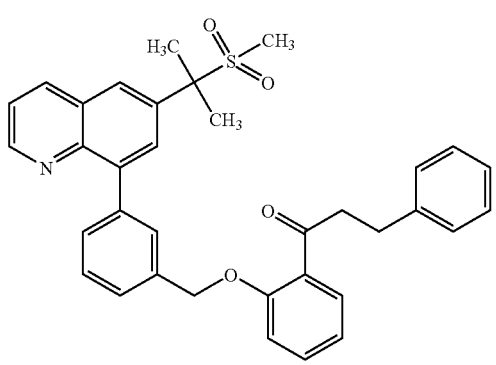
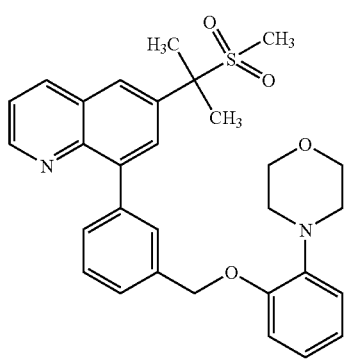

-continued
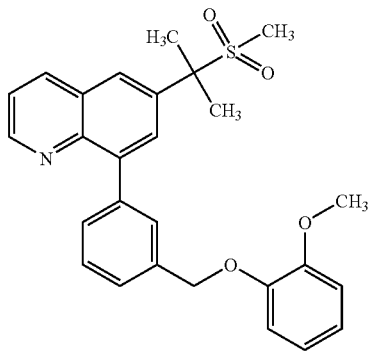
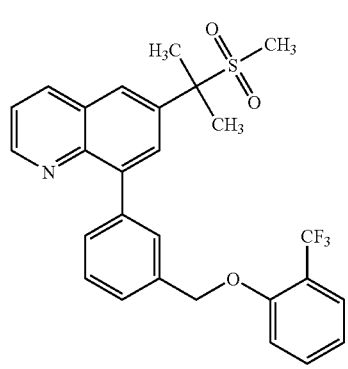
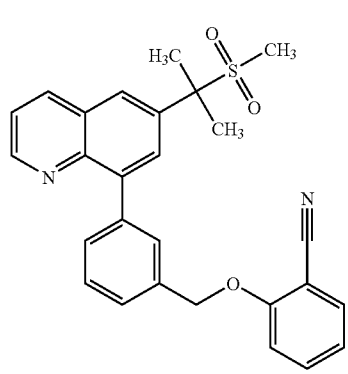
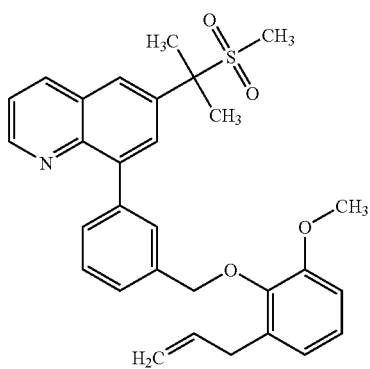
-continued
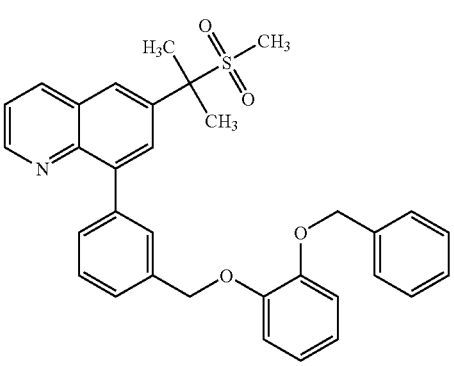
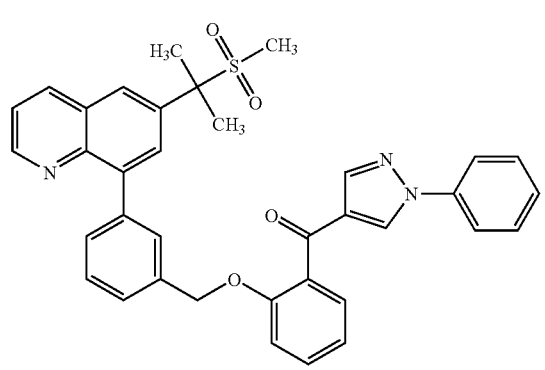
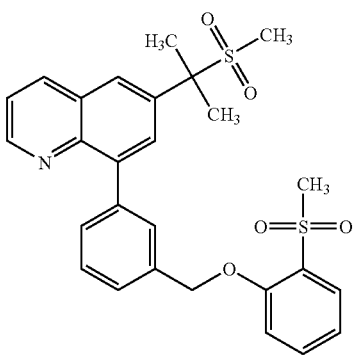
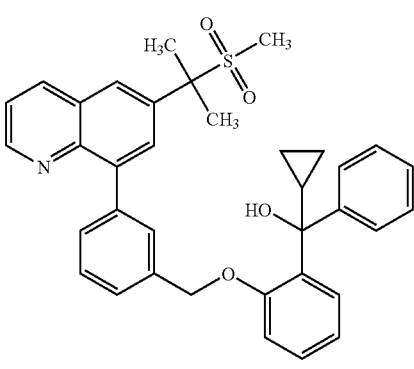

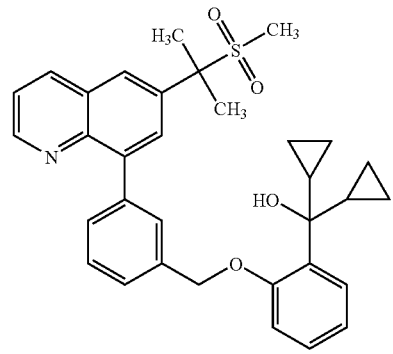
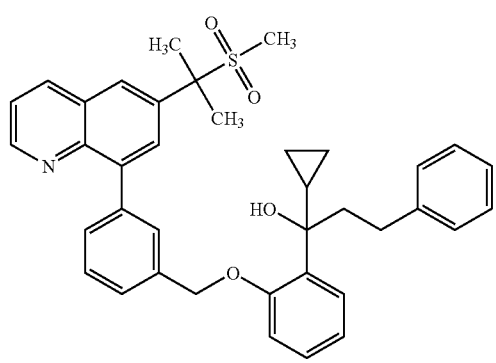
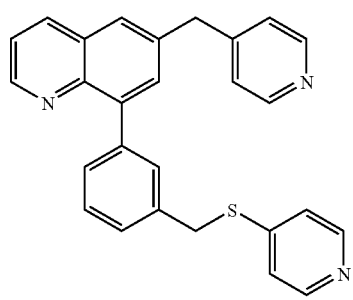
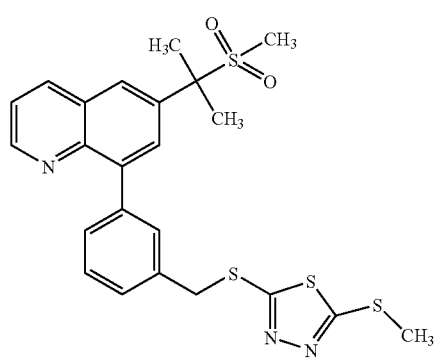
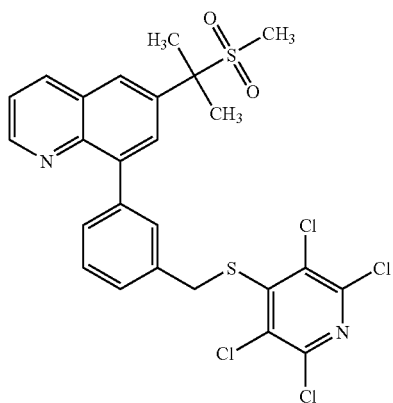
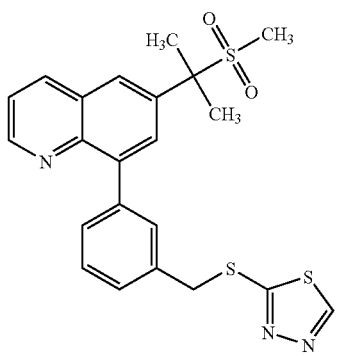
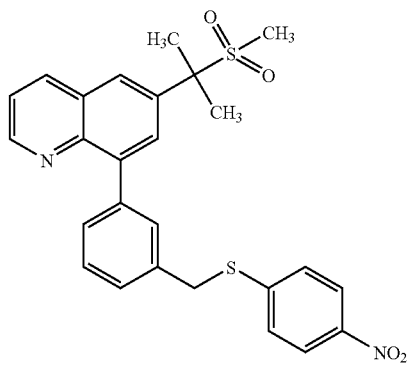
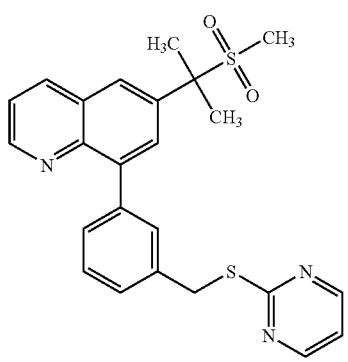

-continued
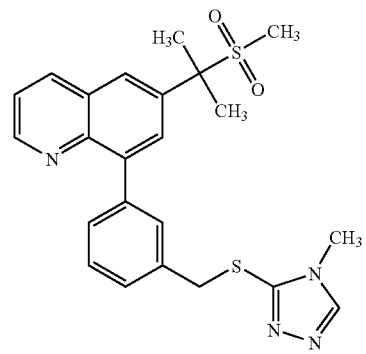
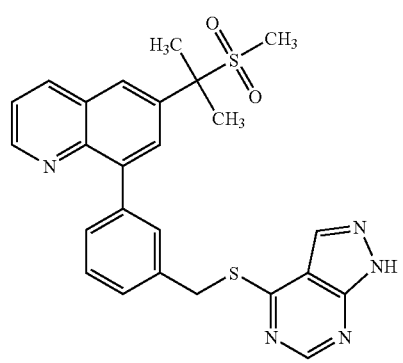
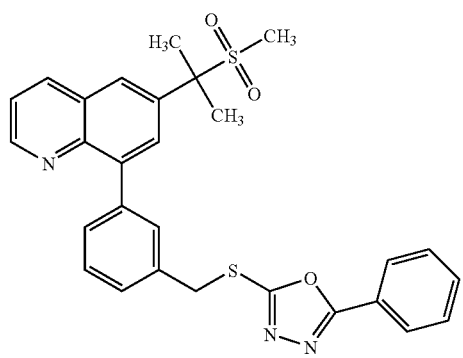
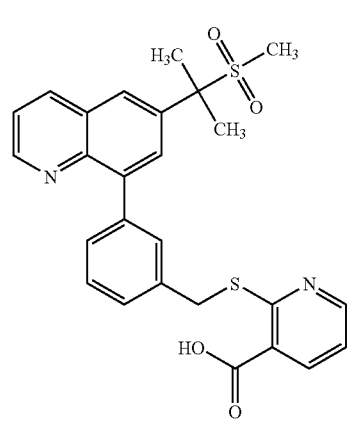
-continued
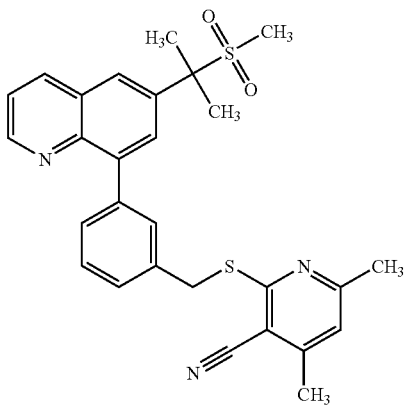
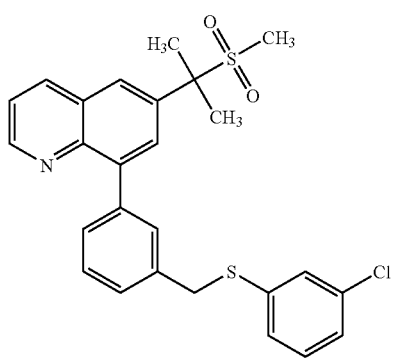
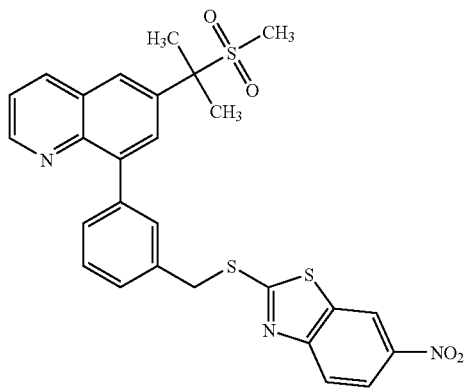
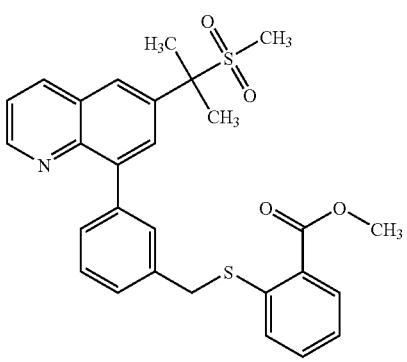

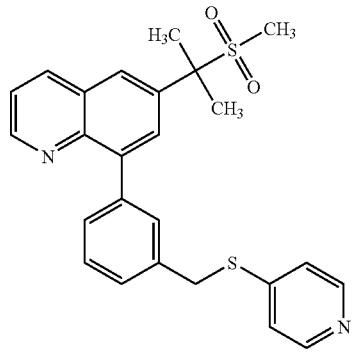
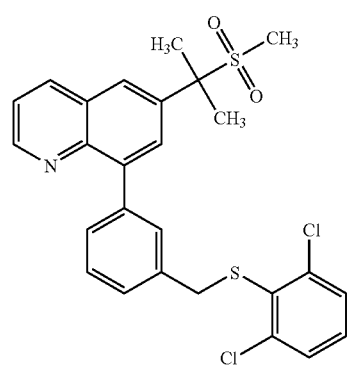
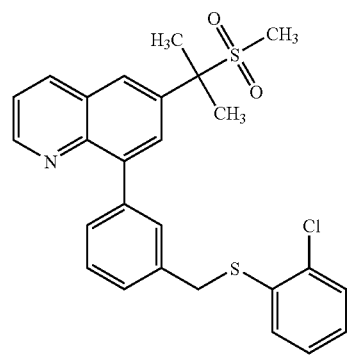
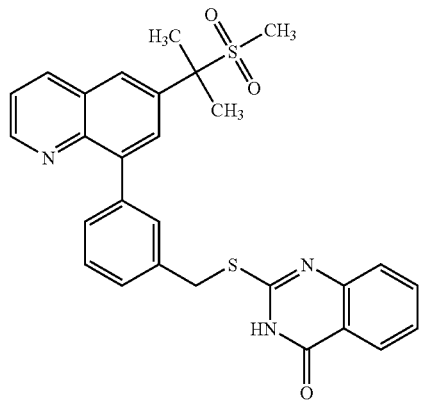
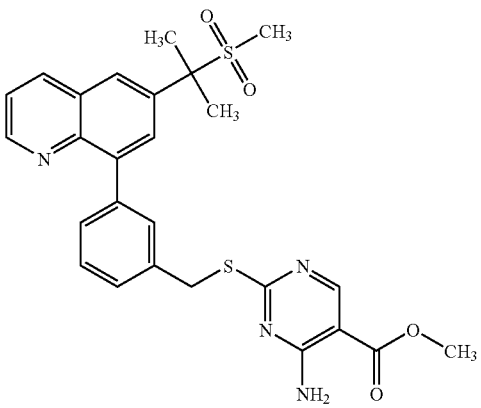
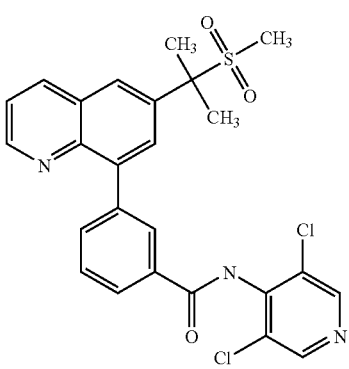
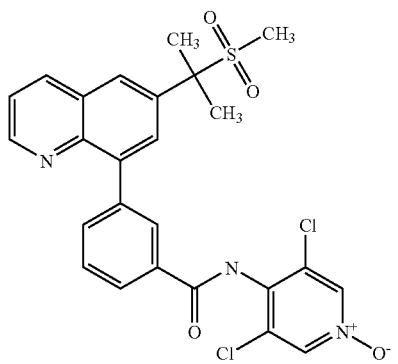
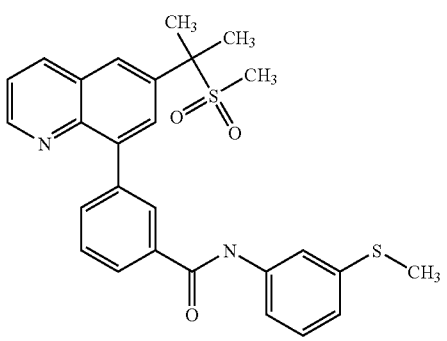

173                                    174
-continued                         -continued
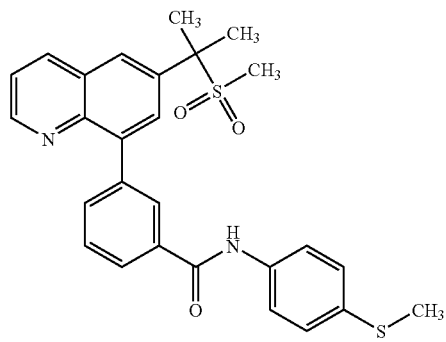
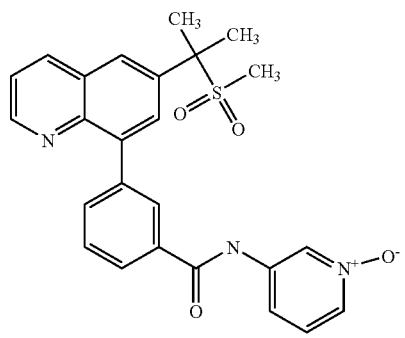
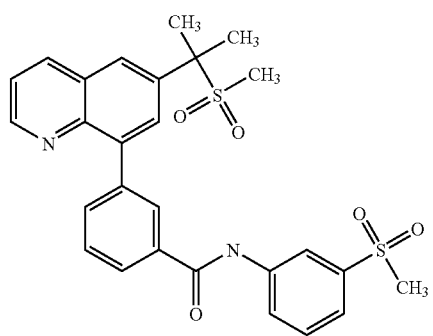
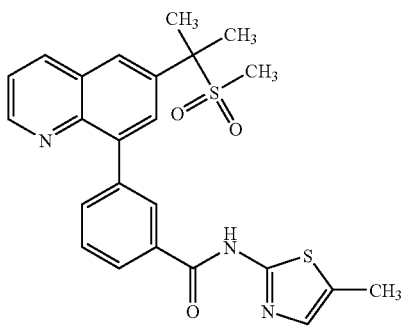
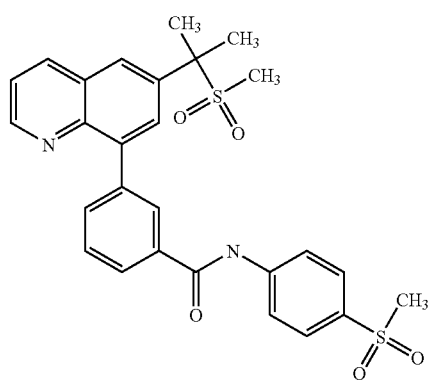
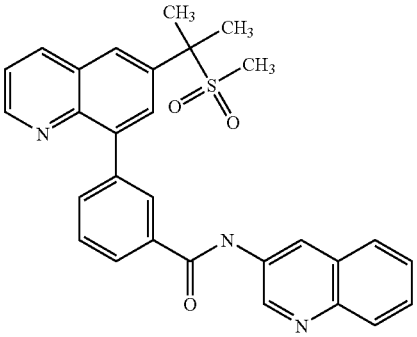
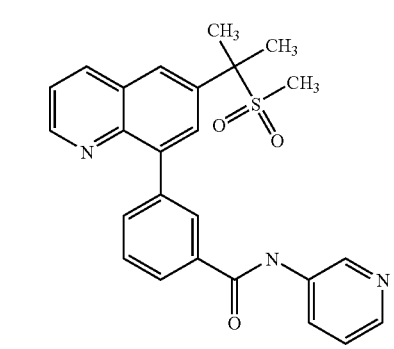
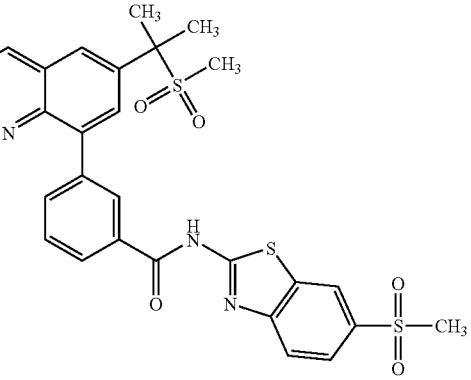

| 175 | 176 |
|---|---|
| -continued | -continued |
| 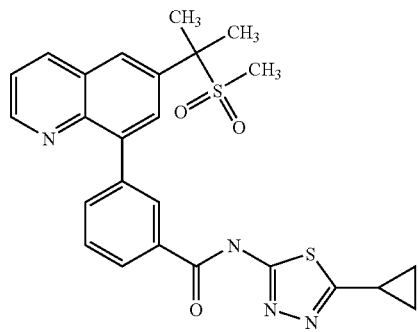 | 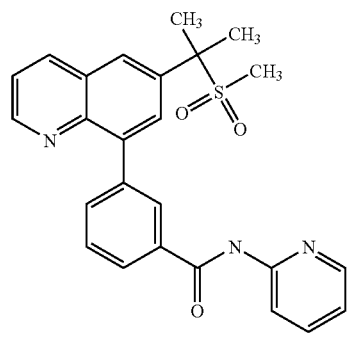 |
| 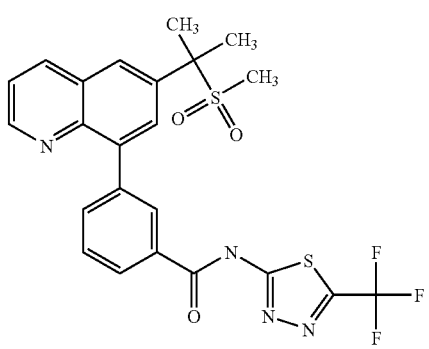 | 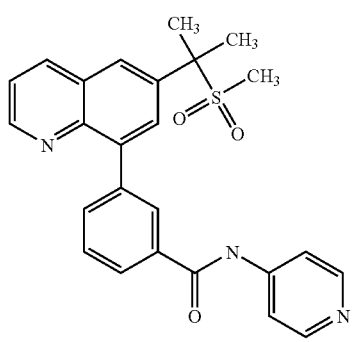 |
| 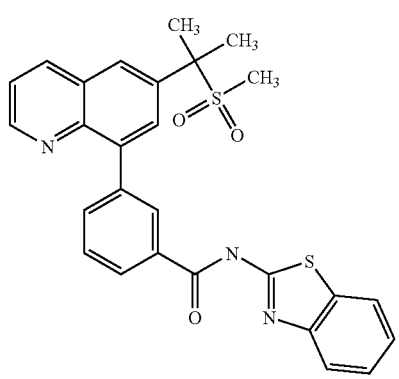 | 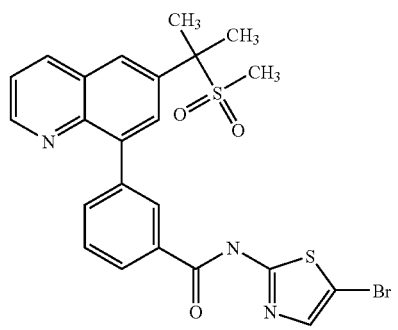 |
| 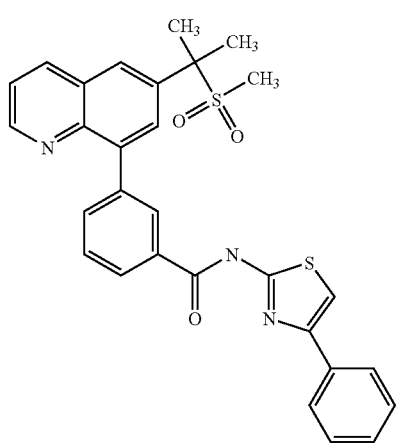 | 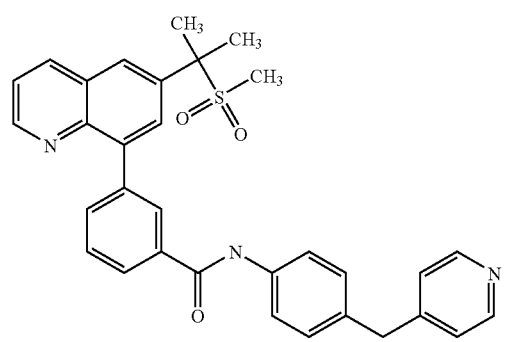 |

-continued

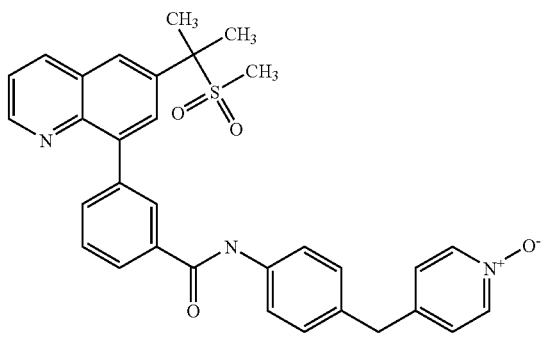

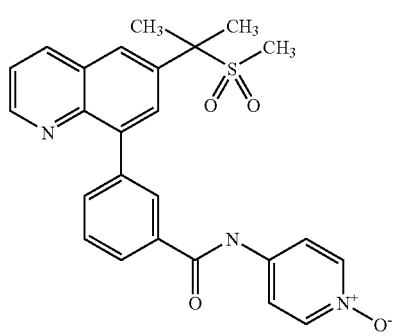

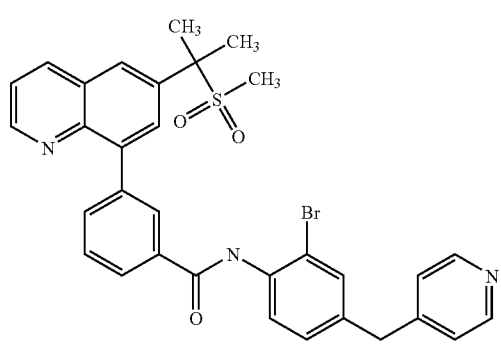

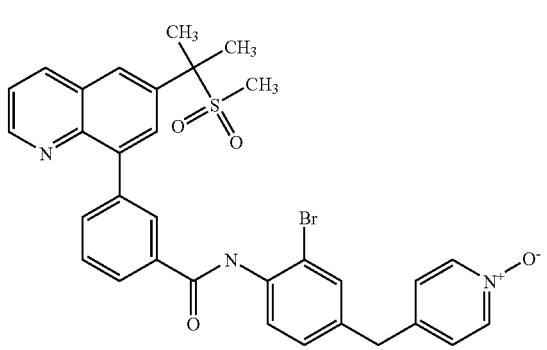

-continued

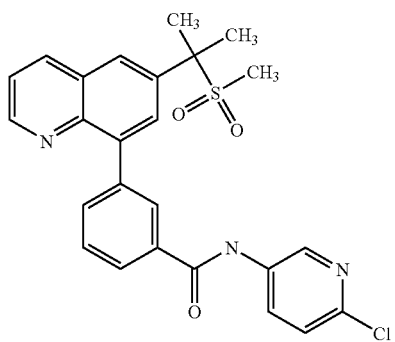

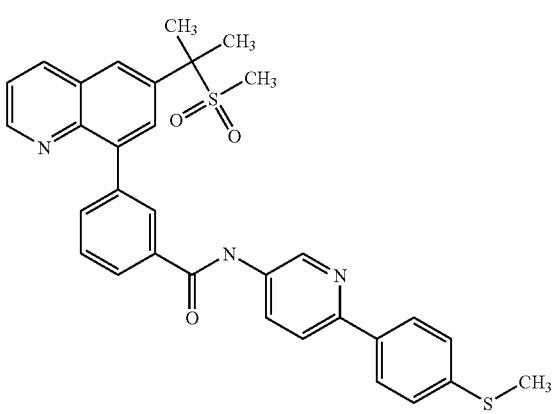

or a pharmaceutically acceptable salt thereof.

26. A pharmaceutical composition comprising:
 a therapeutically effective amount of the compound according to claim 1 or a pharmaceutically acceptable salt thereof; and
 a pharmaceutically acceptable carrier.

27. A method of inhibiting PDE-4 in a mammal comprising administering to the mammal a therapeutically effective amount of a compound according to claim 1 or a pharmaceutically acceptable salt there.

* * * * *